United States Patent [19]
Kasina et al.

[11] Patent Number: 5,968,477
[45] Date of Patent: Oct. 19, 1999

[54] RADIOLABELED ANNEXIN CONJUGATES WITH HEXOSE AND A CHELATOR

[75] Inventors: Sudhakar Kasina, Mercer Island; John M. Reno, Brier; Alan R. Fritzberg, Edmonds; Jonathan Tait, Seattle, all of Wash.

[73] Assignees: NeoRx Corporation; University of WA, both of Seattle, Wash.

[21] Appl. No.: 08/690,184

[22] Filed: Jul. 26, 1996

Related U.S. Application Data

[63] Continuation-in-part of application No. 08/351,653, Dec. 7, 1994, abandoned, which is a continuation-in-part of application No. 08/261,064, Jun. 16, 1994, abandoned, which is a continuation-in-part of application No. 08/185,660, Jan. 24, 1994, abandoned.

[51] Int. Cl.$^6$ .......................... A61K 51/08; A61K 35/14; C07F 5/00
[52] U.S. Cl. ...................... 424/1.69; 424/1.73; 424/9.34; 424/9.35; 530/380; 530/381; 534/10; 534/14
[58] Field of Search .................................. 424/1.69, 1.73, 424/9.34, 9.35; 530/380, 381; 514/802; 534/10, 11, 12, 13, 14

[56] References Cited

U.S. PATENT DOCUMENTS

| | | |
|---|---|---|
| 4,217,339 | 8/1980 | Bohn et al. |
| 4,348,316 | 9/1982 | Bohn et al. |
| 4,410,688 | 10/1983 | Denkelwalter et al. |
| 4,455,290 | 6/1984 | Olexa et al. |
| 4,507,229 | 3/1985 | Bohn . |
| 4,507,466 | 3/1985 | Tomalia et al. |
| 4,518,584 | 5/1985 | Mark et al. |
| 4,558,120 | 12/1985 | Tomalia et al. |
| 4,568,737 | 2/1986 | Tomalia et al. |
| 4,571,336 | 2/1986 | Houck et al. |
| 4,587,329 | 5/1986 | Tomalia et al. |
| 4,592,863 | 6/1986 | Bohn et al. |
| 4,594,328 | 6/1986 | Bohn . |
| 4,673,562 | 6/1987 | Davison et al. |
| 4,732,891 | 3/1988 | Maki et al. |
| 4,736,018 | 4/1988 | Reutelingsperger . |
| 4,746,505 | 5/1988 | Jones et al. |
| 4,746,731 | 5/1988 | Bohn . |
| 4,874,743 | 10/1989 | Wallner et al. |
| 4,879,224 | 11/1989 | Wallner et al. |
| 4,897,255 | 1/1990 | Fritzberg et al. |
| 4,937,324 | 6/1990 | Fujikawa et al. |
| 4,950,646 | 8/1990 | Wallner et al. |
| 4,959,314 | 9/1990 | Mark et al. |
| 4,965,392 | 10/1990 | Fritzberg et al. |

(List continued on next page.)

FOREIGN PATENT DOCUMENTS

| | | |
|---|---|---|
| 2021147 | 2/1991 | Canada . |
| 2032751 | 6/1991 | Canada . |
| 2040722 A1 | 10/1991 | Canada . |
| 055 028 A1 | 6/1982 | European Pat. Off. |
| 063 002 B1 | 10/1982 | European Pat. Off. |
| 351 826 A2 | 1/1990 | European Pat. Off. |
| 213 175 B1 | 8/1990 | European Pat. Off. |
| 432 988 A1 | 6/1991 | European Pat. Off. |
| 668 353 A1 | 8/1995 | European Pat. Off. |
| 668 354 A1 | 8/1995 | European Pat. Off. |
| 2 212 502 | 7/1989 | United Kingdom . |
| WO 86/04606 | 8/1986 | WIPO . |
| WO 86/06839 | 11/1986 | WIPO . |
| WO 89/10140 | 11/1989 | WIPO . |
| WO 91/07187 | 5/1991 | WIPO . |
| WO 91/09628 | 7/1991 | WIPO . |
| WO 91/17168 | 11/1991 | WIPO . |
| WO 92/19279 | 11/1992 | WIPO . |
| WO 94/09036 | 4/1994 | WIPO . |
| WO 94/07537 | 5/1994 | WIPO . |
| WO 94/19024 | 9/1994 | WIPO . |
| WO 94/22490 | 10/1994 | WIPO . |
| WO 96/17618 | 6/1996 | WIPO . |

OTHER PUBLICATIONS

Hashida et al., "Hepatic targeting of drugs and proteins by chemical modification," *Journal of Controlled Release* 36(1): 99–107, 1995.

Kasina et al., "Preformed Chelate TC–99m Radiolabeling Of r–Annexin V For Arterial Thrombus Imaging," *Journal of Nuclear Medicine* 37(Suppl. 5): 29P., 1996.

Prescott et al., "Larch arabinogalactan for hepatic drug delivery: isolation and characterization of a 9 kDa arabinogalactan fragment," *Carbohydrate Research* 278(1): 113–128, 1995.

Alderson, "Scintigraphic Diagnosis of Pulmonary Embolism: Where Do We Go From Here?" *Radiology*, vol. 193, pp. 22–23, 1994.

Baldwin et al., "Purification and Partial Amino Acid Sequence of Annexin V from Porcine Gastric Mucosal Membranes," *Comp. Biochem. Physiol.*, vol. 100B, No. 4, pp. 661–665, 1991.

Bautovich et al., "Detection of Deep Venous Thrombi and Pulmonary Embolus with Technetium–99m–DD–3B6/22 Anti–fibrin Monoclonal Antibody Fab' Fragment," *The Journal of Nuclear Medicine*, vol. 35, No. 2, pp. 195–202, 1994.

Biessen et al., "Synthesis of Cluster Galactosides with High Affinity for the Hepatic Asialoglycoprotein Receptor," *J. Med. Chem.*, vol. 38, pp. 1538–1546, 1995.

Bryson et al., "Protecting Groups in the Preparation of Thiolate Complexes of Technetium," *Inorganic Chemistry*, vol. 29, No. 16, pp. 2948–2951, 1990.

Cerqueira et al., "Noninvasive Arterial Thrombus Imaging with $^{99m}$Tc Monoclonal Antifibrin Antibody," *Circulation*, vol. 85, No. 1, pp. 293–304, 1992.

Crumpton, "Protein Terminology Tangle," *Nature*, vol. 345, p. 212, 1990.

(List continued on next page.)

*Primary Examiner*—José G. Dees
*Assistant Examiner*—Michael G. Hartley
*Attorney, Agent, or Firm*—Seed and Berry LLP

[57] ABSTRACT

Radiolabeled annexin and modified annexin conjugates useful for imaging vascular thrombi are described. Methods for making and using such radiolabeled annexin conjugates are also provided.

21 Claims, 9 Drawing Sheets

U.S. PATENT DOCUMENTS

| | | |
|---|---|---|
| 4,990,597 | 2/1991 | Löbermann et al. . |
| 5,026,913 | 6/1991 | McBride et al. . |
| 5,037,630 | 8/1991 | Fritzberg et al. . |
| 5,055,561 | 10/1991 | Packard et al. . |
| 5,071,636 | 12/1991 | Yamauchi et al. . |
| 5,075,099 | 12/1991 | Srinivasan et al. . |
| 5,080,884 | 1/1992 | McBride et al. . |
| 5,081,019 | 1/1992 | Wallner et al. . |
| 5,097,019 | 3/1992 | Löbermann et al. . |
| 5,104,638 | 4/1992 | Nosco . |
| 5,106,951 | 4/1992 | Morgan, Jr. et al. . |
| 5,112,954 | 5/1992 | Abrams et al. . |
| 5,120,526 | 6/1992 | Fritzberg et al. . |
| 5,162,505 | 11/1992 | Dean et al. . |
| 5,164,176 | 11/1992 | Gustavson et al. . |
| 5,179,081 | 1/1993 | Iwasaki et al. . |
| 5,202,419 | 4/1993 | Grundmann et al. . |
| 5,225,537 | 7/1993 | Foster . |
| 5,242,679 | 9/1993 | Fritzberg et al. . |
| 5,250,666 | 10/1993 | Gustavson et al. . |
| 5,252,713 | 10/1993 | Morgan, Jr. et al. . |
| 5,258,497 | 11/1993 | Reutelingsperger et al. . |
| 5,279,811 | 1/1994 | Bergstein et al. . |
| 5,288,623 | 2/1994 | Zenno et al. . |
| 5,296,467 | 3/1994 | Reutelingsperger . |
| 5,298,489 | 3/1994 | Wallner et al. . |
| 5,314,992 | 5/1994 | Guyre et al. . |
| 5,320,950 | 6/1994 | Grundmann et al. . |
| 5,322,678 | 6/1994 | Morgan, Jr. et al. . |
| 5,330,738 | 7/1994 | Nosco . |
| 5,371,184 | 12/1994 | Rajagopalan et al. . |
| 5,380,646 | 1/1995 | Knight et al. . |
| 5,484,711 | 1/1996 | Wallner et al. . |
| 5,589,395 | 12/1996 | Romisch et al. ........................... 436/71 |
| 5,616,690 | 4/1997 | Axworthy et al. ....................... 530/363 |
| 5,627,036 | 5/1997 | Reutelingsperger ................... 435/7.21 |
| 5,632,986 | 5/1997 | Tait et al. .............................. 424/9.464 |
| 5,645,815 | 7/1997 | Dean et al. ............................. 424/1.69 |
| 5,654,272 | 8/1997 | Dean ......................................... 514/12 |

OTHER PUBLICATIONS

De Bruyn et al., "Visualization of Thrombi in Pulmonary Arteries with Radiolabeled, Enzymatically Inactivated Tissue–Type Plasminogen Activator," 1995 , vol. 92, No. 5, pp. 1320–1325.

Demange et al., "Annexin V: The Key to Understanding Ion Selectivity and Voltage Regulation?," *TIBS*, vol. 19, pp. 272–276, 1994.

Fernandez et al., "The Structure of Anchorin CII, a Collagen Binding Protein Isolated from Chondrocyte Membrane," *J. Biolog. Chem.*, vol. 236, No. 12, pp. 5921–5925, 1988.

Findeis, "Stepwise Synthesis of a GalNAc–containing Cluster Glycoside Ligand of the Asialoglycoprotein Receptor," *Int. J. Peptide Protein Res.*, vol. 43, pp. 477–485, 1994.

Flaherty et al., "Placental Anticoagulant Protein–I: Measurement in Extracellular Fluids and Cells of the Hemostatic System," *The Journal of Laboratory and Clinical Medicine*, vol. 115, No. 2, pp. 174–181, 1990.

Fraker et al., "Protein and Cell Membrane Iodinations with a Sparingly Soluble Chloroamide, 1,3,4,6–tetrachloro–3a, 6a–diphenylglycoluril," *Biochemical and Biophysical Research Communications*, vol. 80, No. 4, pp. 849–857, 1978.

Fritzberg et al., "Specific and Stable Labeling of Antibodies with Technetium–99m with a Diamide Dithiolate Chelating Agent," *Proc. Natl. Acad. Sci. USA*, vol. 85, pp. 4025–4029, 1988.

Funakoshi et al., "Human Placental Anticoagulant Protein: Isolation and Characterization," *Biochemistry*, vol. 26, pp.5572–5578, 1987.

Funakoshi et al., "Primary Structure of Human Placental Anticoagulant Protein," *Biochem.*, vol. 26, pp. 8087–8092, 1987.

Galli et al., "A Radiopharmaceutical for the Study of the Liver: $^{99m}$Tc–DTPA–Asialo–Orosomucoid, I: Radiochemical and Animal Distribution Studies," *J. Nucl. Med. Allied Sci.*, vol. 32, No. 2, pp. 110–116, 1988.

Grundmann et al., "Characterization of cDNA Encoding Human Placental Anticoagulant Protein (PP4): Homology with the Lipocortin Family," *Proc. Natl. Acad. Sci.*. vol. 85, pp. 3708–3712, 1988.

Habeeb, "Determination of Free Amino Groups In Proteins by Trinitrobenzenesulfonic Acid," *Analytical Biochemistry*, vol. 14, pp. 328–336, 1966.

Haensler et al., "Synthesis and Characterization of a Trigalactosylated Bisacridine Compound to Target DNA to Hepatocytes," *Bioconjugate Chem.*, vol. 4, pp. 85–93, 1993.

Iwasaki et al., "Structure and Expression of cDNA for an Inhibitor of Blood Coagulation Isolated from Human Placenta: A New Lipocortin–like Protein," *J. Biochem.*, vol. 102, pp. 1261–1273, 1987.

Jansen et al., "Hepatic Endocytosis of Various Types of Mannose–terminated Albumins," *J. of Biological Chem.*, vol. 266, No. 5, pp. 3343–3348, 1991.

Kaplan et al., "Cloning and Expression of cDNA for Human Endonexin II, a $Ca^{2+}$ and Phospholipid Binding Protein," *J. Biolog. Chem.*, vol. 263, No. 17, pp. 8037–8043, 1988.

Kasina et al., "Development and Biologic Evaluation of a Kit for Preformed Chelate Technetium–99m Radiolabeling of an Antibody Fab Fragment Using a Diamide Dimercaptide Chelating Agent," *The Journal of Nuclear Medicine*, vol. 32, No. 7, pp. 1445–1451, 1991.

Knight et al., "Thrombus Imaging with Technetium–99m Synthetic Peptides Based upon the Binding Domain of a Monoclonal Antibody to Activated Platelets," *The Journal of Nuclear Medicine*, vol. 35, No. 2, pp. 282–288, 1994.

Koblick et al., "Current Status of Immunoscintigraphy in the Detection of Thrombosis and Thromboembolism," *Seminars in Nuclear Medicine*, vol. XIX, No. 3, pp. 221–237, 1989.

Krantz et al., "Attachment of Thioglycosides to Proteins: Enhancement of Liver Membrane Binding," *Biochem.*, vol. 15, No. 18, pp. 3963–3968, 1976.

Law, et al., "A Microplate Method for the Determination of Amino Groups in Monoclonal Antibodies," *Hybridoma*, vol. 9, No. 4, pp. 397–399, 1990.

Lee et al., "New Synthetic Cluster Ligands for Galactose/ N–Acetylgalactosamine–specific Lectin of Mammalian Liver," *Biochem.*, vol. 23, pp. 4255–4261, 1984.

Lee et al., "Preparation of Cluster Glycosides of N–Acetylgalactosamine That Have Subnanomolar Binding Constants Towards the Mammalian Hepatic Gal/GalNAc–specific Receptor," *Glycoconjugate J.*, vol. 4, pp. 317–328, 1987.

Lee et al., "2–Imino–2–methoxyethyl 1–thioglycosides: New Reagents for Attaching Sugars to Proteins," *Biochem.*, vol. 15, No. 18, pp. 3956–3962, 1976.

Loscalzo et al., "Imaging Arterial Thrombi: An Elusive Goal," *Circulation*, vol. 85, No. 1, pp. 385–385, 1992.

Mattes, "Biodistribution of Antibodies After Intraperitoneal or Intravenous Injection and Effect of Carbohydrate Modifications," *J. Natl. Canc. Instit.*, vol. 79, No. 4, pp. 855–863, 1987.

Mauk et al., "Targeting of Lipid Vesicles: Specificity of Carbohydrate Receptor Analogues for Leukocytes in Mice," *Proc. Natl. Acad. Sci. USA,* vol. 77, No. 8, pp. 4430–4434, 1980.

Maurer–Fogy et al., "Cloning and Expression of cDNA for Human Vascular Anticoagulant, a $Ca^{2+}$–dependent Phospholipid–binding Protein," *Eur. J. Biochem.,* vol. 174, pp. 585–592, 1988.

Mckee et al., "Preparation of Asialoorosomucoid–polylysine Conjugates," *Bioconjugate Chem.,* vol. 5, pp. 306–311, 1994.

Merwin et al., "Targeted Delivery of DNA Using YEE(GalNacAH)$_3$, a Synthetic Glycopeptide Ligand for the Asialoglycoprotein Receptor," *Bioconjugate Chem.,* vol. 5, pp. 612–620, 1994.

Morell et al., "The Role of Sialic Acid in Determining the Survival of Glycoproteins in the Circulation," *J. Biol. Chem.,* vol. 246, No. 5, pp. 1461–1467, 1971.

Muto et al., "Detecting Deep Venous Thrombosis with Technetium–99m–Labeled Synthetic Peptide P280," *The Journal of Nuclear Medicine,* vol. 36, pp. 1384–1391, 1995.

Pepinsky et al., "Five Distinct Calcium and Phospholipid Binding Proteins Share Homology with Lipocortin I," *J. Biolog. Chem.,* vol. 263, No. 22, pp. 10799–10811, 1988.

Ponpipom et al., "Cell–specific Ligands for Selective Drug Delivery to Tissues and Organs," *J. Med. Chem.,* vol. 24, 1388–1395, 1981.

Ponpipom et al., "Cell Surface Carbohydrates for Targeting Studies," *Can. J. Chem.,* vol. 58, p. 214, 1980.

Press Release from American Biogenetic Sciences, "American Biogenetic Sciences, Inc Announces Its Completion of Phase I and Initiation of a Phase I/II Clinical Trial of MH1 for Imaging Blood Clots," 1995.

Ravant et al., "Use of Annexin–V to Demonstrate the Role of Phosphatidylserine Exposure in the Maintenance of Haemostatic Balance by Endothelial Cells," *Biochem. J.,* vol. 282, pp. 7–13, 1992.

Römisch et al., "Annexins: Calcium–Binding Proteins of Multi–Functional Importance?," *Medical Microbiology and Immunology,* vol. 180, pp. 109–126, 1991.

Römisch et al., "Annexin Proteins PP4 and PP4–X: Comparative Characterization of Biological Activities of Placental and Recombinant Proteins," *Biochem. J.,* vol. 272, pp. 223–229, 1990.

Römisch et al., "Anticoagulant Properties of Placenta Protein 4 (Annexin V)," *Thrombosis Research,* vol. 60, No. 5, pp. 355–366, 1990.

Römisch et al., "In–Vivo Antithrombotic Potency of Placenta Protein 4 (Annexin V)," *Thrombosis Research,* vol. 61, No.2, pp. 93–104, 1991.

Sharma et al., "Inactivation and Clearance of an Anti–CEA Carboxypeptidase G2 Conjugate in Blood After Localisation in a Xenograft Model," *Br. J. Cancer,* vol. 61, pp. 659–662, 1990.

Sharon et al., "Carbohydrates in Cell Recognition," *Scientific American,* vol. 268, No. 1, pp. 82–89, 1993.

Stratton, "Common Causes of Cardia Emboli—Left Ventricular Thrombi and Atrial Fibrilation," *The Western Journal of Medicine,* vol. 151, No. 2, pp. 172–179, 1989.

Stratton et al., "The Effects of Antithrombotic Drugs in Patients with Left Ventricular Thrombi: Assessment with Indium–111 Platelet Imaging and Two–Dimensional Echocardiography," *Circulation,* vol. 69, No. 3, pp. 561–568, 1984.

Stratton et al., "$^{111}$In Platelet Imaging of Left Ventricular Thrombi," *Circulation,* vol. 81, No. 4, pp. 1182–1189, 1990.

Stratton et al., "Indium 111–Labeled Platelet Imaging in Man," *New Concepts Cardiac Imag,* vol. 3, pp. 139–196, 1987.

Stratton et al,. "Left Ventricular Thrombi: In Vivo Detection by Indium–111 Platelet Imaging and Two Dimensional Echocardiography," *The American Journal of Cardiology,* vol. 47, pp. 874–881, 1981.

Stratton et al., "Platelet Deposition at Carotid Endarterectomy Sites in Humans," *Stroke,* vol. 18, No. 4, pp. 722–727, 1987.

Stratton et al., "Reduction of Indium–111 Platelet Deposition on Dacron Vascular Grafts in Humans by Aspirin Plus Dipyridamole," *Circulation,* vol. 73, No. 2, pp. 325–330, 1986.

Stratton et al., "Selective Uptake of Radiolabeled Annexin V on Acute Porcine Left Atrial Thrombi.," vol. 92, No. 10, pp. 3113–3121, 1995.

Tait et al., "Chromosomal Localization of the Human Gene for Annexin V (Placental Anticoagulant Protein I) to 4q26→q28," *Cytogenet. Cell Genet.,* vol. 57, pp. 187–192, 1991.

Tait et al., "Evaluation of Annexin V as a Platelet–Directed Thrombus Targeting Agent," *Thrombosis Research,* vol. 75, No. 5, pp. 491–501, 1994.

Tait et al., "Phospholipid Binding of Annexin V: Effects of Calcium and Membrane Phosphatidylserine Content," *Archives of Biochemistry and Biophysics,* vol. 298, No. 1, pp. 187–191, 1992.

Tait et al., "Phospholipid Binding Properties of Human Placental Anticoagulant Protein–I, a Member of the Lipocortin Family," *J. Biolog. Chem.,* vol. 264, No. 14, pp. 7944–7949, 1989.

Tait et al., "Placental Anticoagulant Proteins: Isolation and Comparative Characterization of Four Members of the Lipocortin Family," *Biochem.,* vol. 27, No. 17, pp. 6268–6276, 1988.

Tait et al., "Site–Specific Mutagenesis of Annexin V: Role of Residues from Arg–200 to Lys–207 in Phospholipid Binding," *Archives of Biochemistry and Biophysics,* vol. 288, No. 1, pp. 141–144, 1991.

Tait et al., "Prourokinase–Annexin V Chimeras: Construction, Expression, and Characterization of Recombinant Proteins," *The Journal of Biological Chemistry,* vol. 270, No. 37, pp. 21594–21599, 1995.

Taliaferro et al., "New Multidentate Ligands: 22. N,N'–Dipyridoxylethylenediamine–N,N'–diacetic Acid: A New Chelating Ligand for Trivalent Metal Ions," *Inorganic Chemistry,* vol. 23, No. 8, pp. 1188–1192, 1984.

Tanaka et al., "Preparation and Characterization of a Disulfide–linked Bioconjugate of Annexin V with the B–chain of Urokinase: An Improved Fibrinolytic Agent Targeted to Phospholipid–containing Thrombi," *Biochem.,* vol. 35, No. 3, pp. 922–929, 1996.

Thiagarajan et al., "Binding of Annexin V/Placental Anticoagulant Protein I to Platelets: Evidence for Phosphatidylserine Exposure in the Procoagulant Response of Activated Platelets," *The Journal of Biological Chemistry,* vol. 265, No. 29, pp. 17420–17423, 1990.

Tolleshaug, "Binding and Internalization of Asialo–glycoproteins by Isolated Rat Hepatocytes," *Int. J. Biochem.,* vol. 13, pp. 45–51, 1981.

Van Der Sluijs et al., "Drug Targeting to the Liver with Lactosylated Albumins: Does the Glycoprotein Target the Drug or is the Drug Targeting the Glycoprotein?", *Hepatology*, vol. 6, No. 4, pp. 723–728, 1986.

Van Heerde et al., "Binding of Recombinant Annexin V to Endothelial Cells: Effect of Annexin V Binding on Endothelial–Cell–Mediated Thrombin Formation," *Biochem. J.*, vol. 302, pp. 305–312, 1994.

Van Ryn–McKenna et al., "The Effects of Heparin and Annexin V on Fibrin Accretion after Injury in the Jugular Veins of Rabbits," *Thrombosis and Haemostasis*, vol. 69, No. 3, pp. 227–230, 1993.

Vera et al., "Tc–99m Galactosyl–Neoglycoalbumin: In Vitro Characterization of Receptor–Mediated Binding," *J. Nucl. Med.* vol. 5, No. 7, pp. 779–787, 1984.

Verstraete, "The Diagnosis and Treatment of Deep–vein Thrombosis," *The New England Journal of Medicine*, vol. 329, No. 19, pp. 1418–1419, 1993.

Wall et al., "The Galactose–specific Recognition System of Mammalian Liver: the Route of Ligand Internalization in Rat Hepatocytes" *Cell*, vol. 21, pp. 79–93, 1980.

Weber et al., "Enhanced Kidney Clearance with an Ester–linked $^{99m}$Tc–Radiolabeled Antibody Fab'–chelator Conjugate," *Bioconjugate Chem.*, vol. 1, pp. 431–437, 1990.

Weigel, "Chapter 14, Mechanisms and Control of Glycoconjugate Turnover," *Glycoconjugates Composition, Structure and Function*, edited by Allen et al., Marcel Dekker, Inc., New York, pp. 421–497, 1992.

Weigel, "Chapter 5, Endocytosis and Function of the Hepatic Asialoglycoprotein Receptor," *Subcellular Biochemistry*, vol. 19, Endocytic Components: Identification and Characterization, edited by Bergeron et al., Plenum Press, New York, pp. 125–161, 1993.

Weinmann et al., "Deep–vein Thrombosis," *The New England Journal of Medicine*, vol. 331, No. 24, pp. 1630–1641, 1994.

Wells et al., "Accuracy of Clinical Assessment of Deep–vein Thrombosis," *The Lancet*, vol. 345, pp. 1326–1330, 1995.

Worsley et al., "Role of Radionuclide Imaging in Patients with Suspected Pulmonary Embolism," *Nuclear Medicine*, vol. 31, No. 4, pp. 849–858, 1993.

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:1:

Ala Cys Asp His Ser Met
    1              5

(2) INFORMATION FOR SEQ ID NO:2:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:2:

CATATGGCAC AGCTTCTCA                                             19

(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:3:

GGATCCTTAG TCATCTTCTC CACA                                  24

(2) INFORMATION FOR SEQ ID NO:4:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:4:

GTACCTGGAT CCTTAGTCAT CTTCTCCGCG AGCAGCAGAA GAGCTTTCTT          50

(2) INFORMATION FOR SEQ ID NO:5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:5:

CGAAATTAAT ACGACTCACT ATAGGG          26

(2) INFORMATION FOR SEQ ID NO:6:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (xi) SEQUENCE DESCRIPTION: SEQ ID NO:6:

GGAATTCCAT ATGGCACAGG TTCTCAGAGG CACTGTG          37

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:7:

CGCGGATCCT TAGTCATCTT CTCCGGAGAG CAG          33

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:8:

TATGGCATGT GACCATTC          18

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:9:

TAGAATGGTC ACATGCCA          18

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:10:

```
    Met Ala Cys Asp His Ser
    1               5
```

(2) INFORMATION FOR SEQ ID NO:11:

```
    (i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:11:

Gly Gly Gly Gly Gly Gly
    1               5
```

RADIOLABELED ANNEXIN CONJUGATES WITH HEXOSE AND A CHELATOR

CROSS-REFERENCE TO RELATED APPLICATIONS

This application is a continuation-in-part of U.S. patent application Ser. No. 08/351,653, filed Dec. 7, 1994, now abandoned, which is in turn a continuation-in-part of U.S. patent application Ser. No. 08/261,064, filed Jun. 16, 1994, now abandoned, which is in turn a continuation-in-part of U.S. patent application Ser. No. 08/185,660, filed Jan. 24, 1994, now abandoned.

TECHNICAL FIELD

The present invention is directed to radiolabeled annexins, including annexin-hexose conjugates such as hexose moiety conjugates, and components thereof. The present invention is also generally directed to modifications of the annexin components for the use in the preparation of radiolabeled annexins. Also contemplated by the present invention are imaging protocols which involve the administration of, for example, a radiolabeled annexin-hexose moietyconjugate. The annexin component of the conjugate serves to deliver the radiolabeled active component of the conjugate to vascular thrombi target sites. The hexose component of the conjugate facilitates rapid elimination of the radiolabeled annexin-hexose moiety conjugates from the circulation of a recipient.

BACKGROUND OF THE INVENTION

When patients present with chest pain, palpitations or any other symptoms of coronary trauma or disease, the presence of vascular thrombi in the heart is a potential significant complicating factor for treatment. If a medical practitioner could non-invasively determine whether one or more vascular thrombi were present and, if present, the location of those vascular thrombi, better evaluation of treatment options would be possible. Furthermore, if a medical practitioner could determine that no vascular thrombi were present, thereby eliminating a potential complication in treatment, cardiac conditions could be treated more safely and effectively.

Most present techniques for determining the presence of vascular thrombi are invasive and/or cumbersome, and/or fail to detect such thrombi with good sensitivity and specificity. Thus, an imaging agent useful for non-invasive vascular thrombi imaging is desirable.

Annexins are a class of proteins that are characterized by calcium-mediated binding to anionic phospholipids. Anionic phospholipids are about 20-fold more highly associated with activated platelets than quiescent platelets, and activated platelets are associated with vascular thrombi.

Radioiodinated annexin V has been shown to localize to vascular thrombi in vivo, but has suboptimal imaging characteristics, possibly due to the pronounced beta phase of blood clearance owing to possible transiodination and/or metabolic degradation with reincorporation into serum macromolecules or non-target tissues. Free radioactive iodine or iodine-containing metabolic degradation products exposed non-target tissues, especially the thyroid gland, to radioactivity. Iodine radioisotopes I-123, I-124 and I-131 with imagable photons suffer from various drawbacks. Iodine-131 has particulate emission and its gamma emission is too high in energy for optimal imaging. Iodine-124 emits positrons and high energy gamma photons. Finally, I-iodine-123 radiolabel with superior imaging properties is expensive and difficult to obtain and is not therefore practical for wide spread use. Consequently, improved radiolabeled annexin compounds are desirable.

In addition, conventional imaging and therapy are often plagued by the problem that the generally attainable targeting ratio (ratio of administered dose localizing to target versus administered dose circulating in blood, or ratio of administered dose localizing to target versus administered dose migrating to bone marrow) is low. Improvement in targeting ratio is also sought.

Thus, for the foregoing reasons there is still a need for a thrombus imaging product with increased sensitivity to image small thrombi, such as carotid thrombi or intracardiac thrombi and those present in coronary arteries after angioplasty or during myocardial infarctions or in cerebral arteries during stroke. Development of a radiolabeled thrombus imaging agent capable of detecting intracoronary thrombi would represent a breakthrough product of great clinical and commercial significance. The present invention fulfills this need and provides further related advantages.

SUMMARY OF THE INVENTION

The present invention provides radiolabeled annexin-hexose moiety conjugates and methods of making and using the same. The present invention further provides an annexin component that is altered in such a way as to provide an accessible sulfhydryl group and/or other amino acid groups for derivatization so as to serve to improve the imaging properties of annexin. Annexin-containing conjugates of the present invention are suitable for radiolabeling with a diagnostic imaging agent. Preferred conjugates of the present invention include:

an annexin;

a hexose moiety; and an $N_2S_2$ chelating compound associated with the annexin.

Also provided by the present invention are radiolabeled annexin-hexose moiety-conjugates which include:

an annexin;

a hexose moiety;

an $N_2S_2$ chelating compound associated with the annexin; and a diagnostic radionuclide complexed by the chelating compound.

Another preferred conjugate of the present invention includes:

a modified annexin, wherein the modification provides an accessible sulfhydryl group; and a hexose moiety recognized by a mammalian liver receptor, wherein the hexose moiety is conjugated to the annexin.

Another preferred conjugate of the present invention includes:

a modified annexin, wherein the modification provides an accessible sulfhydryl group;

a hexose moiety recognized by a mammalian liver receptor; and a $N_xS_y$ chelating compound, wherein the hexose moiety is conjugated to the modified annexin directly or via the chelating compound and the chelating compound is conjugated to the modified annexin directly or via the hexose moiety.

Another preferred conjugate of the present invention includes:

an annexin multimer;

a hexose moiety recognized by a mammalian liver receptor; and a $N_xS_y$ chelating compound, wherein the hexose moiety is conjugated to the multimer directly or via the chelating compound and the chelating compound is conjugated to the multimer directly or via the hexose moiety.

Another preferred conjugate of the present invention includes:

an annexin; and an esterase-sensitive $N_xS_y$ chelating compound conjugated to the annexin.

Another preferred conjugate of the present invention includes:

a modified annexin, wherein the modification provides acessible sulfhydryl group; and a $N_xS_y$ chelating compound conjugated to the annexin.

Another preferred conjugate of the present invention includes:

a modified annexin, wherein the modification provides an accessible sulfhydrl group; and an esterase-sensitive $N_xS_y$ chelating compound conjugated to the annexin.

Another preferred conjugate of the present invention includes:

an annexin multimer; and a $N_xS_y$ chelating compound conjugated to the annexin.

Another preferred conjugate of the present invention includes:

an annexin multimer; and an esterase-sensitive $N_xS_y$ chelating compound conjugated to the annexin.

It will be understood by one of ordinary skill in the art that where a chelating compound is a component of the conjugate, any one of the above preferred conjugates further includes a radionuclide complexed by the chelating compound.

A preferred annexin for use in the present invention is annexin V. A modified annexin is extended on the C-terminus or N-terminus by a number of a amino acids. A preferred modified annexin for use in the present invention is extended on the N-terminus. This addition of the extension results in a modification to the annexin whereby an accessible sulfhydryl group is provided for. Thus, the modified annexin can be conjugated to a hexose moiety, such as a hexose cluster, (e.g., N-acetylgalactos-amine cluster; or provide for an endogenous radiolabel chelation site, thus eliminating the need for intermediate production of an amine-directed active ester containing the radiolabel; or provide for multimer production.

The modified annexin component of the conjugate allows for rapid binding of the radiolabel to the annexin, thus providing for a simplified labeling procedure for clinical use. In some embodiments of the present invention, the modification to the annexin provides for acceleration of blood clearance thereby reducing the background radioactivity of the blood pool.

Also, in some other embodiments of the present invention, an esterase-sensitive chelating compound is utilized to provide for accelerated excretion of radioactivity from the liver, thereby reducing background radioactivity adjacent to the heart and lungs.

Preferred hexose moieties for use in the present invention include hexose clusters and incorporate a multiple of 4 galactoses. Other preferred hexose clusters for use in the present invention incorporate a multiple of 3 galactoses.

The hexose moiety component may bound to the annexin component and the chelating compound component via a trifunctional linker, such as lysine. An extender may be employed between the hexose moiety and the trifunctional linker to promote bioavailability of the hexose moiety. This embodiment of the present invention is favored if the chelating compound is characterized by a single functional group available and suitable for conjugation.

If the chelating compound component is characterized by greater than one functional group available and suitable for conjugation to other conjugate components, a structure such as the following is preferably employed: hexose moiety—bifunctional linker—chelating compound—bifunctional linker—annexin.

Preferred diagnostic radionuclides for use in the practice of the present invention are Tc-99m, Re-186 and Re-188, with Tc-99m being especially preferred. Vascular thrombi located in or near the heart are especially amenable to imaging in accordance with the present invention.

These and other aspects of the present invention will become evident upon reference to the following description and attached drawings.

DETAILED DESCRIPTION OF THE INVENTION

Figure 1:
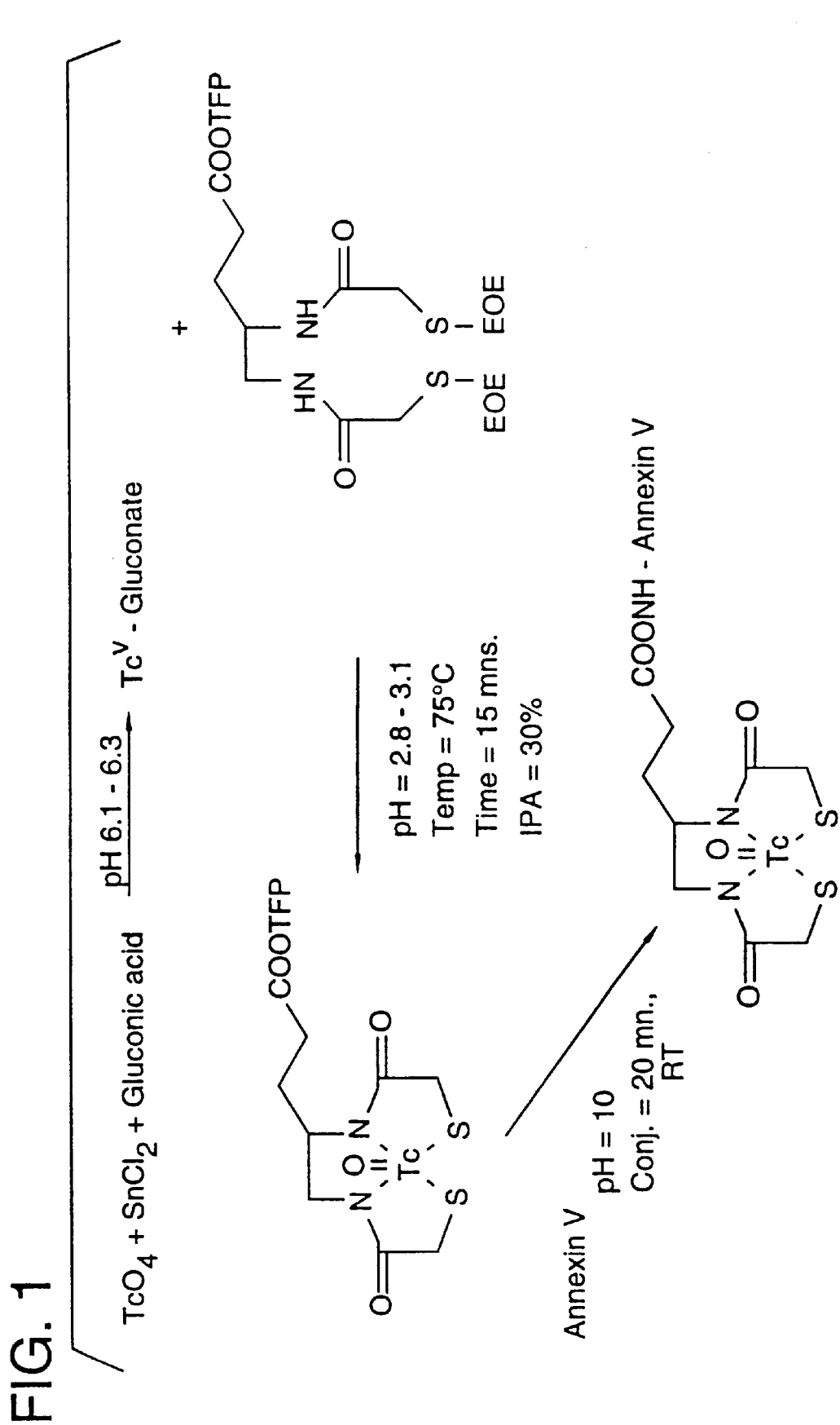
FIG. 1 schematically represents a method of radiolabeling annexin V.

Prior to setting forth the invention, it may be helpful to set forth definitions of certain terms to be used within the disclosure.

Annexin: A class of compounds characterized by the ability to bind with high affinity to membrane lipids in the presence of millimolar concentrations of calcium. Annexins have been shown to exhibit anti-coagulatory effects that are mediated by the binding of annexins to negatively charged surface phospholipids (e.g., on activated platelets). This annexin-phospholipid binding is believed to block the activation of clotting factors by such negatively charged surface phospholipids. Prior to the recognition of the annexin class of molecules, members thereof were also referred to in the literature as placental anticoagulant proteins (e.g., PAP-1, 2, 3 and 4), lipocortins, calpactins, vascular anti-coagulant (alpha and beta), calphobindin I, placental protein 4 (PP4), endonexin II, anchorin CII, calcium-dependent phospholipid binding protein, and the like. See Crumpton et al., *Nature* 345:212, 1990. Annexin-V is a prototypical annexin molecule used in the description of the present invention. The term annexin includes native annexin purified from natural sources such as e.g. human placenta, or annexin molecules containing a native sequence produced through e.g. genetic engineering, recombinant, or other means. The term annexin further includes modified annexins as defined below, derived from or produced by any source.

Modified Annexin: An annexin molecule wherein the native sequence or molecule is altered in such a way without materially altering the membrane binding affinity of the annexin. Such annexins can be produced by chemical, genetic engineering or recombinant techniques as know to those of ordinary skill in the art. The modification can include a modification of the sequence through the addition of several amino acid residues, and/or an addition/deletion of an amino acid at a single site on the native or genetically engineered sequence. For example, the annexin can be modified at the N-terminus by the addition of amino acid residues, wherein at least one of the amino acids provides an accessible sulfhydryl group. The accessible sulfhydryl group or groups may be utilized during conjugation or remain available for further conjugation. The term modified annexin includes annexin multimers.

Annexin Multimer: A combination of two or more monomeric modified annexin molecules of which the components of the multimer may be native or recombinant, or in any combination thereof; resulting in similar or improved membrane binding affinity over the monomeric annexin. A multimer composed of up to about 20 modified annexins is useful for the present invention. The preferred multimer composition is between 2 and about 10 modified annexins. One example of an annexin multimer is an annexin dimer, which can be composed of two modified annexins linked by disulfide bonds between accessible sulfhydryl groups on the modified annexins. The annexin dimer can be produced directly as a fusion protein using known expression systems, wherein the two annexin molecules can be connected by a peptide linker through the accessible sulfhydryl groups. A dimeric molecule could contain additional functional sites, such as an endogenous radiolabel chelation site or an accessible sulfhydryl group for the attachment of one or more hexose residues, for example. Also, as defined herein, annexin multimer is covered by the term annexin.

Extension: A series of amino acids added to the N-terminus of the annexin molecule which provides a sulfhydryl group within ten amino acids from the N-terminus. Preferably the sulfhydryl group is within six amino acids of the N-terminus. More preferably the sulfhydryl group is the second residue in the N-terminal extension of six amino acids. The sulfhydryl group is preferably provided by a cysteine residue. This addition of amino acids provides a highly flexible means to attach functional moieties to the annexin terminal region.

$N_xS_y$ Chelating Compounds: As defined herein, the term "$N_xS_y$ chelating compound" includes bifunctional chelators that are capable of (i) coordinately binding a metal or radiometal and (ii) covalently attaching to an annexin molecule. Preferred $N_xS_y$ chelating compounds have the $N_2S_2$ (generally described in U.S. Pat. Nos. 4,897,225 or 5,164,176 or 5,120,526), $N_3S$ (generally described in U.S. Pat. No. 4,965,392), $N_2S_3$ (generally described in U.S. Pat. No. 4,988,496), $N_2S_4$ (generally described in U.S. Pat. No. 4,988,496), $N_3S_3$ (generally described in U.S. Pat. No. 5,075,099) or $N_4$ (generally described in U.S. Pat. Nos. 4,963,688 and 5,227,474) cores. Particularly preferred $N_xS_y$ chelating compounds have $N_2S_2$ and $N_3S$ cores. Exemplary $N_xS_y$ chelating compounds are described in Fritzberg et al., Proc. Natl. Acad. Sci. USA 85:4024–29, 1988; in Weber et al., Bioconj. Chem. 1:431–37, 1990; and in the references cited therein, for instance. For the purpose of this description, the prototypical $N_xS_y$ chelating compound is an $N_2S_2$ chelating compound. A chelating compound which complexes a metal or radiometal is termed a "chelate".

Esterase-sensitive Chelating Compound: Amide thiolate acetate ester chelating compounds of the $N_xS_y$ family wherein the esterase-sensitive chelating compound connects the radionuclide metal to the annexin. As defined herein, the term "esterase-sensitive chelating compounds" includes those described in U.S. Pat. Nos. 5,112,953 and 5,175,257. The esterase-sensitive chelating compounds is cleaved during the metabolism of the radiolabeled protein in the liver to generate radioactivity associated catabolites of favorable redistribution, resulting in the reduction of background radioactivity adjacent to the heart and lungs. A preferred esterase-sensitive chelating compound is $N_3S$-serylsuccinate as described in U.S. Pat. No. 5,112,953.

Radiolabeled Annexin: An annexin having a radionuclide complexed therein.

Radiolabeled Annexin-Galactose: A galactose-derivatized annexin having a radionuclide complexed therein.

Hexose moiety: a composition of one or more six carbon sugar (hexose) residues, or derivatives based upon such moieties recognized by Ashwell receptors or other liver receptors, such as the mannose/N-acetylglucosamine receptor, which are associated with endothelial cells and/or Kupffer cells of the liver, or by the mannose 6-phosphate receptor. A hexose moiety includes a hexose cluster. A hexose moiety also includes more than one hexose moiety conjugated at separate sites to another molecule such as annexin.

Hexose Cluster: A construct having a plurality of hexose residues (including derivatives) configured to be recognized by a liver receptor. Such clusters are preferably constructed of hexose residues connected in a branched configuration (via a linking moiety, which in turn is connected to a branching structure), and are attached to annexin or to other components of a hexose cluster containing conjugate via a single point of attachment(through a linking moiety). Preferably, the branching network consists of two or three pronged branches, i.e., consists of 2, 4, 8, 16, 32 or 64 hexose residues or consists of 3, 9, 27, or 81 hexose residues.

Galactose Cluster: A construct having from about 3 to about 64 galactose residues connected in a branched configuration. Preferably, the branching network consists of two or three pronged branches, i.e., consists of 2, 4, 8, 16, 32 or 64 galactose residues or consists of 3, 9, 27, or 81 galactose residues.

Radiolabeled Annexin-Galactose Cluster: A galactose cluster-derivatized annexin having a radionuclide complexed therein.

Conjugate: A conjugate encompasses chemical conjugates (covalently or non-covalently bound), fusion proteins and the like.

Cleavable Linker: A bifunctional linker recognized by liver enzymes in such a way that the linker is enzymatically cleavable to produce a hydrophilic catabolite. In some preferred embodiments of the present invention, the cleavable linker connects the chelating compound to the hexose moiety. The cleavable linker functions for enhancement of renal excretion and hepatobiliary excretion so as to increase target to background ratio enabling early detection of atrial and venous thrombi. Examples of this type of linker includes a polymer, such as monosaccharides, polysaccharides, polyamino acids, hydroxyalkyl acrylamides, polyethylene glycol based hydrophilic polymers, biodegradable polymers containing an ether or ester linkage, as well as dextran and hemisuccinyl esters.

It will be evident to one of ordinary skill in the art that the references throughout the application to annexin includes modified annexin, as well as annexin multimer, unless otherwise specified or apparent from the context. One of ordinary skill in the art will also understand that, although galactose is described below as a representative example, any reference to galactose includes other hexose moieties, such as N-acetylgalactosamine and clusters thereof.

The present invention is directed to annexin-hexose containing conjugates, and radiolabeled annexins, including radiolabeled annexin-galactose cluster conjugates, and the use thereof for diagnostic imaging purposes. Radiolabeled annexins of the present invention are characterized by the following: rapid accretion to target cell sites characterized by anionic phospholipids; short circulating half-life; in vivo stability against metabolic degradation or radionuclide separation from chelate; and amenability to packaging in cold kit format.

Radiolabeled annexin-galactose conjugates also exhibit the aforementioned characteristics, albeit to different degrees. For example, radiolabeled annexin-galactose conjugates exhibit a shorter circulating half-life than their radiolabeled annexin counterparts. Also, radiolabeled annexin-galactose conjugates generally exhibit a lower binding affinity for target sites than their radiolabeled annexin counterparts. Successful diagnostic imaging involves both target site accumulation of signal and rapid elimination of non-targeted signal. Consequently, the enhanced elimination from a recipient's circulation of the radiolabeled annexin galactose conjugates provides a distinct opportunity to achieve diagnostic images in a shorter time frame.

Moreover, target site signal diminishes over time as a result of radioactive decay. In addition, metabolism of the target associated material also diminishes target signal. Consequently, shorter time frame imaging enhances the target:non-target ratio and total target signal, thereby garnering improved diagnostic information.

Radiolabeled annexin-galactose cluster conjugates of the present invention combine desirable features of radiolabeled annexins and radiolabeled annexin-galactose conjugates. For example, radiolabeled annexin-galactose cluster conjugates exhibit a shorter circulating half-life than their radiolabeled annexin counterparts. Also, radiolabeled annexin-galactose cluster conjugates generally exhibit a higher binding affinity for target sites than their radiolabeled annexin-galactose conjugate counterparts. Consequently, the enhanced elimination from a recipient's circulation and the substantial binding affinity maintenance of the radiolabeled-annexin-galactose cluster conjugates of the present invention invention offer the opportunity to achieve clear diagnostic images in a shorter time frame.

An embodiment of the present invention is directed to annexin-containing conjugates suitable for radiolabeling with a diagnostic imaging agent including:

an annexin;

a hexose moiety; and an $N_xS_y$ chelating compound associated with the annexin.

Radiolabeled annexin-galactose cluster conjugates suitable for imaging vascular thrombi anywhere in the recipient (but particularly in or near the heart) are also contemplated, which radiolabeled annexin-galactose cluster conjugates incorporate an annexin, a cluster of galactose residues, an $N_xS_y$ chelating compound, and further a diagnostic radionuclide completed by the chelating compound.

A preferred embodiment of the present invention involves annexin-containing conjugates suitable for radiolabeling with a diagnostic imaging agent including:

an annexin;

a cluster of galactose residues; and an $N_2S_2$ chelating compound associated with the annexin.

Radiolabeled annexin-galactose cluster conjugates suitable for imaging vascular thrombi are also contemplated, which radiolabeled annexin-galactose conjugates incorporate an annexin, a cluster of galactose residues, an $N_2S_2$ chelating compound, and further a diagnostic radionuclide complexed by the chelating compound.

Another preferred conjugate of the present invention includes:

a modified annexin, wherein the modification provides an accessible sulfhydryl group; and a hexose moiety recognized by a mammalian liver receptor, wherein the hexose moiety is conjugated to the annexin.

Radiolabeled modified annexin-hexose moiety conjugates suitable for imaging vascular thrombi are also contemplated, which radiolabeled annexin-hexose moiety conjugates incorporate a modified annexin, a hexose moiety, and further a diagnostic radionuclide conjugated to the modified annexin.

Another preferred conjugate of the present invention includes:

a modified annexin, wherein the modification provides an accessible sulfhydryl group;

a hexose moiety recognized by a mammalian liver receptor; and a $N_xS_y$ chelating compound, wherein the hexose moiety is conjugated to the modified annexin directly or via the chelating compound is conjugated to the modified annexin directly or via the hexose moiety.

Radiolabeled modified annexin-hexose moiety conjugates suitable for imaging vascular thrombi are also contemplated, which radiolabeled modified annexin-hexose moiety conjugates incorporate a modified annexin, a hexose moiety, an $N_xS_y$ chelating compound and further a diagnostic radionuclide complexed by the chelating compound.

Another preferred conjugate of the present invention includes:

an annexin multimer;

a hexose moiety recognized by a mammalian liver receptor; and an $N_xS_y$ chelating compound, wherein the hexose moiety is conjugated to the multimer directly or via the chelating compound and the chelating compound is conjugated to the multimer directly or via the hexose moiety.

Radiolabeled annexin multimer conjugates suitable for imaging vascular thrombi are also contemplated, which radiolabeled annexin multimer conjugates incorporate an annexin multimer, a hexose moiety, an $N_xS_y$ chelating compound, and further a diagnostic radionuclide complexed by the chelating compound.

Another preferred annexin conjugate of the present invention is those suitable for radiolabeling with a diagnostic imaging agent including:

an annexin; and an esterase-sensitive $N_xS_y$ chelating compound conjugated to the annexin.

Radiolabeled annexin conjugates suitable for imaging vascular thrombi are also contemplated, which radiolabled annexin conjugates incorporate an annexin, an esterase-sensitive $N_xS_y$ chelating compound and further a hexose moiety and a diagnostic radionuclide complexed by the chelating compound.

Another preferred conjugate of the present invention includes:

a modified annexin, wherein the modification provides acessible sulfhydryl group; and a $N_xS_y$ chelating compound conjugated to the annexin.

Radiolabeled modified annexin conjugates suitable for imaging vascular thrombi are also contemplated, which radiolabled modified annexin conjugates incorporate a modified annexin, an $N_xS_y$ chelating compound and further a diagnostic radionuclide completed by the chelating compound.

Another preferred conjugate of the present invention includes:

a modified annexin, wherein the modification provides an accessible sulfhydrl group; and an esterase-sensitive $N_xS_y$ chelating compound conjugated to the annexin.

Radiolabeled annexin conjugates suitable for imaging vascular thrombi are also contemplated, which radiolabled annexin conjugates incorporate an annexin, an esterase-sensitive $N_xS_y$ chelating compound, and further a diagnostic radionuclide completed by the chelating compound.

Another preferred conjugate of the present invention includes:

an annexin multimer; and a $N_xS_y$ chelating compound conjugated to the annexin. Radiolabeled annexin multimer conjugates suitable for imaging vascular thrombi are also contemplated, which radiolabeled annexin multimer conjugates incorporate an annexin multimer, an $N_xS_y$ chelating compound, and further a diagnostic radionuclide complexed by the chelating compound.

Another preferred conjugate of the present invention includes:

an annexin multimer; and an esterase-sensitive $N_xS_y$ chelating compound conjugated to the annexin.

Radiolabeled annexin multimer conjugates suitable for imaging vascular thrombi are also contemplated, which radiolabeled annexin multimer conjugates incorporate an annexin multimer, an esterase-sensitive $N_xS_y$ chelating compound, and further a diagnostic radionuclide complexed by the chelating compound.

It will be evident to one of ordinary skill in the art, that where a conjugate of the present invention has three components (e.g., an annexin, a hexose moiety, and chelating compound), a component my be bonded to one another in a variety of orientations. For example, the hexose moiety and a chelating compound my be bonded at different sites on an annexin, or bonded to one another and only one is bonded to the annexin directly.

For the visualization of vascular thrombi associated with a number of pathological conditions, a radiolabeled annexin such as a conjugate of an annexin with a chelating compound complexed with an imaging radionuclide, such as Tc-99m for example, is administered to a recipient for whom such a diagnosis is desired. The radiolabeled annexin or annexin portion of the radiolabeled conjugate localizes rapidly to target sites characterized by negatively charged surface phospholipids, such as vascular thrombi. The radionuclide is selected for its ability to be visualized via one of the various techniques therefor, e.g., gamma camera imaging. Because of the rapid accretion of annexins to the target site and the short serum half-life (generally less than 30 minutes) of annexins (which is not significantly lengthened upon radiolabeling), imaging of those target sites proceeds with little exposure of non-target sites to radioactivity.

Diagnostic imaging is dependent on signal-to-noise ratio. Improvements involving either target signal accumulation or noise reduction will enhance the efficacy of the diagnostic imaging product. For targeted imaging, noise reduction is synonymous with reducing background radioactivity, particularly blood pool activity. Annexins, including annexin V, are rapidly removed by the liver; however, only a fraction of the activity is removed with each pass of the circulating conjugate through the liver.

To more efficiently remove the background activity from the blood, an improvement in liver extraction of annexin-containing conjugates could be employed. A preferred method to enhance liver extraction involves derivatizing the annexin-containing conjugate with a hexose moiety, such as galactose, that is recognized by a liver receptor. The efficiency of liver receptor extraction of the moiety recognized thereby will result in increased "per pass" removal by the liver of derivatized annexin-containing conjugate (e.g., annexin-galactose conjugate) in comparison to the amount of underivatized annexin-containing conjugate so removed.

Further improvement in signal-to-noise ratio can be achieved by derivatizing radiolabeled annexin or an annexin-containing radiolabeled conjugate with a cluster of galactose molecules recognized by a liver receptor. The efficiency of liver receptor extraction of the moiety recognized thereby will result in increased "per pass" removal by the liver of derivatized annexin-containing conjugate (e.g., annexin-galactose cluster conjugate) in comparison to the amount of underivatized annexin-containing conjugate so removed. In addition, the multiple galactose residues arranged in a cluster are bound to the annexin conjugate component via a single point of attachment. Consequently, less or no reduction in annexin target binding affinity resulting from galactose cluster derivatization may be achieved in comparison to annexin-galactose conjugates.

Annexins are generally (with the most notable exception being annexin II) single chain, non-glycosylated proteins of approximately 33–72 kilodalton molecular weight. Annexins possess a number of biological activities associated with calcium ion-mediated binding.

Investigations have shown that annexins bind with high affinity to anionic membrane lipids in the presence of millimolar concentrations of calcium. In the presence of calcium, these proteins have an especially high affinity for negatively charged phospholipids, such as phosphatidylserine, phosphatidylglycerol, phosphatidic acid, or phosphatidylinositol. See, for example, Funakoshi et al., Biochem. 26: 5572–78, 1987; and Tait et al., Biochem. 27: 6268–76, 1988. Such negatively charged phospholipids are associated with vascular thrombi (e.g., are located on the surface of activated human platelets).

Annexins exert anti-coagulatory effects. Coagulation inhibition is mediated by the binding of annexins to negatively charged surface phospholipids (e.g., present on the surface of activated platelets). This binding is believed to block the activation of clotting factors by such negatively charged surface phospholipids. Annexins localize to target sites bearing anionic phospholipids rapidly, i.e., in a matter of approximately 5 to 30 minutes depending on circulating levels thereof, but remain circulating in the serum for a somewhat longer time period (circulating half-life <30 minutes). Example III below discusses results of imaging experiments wherein vascular thrombi were visualized in planar images at an average time (following annexin administration) of 82 minutes. Because of these properties, annexins or annexins conjugated to diagnostic or therapeutic agents may be employed in protocols for the in vivo diagnosis or treatment of vascular thrombi associated with a number of indications, such as DVT (deep vein thrombosis), PE (pulmonary embolism), myocardial infarction, atrial fibrillation, problems with prosthetic cardiovascular materials, stroke and the like. Other indications associated with accumulation of activated platelets, for which the annexin conjugates of the present invention are useful, include the following: abscess imaging, restenosis post balloon angioplasty (PCTA), inflammation of joints (i.e., Rheumatoid arthritis), damaged endothelial cells (i.e., Alzheimer's disease), imaging of clots in cerebral arteries, occlusions in peripheral arteries, atrial thrombosis imaging, and imaging of coronary and carotid artery thrombi.

It is also important to characterize platelet populations in clinical, in vitro diagnostic, and basic research disciplines. Of the cell surface markers currently available to characterize platelets, many are not cross-reactive between species and may recognize all platelets as opposed to just the activated platelet population. It is believed that annexin selectively binds to activated platelets in many species. Thus annexin conjugates of the invention can be utilized as an alternative cell marker in research and diagnostics disciplines such as immunohistochemistry and flow cytometry. For example, conjugates of the present invention can be used to detect activated platelets in fixed tissues/tumors, blood smears, in animals with coagulopathies, and in situ in platelet activation assays in response to various chemical or infectious stimuli as well as to detect activated platelets in blood, cell culture assays and platelet response assays. It will be appreciated by one of ordinary skill in the art that the conjugates of the present invention are useful for any purpose or indication, in which the targeting or binding of activated platelets would be desirable. Exemplary diagnostic protocols and experimentation employing radiolabeled annexins are set forth below to further elucidate this aspect of the present invention.

An example of a preferred annexin useful in the practice of the present invention is Annexin V, which was isolated by Bohn in 1979 from human placenta, a rich source of annexins, and termed Placenta Protein 4 (PP4). Annexin V has been expressed in *E. coli*, Iwasaki et al., *J. Biochem.*, Vol 102, No.5, 1261–1273 (1987). Also, a full length cDNA clone of annexin V has been obtained and subcloned in expression vectors, thereby facilitating the production of fusion proteins containing annexin V (see generally, Tait et al., *J. Biol. Chem*, Vol. 270, No. 37, pp 21594–21599 (1995). Annexin V consists of four domains (four tandem, imperfect repeats of about 75 amino acid residues, Funakoshi et al., *Biochem.*, 26: 8087–92, 1987), wherein each domain is made up of 5 alpha helices. From the side, the annexin V molecule appears crown-like with at least four calcium binding sites on its convex surface, through which annexin-phospholipid interactions are mediated. Other annexin molecules are also useful in the practice of the present invention, and the discussions relating to annexin V herein apply generally to annexin molecules.

Because annexin V has a plurality of calcium binding sites, and because annexin V binding to negatively charged phospholipids is mediated by calcium, an engineered molecule consisting of one or more individual annexin V domains may be employed in imaging protocols of the present invention. Also, the annexin molecule may be partitioned at a position or positions different from the domain boundaries to provide an engineered molecule capable of calcium-mediated binding of anionic phospholipids. Also, annexin V may be altered at one or more amino acid residues, so long as the affinity of annexin V for anionic phospholipids is not significantly impaired. For example, the cysteine (position 316) amino acid residue of annexin V can be either deleted or replaced with alanine or other non-sulfur containing amino acids known to those of ordinary skill in the art; wherein, upon labeling, a monomerically radiolabeled annexin V is produced.

In another example, a native annexin can be modified at the N-terminus by adding amino acid residues to provide for an accessible sulfhydryl group or groups. This can be accomplished with the addition of at least a single cysteine residue near the N-terminus. The accessible sulfhydryl groups may be available after initial conjugation or is for further conjugation depending on the embodiment of the invention utilized.

A preferred modified annexin molecule, as defined herein, is a monomeric form of annexin V with an N-terminal extension of an amino acid sequence, wherein the sequence is selected so that it contains amino acids adjacent to an amino acid countacy an accesible sulfhydryl group cysteine. The selected sequence will improve target to normal organ ratios and superior clot imaging potential. The use of hydrophilic amino acids, in the sequence such as serine, glycine, theonine, aspartate, glutamate and others facilitates renal excretion of chelate products of catabolism following uptake of the radiolabeled annexin in normal organs, such as the liver. One preferred amino acid sequence added to at the N-terminus of annexin V is Ala-Cys-Asp-His-Ser-Met (SEQ ID NO:1). An advantage of this particular configuration is that with the cysteine near the N-terminus, the sulfhydryl and neighboring amide groups provide for stable chelation of the technetium resulting in an $N_3S$-like stable chelate, as in endogenous radiolabeling of the annexin molecule.

Other model peptides that vary the sequence at the N-terminus of modified annexin V (for example, the sequence of George et al. in *Proc. Natl. Acad. Sci. USA*, 92:8358–62, 1995) can be prepared. These peptides are subjected to the same conditions of in vitro labeling with Tc-99m as described above. Peptides with suitable labeling characteristics can be chosen, and the sequence can be engineered into the recombinant annexin V molecule. Success is indicated by preparation of a derivative with specific activity as high or higher than the current derivative as reported by Stratton et al, in *Circulation*, 92: 3113–3121, 1995; that is stable in vitro and in vivo; that retains membrane and thrombus binding activity; and that is not adversely altered with respect to blood clearance or biodistribution. If the above-identified criteria is met, the modified Annexin V molecule or dimer of the modified annexin V molecule is used according to the invention.

An annexin multimer composed of two or more modified annexin molecules which are limited by disulfide bonds between one or more of the accessible sulfhydryl groups on the respective annexins. A preferred annexin multimer, is an annexin dimer. A prototypical annexin multimer is an annexin dimer. The dimer is intended to have a higher affinity for the platelet membrane resulting from a slower dissociation rate. The dimer can then be accreted to a higher level or retained longer in the thrombus in vivo, thus improving the target-to-background ratio at any given time. The annexin multimer, as well as the annexin dimer can be produced as a fusion protein using known expression systems with the modified annexins connected by a peptide linker through the accessible sulfhydryl groups. A multimeric molecule can also contain additional functional sites, such as an endogenous radiolabeled chelation site or a free sulfhydryl to allow for attachment of a hexose moiety. Where an annexin dimer is produced and includes a hexose moiety and a chelating compound, this dimer can then be used for generating stabilized monomers for further radiolabeling procedures via reduction of the disulfide bonds of the dimer.

The degree of annexin binding to phospholipids may be quantified by fluorescence quenching as described by Tait et al., *J. Biol. Chem.*, 264: 7944–49, 1989.

Among annexins, annexin V has the strongest binding affinity ($K_d < 10^{-10}$M) for phospholipid vesicles containing 80% phosphatidylcholine and 20% phosphatidylserine under conditions comparable to plasma and extracellular fluid (1.2 mM ionized calcium, 0.15M ionic strength). This binding is reversible and calcium dependent.

To decrease the background radiolabel activity, annexins (including modified annexins) may be derivatized with hexose moieties or hexose-based moieties. More specifically, annexins may be derivatized to incorporate one or more hexoses (e.g. six carbon sugar moieties) recognized by Ashwell receptors or other liver receptors, such as the mannose/N-acetylglucosamine receptor, which are associated with endothelial cells and/or Kupffer cells of the liver, or by the mannose 6-phosphate receptor. Exemplary of such hexoses are galactose, mannose, mannose 6-phosphate, N-acetylglucosamine, pentamannosyl phosphate, and the like. Other moieties recognized by Ashwell receptors, including glucose, N-galactosamine, N-acetylgalactosamine, thioglycosides of galactose and, generally, D-galactosides and glucosides and the like, may also be used in the practice of the present invention. Thus, hexose moieties useful in the practice of the present invention include a variety of galactose, mannose and glucose sugars recognized by liver receptors. Preferred hexose moieties are hexose sugars, such as galactose and galactose clusters. It should be understood that galactose and galactose clusters are encompassed by the term hexose moiety. It should also be recognized that the use of the term galactose in the discussion is understood to encompass not only galactose, but N-galactosamine, N-acetylgalactosamine, thioglycosides of galactose and generally, D-galactosides as well; the term mannose is understood to encompass mannose, mannose -6-phosphate, pentamannosyl phosphate, and the like; the term glucose, is understood to encompass glucose, glucosides, and the like. For purposes of the invention the most preferred galactose is N-acetylgalactosamine.

Galactose is the prototypical hexose employed for the purposes of this description. Galactose thioglycoside conjugation to a protein is preferably accomplished in accordance with the teachings of Lee et al., "2-Imino-2-methoxyethyl 1-Thioglycosides: New Reagents for Attaching Sugars to Proteins," *Biochemistry*, 15(18): 3956, 1976. Another useful galactose thioglycoside conjugation method is set forth in Drantz et al, "Attachment of Thioglycosides to Proteins: Enhancement of Liver Membrane Binding," *Biochemistry*, 15(18): 3963, 1976. Annexin-galactose conjugation is also discussed in the Examples set forth herein.

Hexose moiety conjugation to the annexin via chemical methods can occur either prior to (post-formed approach) or following (pre-formed approach) conjugation of the chelating compound to the annexin. Hexose moiety chemical conjugation is preferably conducted prior to chelating compound conjugation, however.

The number of galactose residues on the product conjugates will range from 1 to the maximum number of galactoses that do not significantly diminish the binding affinity of annexin for its target, see Example IV. For example, galactose derivatization that preserves at least 20%. of native annexin binding activity is preferred, with the preservation of at least 50% of native annexin binding activity more preferred. The theoretically possible maximum number of galactose residues located on the annexin molecule is 22 (i.e., the number of lysine residues within the annexin structure). An exemplary number of galactose residues on radiolabeled annexin-galactose conjugates of the present invention ranges between 1 and about 5.

Hexose clusters are preferably employed in the practice of the present invention. Galactose clusters are the prototypical hexose clusters employed for the purposes of this description. A cluster containing the galactose, N-aceylgalactosamine, is a preferred galactose clusters of the present invention. Design of hexose clusters of the present invention is conducted with the following criteria in mind, as set forth in the context of the design of a galactose cluster:

1) Number of Galactoses in a Cluster;
2) Distance Between Galactoses in the Cluster; and
3) Distance Between Galactose Cluster and the Annexin Conjugate Component.

With regard to criteria number 1, literature indicates that galactose receptors on the surface of human hepatocytes are grouped as heterotrimers and, perhaps, bis-heterotrimers. See, for example, Hardy et al., *Biochemistry*, 24: 22–8, 1985. For optimal affinity to such receptors, it is contemplated within the present invention that each galactose cluster should preferably contain at least three galactose residues. In general, the greater the number of galactose residues in a cluster, the greater the propensity for the cluster to be recognized by liver receptors.

Increased galactose cluster size may impair annexin binding to target. If significant impairment in annexin binding to target (e.g. reduction to <20% of native annexin binding) is observed, a longer linker between the two moieties may be used or such large clusters should not be employed in radiolabeled annexin-galactose cluster conjugates of the present invention.

With respect to criteria number 2, the galactose receptors within each trimer are separated from each other by distances of 15, 22 and 25 angstroms. Consequently, it is contemplated within the present invention that the galactoses within a cluster should preferably be separated by flexible linkers allowing separation of at least 25 angstroms. The spacing between galactose residues is likely to be more important if the number of galactose residues is small. With larger constructs, appropriate spacing is likely to occur with respect to galactose residues that are not immediate neighbors (i.e., sugar residues that are farther apart than those that are immediate neighbor). Assuming an average bond length of 1.5 angstroms, preferred galactose clusters of the present invention are characterized by separation of neighboring galactose residues by about 10 bond lengths or more. Other preferred constructs involve galactose clusters characterized by separation of neighboring sugar residues by about 25 bond lengths or more.

Regarding criteria number 3, the distance between the annexin and the galactose cluster should be sufficient to obviate any adverse steric effects upon annexin binding to target caused by the size or orientation of the galactose cluster. This distance is preferably greater than about 7 bond lengths or about 10 angstroms. If necessary, an extender molecule is incorporated between the galactose cluster and the linker (which joins the galactose cluster and the annexin component) or between the annexin and the linker to provide the requisite distance.

While the foregoing parameters appear to be optimal for galactose, it should be noted that these factors may vary with other hexoses or mixtures thereof, which may or may not bind to the same receptors, or may bind differently. Given the teachings in this application, one of ordinary skill in the art can, using available synthesis techniques, attach an annexin and an active agent to other hexose clusters and identify those constructs which provide optimal performance.

Any branched sugar structures that meet the criteria described above may be employed in the practice of the present invention. Preferred galactose clusters of the present invention are of the following structures:

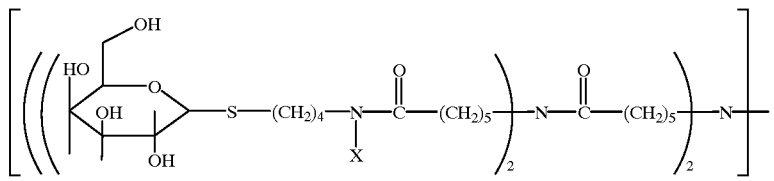
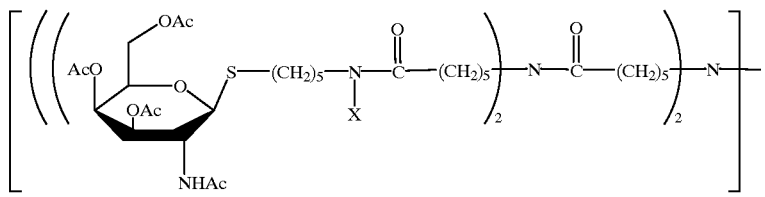
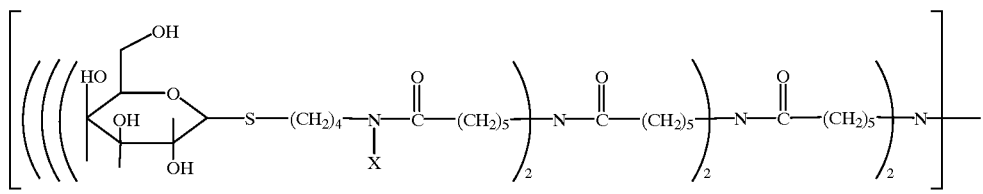
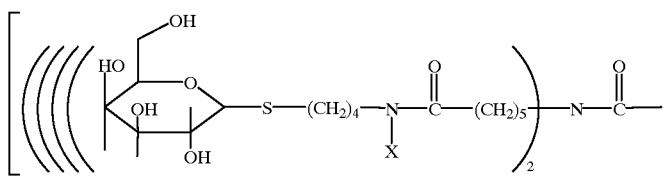
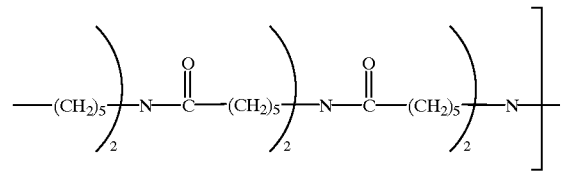
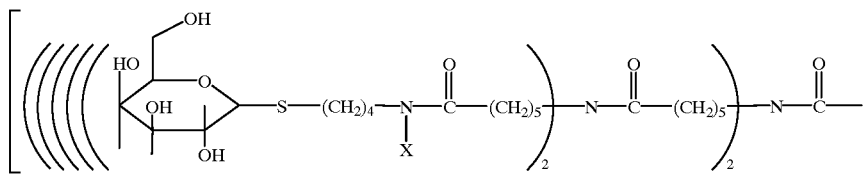
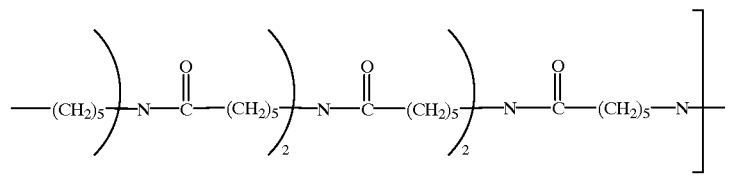
wherein X is preferably H or methyl, resulting in galactose clusters bearing 4, 8, 16 and 32 galactose residues, respectively. Further iteration in the branching scheme allows expansion of the galactose cluster to include 32, 64, etc.

galactose residues. In addition, the linker moiety between the hexose itself and the branching structure (shown as —S—(CH$_2$)$_4$—NX—) may be variable in length.

Alternative branching structures may also be employed in the design of galactose clusters in accordance with the present invention. For example, other constructs wherein the branching results in a doubling of the number of galactose residues may be employed. In addition, constructs wherein branching results in a tripling or other convenient multiplying of the number of galactose residues are also contemplated by the present invention.

Another potential branching construction is based upon the molecule bis-homotris: (HO—CH$_2$)$_3$—C—NH$_2$. The sulfhydryl-containing derivative of this molecule may also be used. In this embodiment of the present invention, each arm of the bis-homotris molecule is extended and terminated in a carboxylic acid: (HO$_2$C—(CH$_2$)$_y$—Z—(CH$_2$)$_3$—C—NH$_2$), where Z is S or O and y ranges from 1 to about 10. For this embodiment of the present invention, a preferred galactose cluster is characterized by the following structures:

ing moiety will generally not be "suitable" for conjugation, because the targeting ability of the antibody is likely to be substantially impaired by such binding.

Useful trifunctional linkers are amenable to binding with functional groups available on the three conjugate components or any extender moieties employed in conjugate construction. A useful trifunctional linker is lysine, wherein the alpha-amino, epsilon-amino and carboxyl functional groups are used. One of ordinary skill in art the could identify other trifunctional linkers and use the same in the practice of the present invention as set forth herein.

The following variations for the order of component (specifically the modified annexin, hexose moiety and chelating compound) conjugation, are contemplated within the present invention:

the hexose moiety conjugated to the modified annexin, through an accessible sulfhydryl group or groups, and the chelating compound conjugated to the modified annexin through a lysine residue on the modified annexin; a chelating compound conjugated to the modified annexin, through accessible sulfhydryl group or

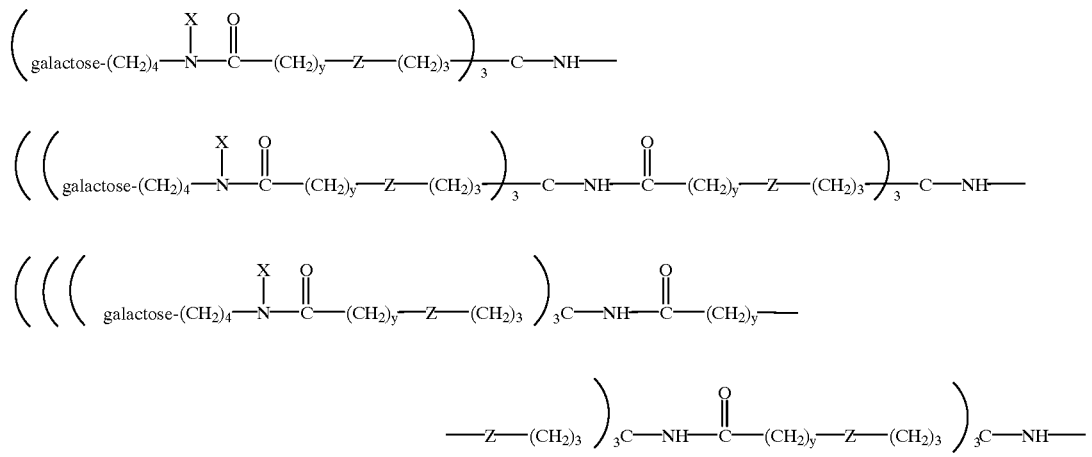

wherein X is preferably H or methyl; y ranges from 1 to about 10; and Z is O or S. The above structures bear 3, 9 and 27 galactose residues, respectively. Further iteration of the branching allows expansion to include 81, etc. galactose residues.

Also, X may be a lower alkyl moiety (composed of two to twelve carbons) different from methyl, such as ethyl, t-butyl and the like. X may also be a lower alkyl group bearing a heteroatom, such as a lower alkyl acid, ester, aldehyde, ketone or ether.

In embodiments of the present invention wherein the chelating compound is characterized by a single functional group available and suitable for conjugation, the annexin, chelating compound and galactose cluster components are preferably joined via a trifunctional linker. Functional groups that are "available" for conjugation are those that are not prevented by steric constraints from conjugate formation. Functional groups that are "suitable" for conjugation are those that are capable, in a chemical sense, of reacting with available functional groups associated with other conjugate components. In addition, conjugation of "suitable" functional groups does not substantially impair a necessary function of the component with which the functional group is associated. For example, a functional group located in the complementarity determining region of an antibody target-groups, and the hexose moiety conjugated to the modified annexin through a lysine residue on the modified annexin; chelating compound conjugated to hexose moiety, which in turn is conjugated to the modified annexin through accessible sulfhydryl group or groups; the hexose moiety conjugated to the chelating compound, which in turn is conjugated to the modified annexin through accessible sulfhydryl groups; chelating compound conjugated to the hexose moiety which in turn is conjugated to the modified annexin through the lysine residues of the modified annexin, thus leaving the accessible sulfhydryl groups available for further conjugation; hexose moiety conjugated to chelating compound which in turn is conjugated to the modified annexin through lysine residues, again leaving the accessible sulfhydryl groups available for further conjugation; and other like variations.

Cleavable linkers may be employed in the present invention. Such linkers are bifunctional moieties capable of binding with the trifunctional linker in such a way as to connect the chelating compound to the trifunctional linker, which in turn is connected to the annexin component and cluster component. Examples of suitable cleavable linkers include monosaccharides, polysaccharides, polyamino acids, hydroxyalkyl acrylamides (e.g. HPMA), polyethylene glycol based hydrophilic polymers, biodegradable polymers which contain an ether or ester linkage, as well as dextran and hemisuccinyl esters, and the like.

Extender molecules useful in the present invention are bifunctional moieties capable of binding with either the annexin component and the linker or the galactose cluster component and the linker. Suitable extender molecules include aminocaproate moieties, HS—$(CH_2)_n$COOH or an activated ester form thereof wherein n ranges from 2 to about 5, and the like. One of ordinary skill in the art is capable of identifying and using other suitable extender molecules as described herein. Alternatively, the extender function can be served by an appropriately constructed linker.

Also, binding facilitation moieties may also be employed in the present invention. Such moieties are bifunctional and facilitate binding the conjugate components, e.g., galactose cluster, annexin, chelating compound, linker, and extender. Examples of such binding facilitation moieties include urea functionalities, thiourea functionalities, succinate bridges, maleimides and the like. Such binding facilitation moieties are amenable to identification and use by those of ordinary skill in the art.

An example of a linker-extender-binder facilitation system is shown below:

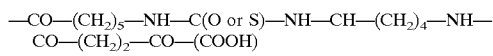

wherein the alpha-amine of the lysine linker is bound via a urea or thiourea functionality to an amino caproate spacer (which, in turn, binds to a galactose cluster that is not shown); the lysine carboxylate is available for linkage to a chelating compound (not shown); and the epsilon-amine of the lysine linker is available for linkage to a lysine residue of the annexin component (not shown) via a succinate bridge. Other amino acid residues of the annexin component, such as cysteine, may also be employed for binding purposes. Alternatively a maleimide-—S—$(CH_2)_n$ CO— binding facilitation moiety-extender combination may be employed to link the sugar residue with the lysine. An example of a conjugate joined by a trifunctional linker is discussed in Example VII.

When the chelating compound component of the conjugate is characterized by greater than one functional group available and suitable for conjugation, the galactose cluster may be linked to the chelating compound component which, in turn, is linked to the annexin component of the conjugate via two or more bifunctional linkers. Alternatively, the hexose cluster, such as N-acetylgalactosamine, is linked to the accessible sulfhydryl group of the modified annexin and the chelating compound component is linked to the annexin component via the lysine residue on the annexin. In another possible configuration, the chelating compound is linked to a hexose cluster through a trifunctional linker, wherein the hexose cluster conjugated to the chelating compound is then linked to the accessible sulfhydryl group of the modified annexin through a binding facilitation moiety. The above possible configuration can also include a cleavable linker between the chelating compound and the linker attaching the cluster to the annexin. Preferably, the annexin component of the conjugate is attached last in the formation of a galactose cluster-chelating compound-annexin conjugate. Suitable bifunctional linkers and linking methodologies can be identified and employed by one of ordinary skill in the art. An example of such a chelating compound and such a conjugation methodology is set forth in Example V.

Annexin V modified with a hexose moiety, such as a galactose cluster containing, for example, a N-acetylgalactosamine sugar, is intended to clear faster from the blood by the liver, allowing one to achieve optimal thrombus-to-background ratios soon after administration of radiolabeled agent. Attachment of the cluster near the N-terminus of the modified annexin intended to not affect the binding of the annexin moiety to thrombi.

Annexin conjugation to the hexose moiety and the chelating compound via chemical methods can occur either prior to (post-formed approach) or following (pre-formed approach) complexation of a radiometal with the chelating compound. In a preferred embodiment, a hexose moiety is attached to the annexin component prior to the addition of the radiolabel. The chemical conjugation is preferably conducted following radiometal complexation, unless the chelating compound employed in the conjugate is capable of binding the radionuclide with rapid kinetics at room temperature. Annexin V is radiolabeled with an imaging radionuclide for use in the present invention.

Radionuclides useful within the present invention include penetrating photon emitters including gamma-emitters and X-ray emitters. These rays accompany nuclear transformation such as electron capture, beta emission and isomeric transition. Radionuclides useful include those woth photons between 80 and 400 keV and positron producers, 511 keV annihilation photons and acceptable radiation dose due to absorbed photons, particles and half life. Radionuclides suitable for use in the present invention are known in the art and include $^{18}F$, $^{64}Cu$, $^{186}Re$, $^{188}Re$, $^{100}Pd$, $^{212}Bi$, $^{212}Pb$, $^{109}Pd$, $^{67}Cu$, $^{67}Ga$, $^{68}Ga$, $^{99m}Tc$, $^{94}Tc$, $^{95}Ru$, $^{105}Ru$, $^{99}Rh$, $^{105}Rh$, $^{111}In$, $^{123}I$, $^{125}I$, $^{153}Sm$, $^{177}Lu$, $^{170}Lu$, $^{189}Pt$, $^{193}Pt$, $^{199}Au$, $^{197}Hg$ and the like.

Tc-99m is a preferred radionuclide for the practice of the present invention. Tc-99m has been stably bound to annexin V in accordance with the present invention at both low and high specific activity (0.53 $\mu$Ci/$\mu$g–101.2 $\mu$Ci/$\mu$g). Adequate radiochemical yields and good radiochemical purities were obtained. Activated platelet binding studies were also conducted, and the radiolabeled annexin V conjugates bound to activated platelets well.

$N_xS_y$ chelating compounds include bifunctional chelating compounds that are capable of coordinately binding a metal or radiometal and covalently attaching to an annexin molecule. Preferred $N_xS_y$ chelating compounds have the $N_2S_2$ (generally described in U.S. Pat. Nos. 4,897,225 or 5,164,176 or 5,120,526), $N_3S$ (generally described in U.S. Pat. No. 4,965,392), $N_2S_3$ (generally described in U.S. Pat. No. 4,988,496), $N_2S_4$ (generally described in U.S. Pat. No. 4,988,496), $N_3S_3$ (generally described in U.S. Pat. No. 5,075,099) and $N_4$ (generally described in U.S. Pat. Nos. 4,963,688 and 5,227,474) cores. Particulary preferred $N_xS_y$ chelating compounds have the $N_2S_2$ and $N_3S$ cores. $N_2S_2$ and $N_3S$ chelating compounds are known in the art. For example, preferred $N_2S_2$ chelating compounds are described in U.S. Pat. No. 4,897,225, and preferred $N_3S$ chelating compounds are generally described in U.S. Pat. No. 4,965,392 and U.S. Pat. No. 5,112,953.

The $N_2S_2$ chelating compound are diamide, dimercaptide bifunctional chelators of the $N_xS_y$ family capable of stably complexing a radionuclide through two nitrogen atoms and two sulfur atoms that are appropriately positioned. $N_2S_2$ chelating compounds are generally described in U.S. Pat. No. 4,897,225.

Preferred chelating compounds with an $N_2S_2$ core also include diamine dimercaptide chelating compounds having the following biphenyl backbone, which are described in U.S. patent application Ser. No. 08/463,232:

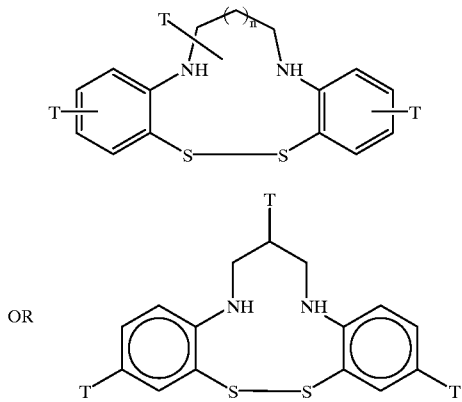

OR

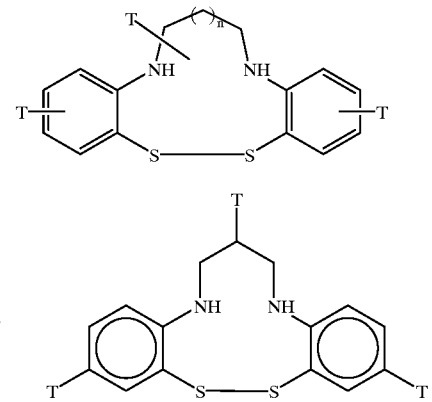

OR wherein n=0 to 1 and one or more T substituents incorporate a functional group available and suitable for conjugation with another conjugate component. Such exemplary functional groups include hydrophilic groups that are amenable for renal excretion as opposed to heptobiliary excretion.

The $N_3S$ chelating compounds are triamide, mercaptide bifunctional chelators of the $N_xS_y$ family capable of stably complexing a radionuclide through three nitrogen atoms and one sulfur atom that are appropriately positioned. Preferred $N_3S$ chelating compounds are described in U.S. Pat. Nos. 4,965,392 and 5,091,514.

The present invention applies this stable chelation technology to exploit the thrombus-targeting ability of annexin molecules, thereby providing an imaging agent which is able to rapidly visualize vascular thrombi in vivo. The radiolabeled annexins, including radiolabeled annexin-galactose conjugates and radiolabeled annexin-galactose cluster conjugates, of the present invention can be used to obtain thrombus images which reduce or eliminate the high level of background radioactivity that results from metabolically degraded radiolabeled conjugate. The radiolabeled annexins, including radiolabeled annexin-galactose conjugates and radiolabeled annexin-galactose cluster conjugates, also avoid clinically unacceptable toxicity to non-target cell sites. Tc-99m radiolabeled annexin V performed better than I-123 in the pig studies set forth in Example III hereof.

Radiolabeling of annexin V with a radionuclide using an $N_2S_2$ or $N_3S$ chelating compound may be conducted using either a pre-formed or a post-formed approach. That is, the radionuclide is either complexed within the chelating compound prior to (pre-formed) or following (post-formed) conjugation of the chelating compound to annexin V. The pre-formed approach is preferred and suitable procedures therefor are set forth in Examples I, II, IV, and XV. Further studies indicated that the pre-formed radiolabeling approach yields two radiometric peaks by HPLC analysis. The appearance of two peaks results from cysteine-conjugated annexin V as well as lysine-conjugated annexin V. Thus, the cysteine amino acid of annexin V can be either deleted or replaced with other non-sulfur containing amino acid to result in a monomerically labeled annexin V, see Example IX. Using the preformed approach to radiolabel the modified annexin V also results in a monomerically labeled annexin V. The conjugation can occur through the accessible sulfhydryl group of a modified annexin, instead of through the lysine residue of the modified annexin.

For embodiments of the present invention wherein chelating compounds exhibiting rapid complexation of radionuclide at room temperature, chelating compounds of the following structure may be employed:

wherein n=0 to 1 and one or more T substituents incorporate a functional group available and suitable for conjugation with another conjugate component. In the example noted above, a functional group, such as an amine, is capable of reacting with the lysine carboxyl moiety or an activated ester derivative thereof. Alternatively, an active-ester bearing chelating compound may be conjugated to an amino functional group, for example.

An esterase-sensitive chelating compound can be used in a variety of the embodiments of the present invention. Such embodiments include annexin-chelating compound conjugates, including modified annexin-chelating compound conjugates, as well as multimer-chelating compound conjugates. A hexose moiety can be utilized in in the above embodiments. An esterase-sensitive chelating compound is cleaved during the metabolism of the radiolabeled protein in the liver to generate radioactivity associated catabolites of favorable redistribution, resulting in the reduction of background radioactivity adjacent to the heart and lungs. It is desirable to have a greater fraction of the technetium-99m released rapidly by the liver, and then excreted by the kidneys. This is accomplished by conjugating an esterase-sensitive chelating compound to the annexin protein. The ester component of this chelating compound is cleaved during metabolism of labeled protein in the liver, resulting in greater release of radioactivity from the liver into the blood and excreted from the kidneys. A preferred esterase-sensitive chelating compound one containing $N_3S$-serylsuccinate, as described in U.S. Pat. No. 5,112,953.

The following structure may be employed with annexin to obtain the above mentioned results:

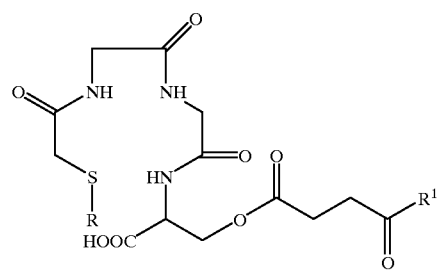

wherein R is any acid labile or base labile sulfur protecting group known in the art, such as ethoxyethyl and $R^1$ is activated esters which include N-hydroxysuccimidate tetraflurophenyl and tetraflurophenyl and tetrofluro-thiophenyl esters. One of ordinary skill in the art is versed in the nature and specificity of functional moieties, and such nature and specificity are also discussed herein.

As indicated previously, annexin molecules may be modified by the addition of from about 2 to about 6 terminal amino acid residues to facilitate the conjugation reaction between the annexin molecule and a chelating compound, or between the annexin molecule and a hexose moiety, or between the annexin molecule and either a linker or a hexose moiety. For example, terminal amino acid residues may be added to provide a sulfhydryl group or to provide a group capable of derivatization to a maleimide group, with such sulfhydryl and maleimide groups available for the conjugation reaction. This modification may be made by protein chemistry methods or via production of an appropriate fusion protein or other techniques useful therefor.

In one embodiment of the invention, a recombinant annexin molecule is modified at the N-terminus by the addition of amino acid residues, provided that at least one of the amino acids provides an accessible sulfhydryl group. For example, this can be accomplished with the addition of at least a single cysteine residue near the N-terminus. A preferred modified annexin as defined herein is a monomeric form of annexin V with an N-terminal extension of the preferred amino acid sequence of Ala-Cys-Asp-His-Ser-Met (SEQ ID NO:1). One advantage of this configuration is that with the cysteine near the N-terminus, the sulfhydryl and neighboring amide groups provide for chelation of the technetium resulting in an $N_3S$-like stable chelating compound, for direct labeling. It is intended within the present invention that adjacent amino acid donor atoms from amino acid moieties will wrap around the base of the metal oxo bond in a square pyramidal arrangement, thus achieving stability, similiar to stable chelation achieved by utilzing an $N_3S$ chelating compound.

Another example of the production of a modified annexin molecule contains a single cysteine residue as the second residue in an N-terminal extension of six amino acids. In this example, the single natural internal cysteine residue has been mutated to a non-sulfur containing amino acid, such as alanine or serine. A method for mutating the cysteine residue is provided by Example VIII. This amino acid extension provides a highly flexible means to attach functional moieties to the N-terminal region of an annexin, such as annexin V. The procedures described herein successfully produce monomeric and dimeric modified annexin V molecules. It is apparent that the proteins are substantially pure and of the expected molecular weight. In addition, any production of a modified annexin V dimer can be quantitatively converted to the monomer, by treatment with 2-mercaptoethanol, confirming the presence of the expected disulfide linkage.

Measurements of the membrane binding properties of modified annexin, and the modified annexin dimer in a competition assay against native monomeric annexin V have been performed. The dimer is 6-fold more potent than monomeric annexin V in displacing labeled ligand from the membrane. Pharmacokinetic studies disclosed herein have shown that the increased molecular weight of the modified annexin dimer does not slow its rate of disappearance from the blood. In fact the modified annexin V dimer is removed from the blood at about the same rate as wild-type monomeric annexin V. See Table I below.

TABLE I

Pharmacokinetics of $^{125}I$ Iodinated modified annexin V Dimer and Annexin V in Mice

| Time Since Injection | Radioactivity in Blood (% ID/g) | |
|---|---|---|
| | Annexin V | Modified Annexin V Dimer |
| 15 min | 1.27 ± 0.12 | 1.70 ± 0.02 |
| 60 min | 0.60 ± 0.04 | 0.36 ± 0.04 |
| 240 min | 0.06 ± 0.01 | 0.06 ± 0.02 |

The disclosure of the present invention shows that the dimeric molecule of annexin V is likely to have a higher affinity for the platelet membrane, most likely due to a slower dissociation rate. Thus, this molecule may be taken up to a higher level or retained longer in the thrombus in vivo, thus improving the target-to-background ratio at any given time.

Radiolabeled annexins, including radiolabeled annexin-galactose conjugates and radiolabeled annexin-galactose cluster conjugates, of the present invention offer an additional advantage over the previously prepared I-123-labeled annexins, in that they are amenable to packaging in a cold kit. That is, the annexin or annexin-galactose or annexin-galactose cluster or galactose cluster and chelating compound components may be individually vialed and provided separately from the Tc-99m component (and, possibly, vialed separately from each other). When a patient requiring a thrombus image is identified, a cold kit may be ordered or retrieved from storage; Tc-99m may be obtained from a radiopharmacy or other source thereof; the pre-formed or post-formed chelation/complexation process is performed; the radiolabeled annexin, radiolabeled annexin-galactose conjugate or radiolabeled annexin-galactose cluster conjugate is administered to the patient; and the patient is subsequently imaged. For radiolabeled annexin-galactose conjugates, an annexin-galactose conjugate is preferably prepared and vialed in the kit. For radiolabeled annexin-galactose cluster conjugates, a chelating compound-annexin-galactose cluster conjugate is preferably prepared and vialed in the kit, although annexin-galactose cluster/chelating compound two component or other multi-component kits may also be used.

It is contemplated by the present invention that Tc-99m can be directly complexed through a specific bioengineered site on annexin V, without the need for intermediate production of an amine-directed active ester containing Tc-99m. To facilitate direct labeling, the modified Annexin V N-terminal sequence can consist of Ala-Cys-Asp-His-Ser- . . . etc, for example. As the cysteine is near the N-terminus, the sulfhydryl and neighboring amide groups are able to chelate the technetium resulting in an endogenous $MAG_3$-like, stable technetium chelate. A defined chelate system through an endogenous protein sequence can be achieved wherein the adjacent amide donor atoms from amino acid residues wrap around the base of the metal oxo bond in a square pyramidal arrangement; thus, providing for stable chelation similar to stable chelation achieved when using an $N_3S$ chelate in a preformed labeling method. For the endogenous chelationm technetium-99m is the preferred radionuclide.

Lyophilization and vialing of the conjugate components in a sterile, pyrogen-free environment may be accomplished via techniques, known to persons skilled in the art of good manufacturing practices, particularly as such practices relate to biological materials.

Radiolabeled annexins, including radiolabeled annexin-galactose conjugates or radiolabeled annexin-galactose cluster conjugates, of the present invention are administered in such amounts as to deliver a diagnostically effective amount of radionuclide to target sites. Appropriate administered doses depend on a variety of factors that are largely patient specific, and practitioners in the art will consider such factors in the practice of the present invention. The components of the radiolabeled annexin also impact dose amounts in ways that are known to be or are routinely ascertainable by practitioners in the art. In general, radiolabeled annexin, including radiolabeled annexin-galactose conjugate or radiolabeled annexin-galactose cluster conjugate, is administered to large mammals at a dose ranging between about 0.3 and about 300 micrograms/kg body weight of the recipient, with from about 3 to about 10 micrograms/kg preferred, depending upon the physiological characteristics of the patient and the ailment involved or suspected.

A practitioner in the art is capable of identifying an appropriate dose and administration route for a given recipient with a given ailment.

Radiolabeled annexins, including radiolabeled annexin-galactose conjugates or radiolabeled annexin-galactose cluster conjugates, of the present invention may be administered in any convenient manner therefor. For example, intravenous infusion may be employed to administer radiolabeled annexins. Other routes of administration also find utility in the practice of the present invention. Exemplary additional administration routes are injection by the arterial (e.g., coronary artery), intracoronary, intralymphatic, intrathecal, or other intracavity routes, and the like.

After administration of the radionuclide, depending upon the nature of the radionuclide and the purpose of the administration, the recipient may be subject to various procedures for detection of radioactive emissions from the site or sites at which the radionuclide localizes. For example, conjugates containing Tc-99m are imageable by a gamma camera.

The invention is further described through presentation of the following examples. These examples are offered by way of illustration, and not by way of limitation.

EXAMPLE I

Procedure for Radiolabeling an Annexin—$N_2S_2$ Chelate Conjugate

Annexin V can be isolated from a variety of tissue extracts, such as liver, lung and placenta, in accordance with procedures set forth in Funakoshi et al., *Biochem.* 26: 8087–92, 1987); Tait et al., *Biochem.* 27: 6268–76, 1988; and U.S. Pat. No. 4,937,324, for example. In addition, annexin V can be expressed in *E. coli*, as described by Tait et al., *Archives of Biochemistry and Biophysics* 288: 141–44, 1991.

Annexin V was radiolabeled with Tc-99m by using a diamide dimercaptide N2S2 chelating compound in accordance with the OncoTrac® (also referred to as Verluma™) Small Cell Lung Cancer Imaging Kit labeling procedure described in *J. Nucl. Med.* 32: 1445–51, 1991.

A preferred method for radiolabeling annexin V with Tc-99m constitutes a modified OncoTrac® kit procedure using C-18 Baker purified Tc-99m-$N_2S_2$-TFP. In this procedure, an acidified active ester solution was prepared by adding 0.16 ml of 0.2M hydrochloric acid: glacial acetic acid (14:2 ratio) to 0.6 ml of 2,3,5,6,-tetrafluorophenyl 4,5-bis-(S-1-ethoxy-ethyl-mercaptoacetamido)pentanoate (0.3 mg, 0.0005 mole freshly dissolved in 0.9 ml of isopropyl alcohol). Then 0.5 ml of this solution was added to 1.1 ml of Tc-99m-gluconate (prepared from 0.12 mg $SnCl_2$ 2 $H_2O$, 5.0 mg sodium gluconate at pH 6.1–6.3, and 100 mCi/ml of [Tc-99m] pertechnetate, i.e., the first step in the OncoTrac® kit labeling procedure). The reaction mixture was heated at 75° C. for 15 minutes followed by cooling on ice. The resulting Tc-99m transchelated tetrafluorophenyl active ester derivative of Tc-99m-4,5-bis(thioacetamido) pentanoate was, optionally and preferably diluted with 2 ml water and purified by loading the reaction mixture on a conditioned C-18 cartridge (J. T. Baker, Phillipsberg, N.J.), washing with 2.0 ml of water eight times followed by drying the column for 5 minutes, and eluting with 100% acetonitrile. The solvent was evaporated under a steady stream of $N_2$ gas. Then 0.15 ml of phosphate buffered saline (PBS), 0.15 ml of annexin V at 2.35 mg/ml, and 0.2 ml of 0.2M bicarbonate (pH 10.0) were added for conjugation to the Tc-99m-$N_2S_2$ chelate. After 20 minutes at room temperature, the Tc-99m-$N_2S_2$-annexin V conjugate was purified by passage through a G-25 SEPHADEX® (PD-10) column (available from Pharmacia, Piscataway, N.J.) equilibrated with PBS. Fractions (1.0 ml) were collected, and those fractions containing annexin V were pooled. Protein concentration was determined by UV absorption at 280 nm. Tc-99m-annexin V (300–350 μg) conjugate solution was diluted and stored in PBS containing bovine serum albumin (BSA) at a final concentration of 15–20 mg BSA/ml PBS prior to injection.

EXAMPLE II

Procedure for Radiolabeling an Annexin—$N_3S$ Chelate Conjugate

S-benzoylmercaptoacetylglycylglycylglycine (S-benzoyl $MAG_3$) is prepared in accordance with the procedures described in U.S. Pat. No. 4,965,392. Then 25 micrograms of S-benzoylmercaptoacetylglycyl-glycylglycine is dissolved in 0.10 ml of 1.0M carbonate buffer (pH 12). Then 75 mCi of Tc-99m pertechnetate is added in about 1.0 ml followed by 1.0 mg of freshly dissolved 10 sodium dithionite (10 mg/ml). This mixture is heated at 100° C., plus or minus 4° C., for 3 minutes, then is cooled in an ice bath for 5 minutes to give Tc-99m-$MAG_3$ as determined by ITLC ($CH_3CN$ solvent); anion exchange HPLC (Beckman AX, 10 micron 0.01M $Na_2SO_4$/0.01M $Na_3PO_4$, pH is 7.0); and reverse phase HPLC (Beckman ODS, 5 micron 2% $CH_3CN$/0.01M $Na_3PO4$, pH 7.0).

The Tc-99m-$MAG_3$ complex in carboxylate form is then esterified; 0.20 ml 1N HCl, 0.30 ml of 0.2M phosphate buffer pH 6.0, 10.0 mg 2,3,5,6-tetrafluorophenol (TFP) in 0.01 ml 90% $CH_3CN$, and 12.5 mg of EDC (1-(3-dimethylaminopropyl)-3-ethylcarbodiimide hydrochloride) in 0.10 ml of 90% $CH_3CN$ are combined, and the reactants are mixed at room temperature (25° C., plus or minus 2° C.) for 1 hour. At this point, a yield of Tc-99m-$MAG_3$-TFP ester as determined by ITLC ($CH_3CN$ solvent); anion exchange HPLC (Beckman AX, 10 micron 0.01M $Na_2SO_4$/0.01M $Na_3PO_4$, pH 7.0); and reverse phase HPLC (Beckman ODS, 5 micron 34% $CH_3CN$/0.01M $Na_3PO_4$, pH 7.0). The preparation is purified using a C-18 Baker column. The reaction mixture is, optionally and preferably diluted with 2 ml of water and loaded in the column, washed two times with water and then eight times with 10% $C_2H_5OH$/0.01M $Na_3PO_4$, pH 7.0. The product is eluted with $CH_3CN$, and the solvent is removed prior to conjugation with annexin V.

The conjugation of the active ester to annexin V is carried out by adding annexin V in a phosphate buffer, pH 9.5, to the Tc-99m-MAG$_3$-TFP ester. The reaction is carried out for at least 30 minutes, and the desired radiolabeled annexin product is obtained by passage through a PD-10 gel filtration column.

EXAMPLE III

Thrombus Imaging With a Radiolabeled Annexin

A. Animal Preparation—LA Vascular Thrombi Fasting 25–30 kg Yorkshire swine were sedated with intramuscular Telazol (5–10 mg/kg) (commercially available from AVECO Co.) and commercially available Atropine (1 mg, Elkins-Sinn, Inc., Cherry Hill, N.J.). Surital (200 mg) (commercially available from Abbott Laboratories) anaesthesia was administered intravenously. The animals were intubated and given inhalation anaesthesia of 1.5–2% halothane (commercially available from Abbott Laboratories, Abbott Park, Ill.) and O$_2$ sufficient to obtain a deep level of anesthesia and physiologic arterial blood gases. Continuous electrocardiographic monitoring was instituted using alligator clip electrodes. A cut down in the neck region was conducted, and an 8 french catheter (USCI Co, Billerica, Mass.) was placed in the right common carotid artery for blood pressure and arterial blood gas monitoring as well as for blood sampling.

The swine were placed in a right lateral decubitus position, and a lateral thoracotomy was performed to expose the heart. The incision was held open by a thoracotomy retractor. The pericardium was opened, and the left atrial appendage was isolated from the left atrium by a vascular cross-clamp. Rubber tipped forceps were used to gently crush the appendage. Five minutes later, ricinoleate (1 mg, ICN Pharmaceuticals, Costa Mesa, Calif.) and thrombin (50 mg, Johnson and Johnson Co., Arlington, Tex.) were injected into the LAA (left atrial appendage) using a 27 Ga needle. The cross-clamp was removed 10 minutes later.

One hour after the crush injury, Tc-99m-annexin V, prepared in accordance with Example I above, was administered as an intravenous bolus dose in an ear vein. The intravenous line was then flushed with saline. In 7 animals, I-125 labeled ovalbumin was administered as a non-specific control preparable, for example, by the procedure described by Fraker et al., *Biochem. Biophys. Res. Commun.* 80: 849–57, 1978). Briefly, I-125-radiolabeled ovalbumin was prepared by the Iodogen method, employing 600 μg ovalbumin (Sigma Chemical Co., St. Louis, Mo.) and NaI-125 (2mCi, 0.92 nmol).

Image acquisition was performed as described below. At the end of the experimental procedure (generally about 150 minutes), the animals were sacrificed by an intravenous bolus dose of 80 mEq of KCl while the animals were still under general anaesthetic. A final blood sample was taken for well counting. The heart was rapidly excised, washed free of blood and dissected into samples for well counting. Additional samples of carotid artery, lung, liver, spleen, muscle and kidney were obtained in some animals.

B. Controls. Five different types of controls were used: open chest sham; closed chest sham; ovalbumin; indium platelets; and non-specific Tc-99m-labeled antibody.

1. Open Chest Sham. In three animals, the heart was exposed as above, but the left atrium was not isolated, crushed or injected with ricinoleate/thrombin. Marker images with a cobalt marker were performed as described below, and the Tc-99m-annexin V was injected 30–60 minutes after LAA exposure. Imaging and sample acquisition were identical to that described in A above.

2. Closed Chest Sham. In seven animals, an ear intravenous line was established. No thoracotomy was performed. Sedation and anesthesia were identical to that described in A above. The Tc-99m-annexin V (±other control radionuclides, such as I-125 ovalbumin or In-111-platelets) was administered and image acquisition was performed.

3. Ovalbumin. I-125 ovalbumin was administered in 7 animals as a negative control protein. Ovalbumin has a molecular size similar to that of annexin, and exhibits a slightly slower blood clearance.

4. Indium Platelets. In-111 platelet labeling was performed in 7 animals as a positive well counting label. In-111 radiolabeled platelets were prepared in accordance with the procedure described by Stratton et al., *Am. J. Cardiol.* 47: 874, 1981 and Stratton et al., *Circulation* 69: 561, 1984. Imaging was not attempted because of the long serum half-life of the In-111-platelets.

5. Non-specific Tc-Labeled Antibody. In a single experiment, a left atrial (LA) thrombi was created by the above method, but Tc-99m-Annexin V was not administered. Instead, a Tc-99m-Fab fragment of an antibody designated as NR-LU-10 was administered. NR-LU-10 is a 150 kilodalton molecular weight IgG2b monoclonal antibody that recognizes an approximately 40 kilodalton glycoprotein antigen expressed on most carcinomas. NR-LU-10 is a well characterized pancarcinoma antibody that has been safely administered to over 565 patients in human clinical trials. NR-LU-10-Fab is prepared in accordance with known techniques and is radiolabeled in accordance with the procedures described in *J. Nucl. Med.* 32: 1445–51, 1991 and by the modified C-18 Baker purified Tc-99m-N$_2$S$_2$-TFP procedure described in Example I for preparing radiolabeled annexin V. This Tc-99m-Fab conjugate was designed as a negative control for both well counting and imaging.

C. Imaging. A cobalt marker was placed on the exposed surface of the LAA and held in place with surgical tape affixed to the thoracotomy retractor. The tape was adjusted so that the marker generally moved with the LAA with each cardiac cycle. Marker images were acquired for 10 seconds in each planar view and 10 seconds in each tomographic slice. The cobalt marker was then removed.

A General Electric Starport camera with a general purpose collimator was used to acquire the Tc-99m images. Five minute planar acquisitions were performed sequentially in the left lateral, 45 LAO, and anterior views. These were followed by a 10 minute tomographic acquisition. This full set of 3 planar and 1 tomographic acquisitions was repeated for a total of 5 sets. Care was taken not to move the pig or imaging gantry during the entire imaging sequence. Images were recorded on a Microdelta computer slaved to a VAX mainframe system. Images were stored on tape or on the VAX hard drive. Planar image analysis consisted of first viewing the image with the marker and recording the marker position on the viewing terminal screen. The first image acquired after Tc-99m-annexin V injection was used to define the cardiac blood pool. Each subsequent image was viewed and analyzed using the marker and initial blood pool as references. Each image was scored as positive, equivocal or negative.

Thirteen animals had left atrial thrombi created and were imaged as described above. Twelve animals had Tc-99m-annexin V injected for imaging, and one animal had a non-specific Tc-99m Fab injected as a control. Closed chest imaging was performed in 7 animals without atrial injury, and open chest sham experiments were performed in 3 animals. In animals with atrial thrombi, all planar images taken at less than 35 minutes after administration of Tc-99m-annexin V were negative. Nine of the atrial thrombi planar images taken at greater than 70 minutes were positive, 1 was equivocal and 2 were negative. All of the tomographic images of atrial thrombi were either positive (n=10) or equivocal (n=2) at imaging times of greater than 2 hours post injection. The average time in which the planar images became positive following administration of Tc-99m-annexin V was 82 minutes (35–135 minutes).

None of the closed chest control animals had positive images. One of the three open chest shams had a positive image at 85 minutes. This false positive is believed to result from the production of surgically-induced thrombi.

These results indicate that intravenous administration of Tc-99m-annexin V permitted acquisition of diagnostic images identifying atrial vascular thrombi within a short time period following conjugate administration.

D. Sample Collection. Samples (both blood and tissue), as described above, were weighed and placed in vials for immediate counting of Tc-99m. After the Tc-99m had decayed (typically at 5–7 days), the samples were re-assayed to obtain the I-125 counts. Each vial was counted for 1 minute. The counts were corrected for decay, then for weight, and recorded as counts per minute per gram. The counts per minute per gram for each sample were then normalized by dividing the counts per minute per gram of the final blood specimen. Consequently, the results for each sample were calculated in a ratio with the last blood sample, permitting meaningful comparison between animals. This procedure was performed for all radionuclides in a given experiment.

Well counting ratios were obtained for a variety of tissue samples. For the injured tissues and thrombi, multiple specimens were usually taken from the same animal. In those cases, the maximum ratio for any one specimen is reported, as well as the average of all specimens taken. The maximum for each animal was averaged across all animals and is reported as the Maximum Anx-V Ratio.

These results indicate that Tc-99m-annexin V localizes preferentially to atrial thrombi and injured left atrium, with the highest non-target localization occurring in the kidney. The kidney level is at least partially indicative of excretion of Tc-99m-annexin V via the renal route.

EXAMPLE IV

Radiolabeled Annexin-Galactose Conjugates

A. Annexin V—Preparation from human placenta and by expression in *E. coli*. Annexin V was purified from human placenta to a final purity of 99% as described by Funakoshi et. al., *Biochemistry* 26, 5572–78, 1987 and Tait et. al., *Biochemistry* 27, 6268–76, 1988.

Alternatively, annexin V was obtained, but not employed in the following experiments, by expression in *E. coli*. This expression was conducted as follows.

1. Preparation of bulk fermentation supernatant. Standard molecular biology techniques were used to express annexin V in *E. coli*. More specifically, the protein coding region of annexin V cDNA (see, Funakoshi et. al. referenced above) was inserted into the NdeI/BamHI site of plasmid pET-12a (Novagen, Madison, Wis.). The selected plasmid was used to transform *E. coli* strain BL21(DE3) (Novagen).

Individual colonies (clones) were isolated on Luria Broth plates containing 50 g/ml ampicillin or carbenicillin, as discussed in Sambrook et al., "Molecular Cloning Laboratory Manual," 2nd ed., Cold Springs Harbor Laboratory Press, 1989. For production, cultures of the selected clones containing the desired plasmid were grown overnight at 37° C. with shaking in Terrific Broth (see, Tartof et. al., *Bethesda Res. Lab. Focus,* 9: 12, 1987) containing 50 µg/mL carbenicillin (commercially available from Sigma Chemical Co., St. Louis, Mo.). The culture was diluted 1:20 in the same medium and incubated at 37° C. with shaking for 18–24 hr. The bacteria were harvested by centrifugation, washed once with an equal volume of 0.05M Tris-HCl, 0.15M sodium chloride, pH 8, and stored as pellets at −20° C. Pellets were thawed and resuspended with 10–15% (w/v) cold 0.05M Tris-HCl, 0.02M Na$_4$EDTA, pH 7.2. The suspension was sonicated for 4 min on ice, centrifuged, and the supernatant stored at −70° C.

2. Purification of annexin V from bulk fermentation supernatant. After thawing, the supernatant was filtered using a 0.1 µm hollow fiber unit (commercially available from A/G Technology, Needham, Mass.), and the conductivity adjusted with concentrated sodium chloride to equal 0.02M Tris-HCl, 0.5M sodium chloride, pH 8. Polyethyleneimine-WP (J. T. Baker, Phillipsberg, N.J.) was suspended in 0.02M Tris-HCl, 0.5M sodium chloride, pH 8, and 1 g of resin per 10 ml of bulk fermentation supernatant was added to the filtered supernatant. After stirring for 30 min, the supernatant was removed, exchanged into 0.02M Tris-HCl, pH 8, and applied to a Q-SEPHAROSE® HP column (Pharmacia, Piscataway, N.J.) equilibrated in the same buffer. The column was developed with a step gradient of 0–0.5M sodium chloride. Fractions were assayed for annexin V by size exclusion HPLC, and fractions containing $A_{280}$ absorbing material of appropriate size were pooled. The semi-purified annexin V was exchanged into PBS and concentrated by ultra-filtration. Gel filtration over SEPHACRYL® 100 HP (Pharmacia) equilibrated in PBS yielded the purified protein. The protein concentration was adjusted to 1 mg/ml, sterile 0.2 µm filtered, and stored at 2–8° C.

B. Derivatization of Annexin V with Galactose. The general method of Lee et al., *Biochemistry* 15: 6268–76, 1976 was followed.

a. Preparation of 2-imino-2-methoxyethyl-1-thio-D-galactopyranoside.

A 1.0M solution of cyanomethyl-2,3,4,6-tetra-O-acetyl-1-thio-D-galactopyranoside (commercially available from Sigma Chemical Company, St. Louis, Mo.) was prepared by dissolving 1.83 g (4.5 mmole) in 4.5 ml anhydrous methanol with heating to 50° C. The solution was maintained at 50° C., and 0.1 ml (0.45 mmole) of 25% sodium methoxide in methanol (commercially available from Aldrich Chemical Company, Milwaukee, Wis.) was added with continuous stirring. After 6 hr at 50° C., the methanol was removed under reduced pressure yielding the galactose methyl imidate as a colorless, viscous oil.

b. Galactosylation of annexin V

The galactose methyl imidate was offered to annexin V in molar ratios of 300:1, 150:1, and 75:1. For the 300:1 offering, 3.35 mg of galactose methyl imidate in methanol was taken to an oil under a stream of nitrogen. To the oil was added 2.53 mg of annexin V in 0.05M HEPES buffer (commercially available from Sigma Chemical Co., St. Louis, Mo.), pH 7.4 and 0.04 ml of 0.5M sodium borate buffer, pH 8.5. The solution was mixed for 1 hr at room temperature by tumbling the reaction vessel, and was then allowed to stand at room temperature overnight (approximately 18 hr). The reaction mixture was diluted with 0.4 ml PBS, transferred to dialysis tubing (6000–8000 MW cut-off), and dialyzed 24 hr against PBS. After removing the material from the dialysis bag, the solution was filtered through a 0.2 μm syringe filter. The other offering levels were conducted analogously.

C. Characterization of Galactose-Derivatized Annexin V. Protein concentration was determined using $A_{280}$ of 0.6 for a 1 mg/ml solution of annexin V. The number of galactose residues per molecule of annexin V was determined by measuring the total number of reactive amines on annexin V before and after reaction with galactose methyl imidate using trinitrobenzenesulfonic acid, as described by Habeeb, *Analytical Biochemistry* 14: 328–36, 1966.

| Offering Ratio | Substitution Ratio |
|---|---|
| 300:1 | 4.7:1 |
| 150:1 | 2.3:1 |
| 75:1 | 1.1:1 |

The ability of galactose-modified annexin V to bind to activated platelets was assessed by determining its ability to inhibit the binding of unmodified, $^{125}I$ radiolabeled annexin V to freshly isolated human platelets, following the method of Thiagarajan and Tait *J. Biol. Chem.*, 265: 17240–43, 1990. The following table shows the results of the competition assay, both in absolute value (left column) and in a value normalized to 100% for unmodified annexin V (right column).

| Substitution Ratio | Competition (% of control) | Competition (% of control) |
|---|---|---|
| 4.7 | 0 | 0 |
| 2.3 | 5.7 | 7.6 |
| 1.1 | 21.4 | 28.7 |
| unmodified | 74.5 | 100 |

D. Preparation of Tc-99m-Annexin V-Galactose. Annexin V-galactose was radiolabeled with technetium-99m using a diamide dimercaptide ($N_2S_2$) chelating compounds as described by Kasina et. al., *J. Nucl. Med.* 32: 1445–51, 1991. The preformed active ester chelating compound was diluted with 2.0 ml water and purified before conjugation to annexin V-galactose using a modified conditioned C-18 column (commercially available from J. T. Baker), as described by Fritzberg et. al., *Proc. Natl. Acad. Sci. USA* 85: 4025–29, 1988, washing with 2.0 ml water eight times followed by drying the column for 5 min and eluting with 100% acetonitrile. The solvent was removed under a steady stream of $N_2$. Then 0.15 ml of PBS, 0.35 ml of annexin V-galactose (4.7:1 galactose:annexin V) at 1.0 mg/ml, and 0.2 ml of 0.2M bicarbonate buffer (pH 10.0) were added for conjugation to Tc-99m-$N_2S_2$-TFP ester. After 20 min at room temperature, the Tc-99m-annexin V-galactose conjugate was purified by passage through a G-25 SEPHADEX® PD-10 column (commercially available from Pharmacia) equilibrated with PBS.

Fractions of 1.0 ml were collected, and fractions containing annexin V were pooled. Protein concentration was determined by UV absorption at 280 nm. The radiochemical yield of the conjugate was 35.3%. The radiochemical purity was 99.8%, as assessed by instant thin layer chromatography on silica gel impregnated glass fiber sheets developed in 12% w/v aqueous trichloroacetic acid. The ITLC sheets were cut into two halves, and each half was counted in a gamma counter or a dose calibrator. The radiolabeled annexin V-galactose conjugate precipitated at the origin, and any non-protein-bound radioactivity migrated with the solvent front in this solvent system. Tc-99m-annexin V-galactose conjugate (300–350 g) solution was diluted and stored in PBS containing bovine serum albumin (commercially available from Sigma Chemical Co.) at a final concentration of 15–20 mg/ml PBS prior to intravenous injection.

Figure 2:
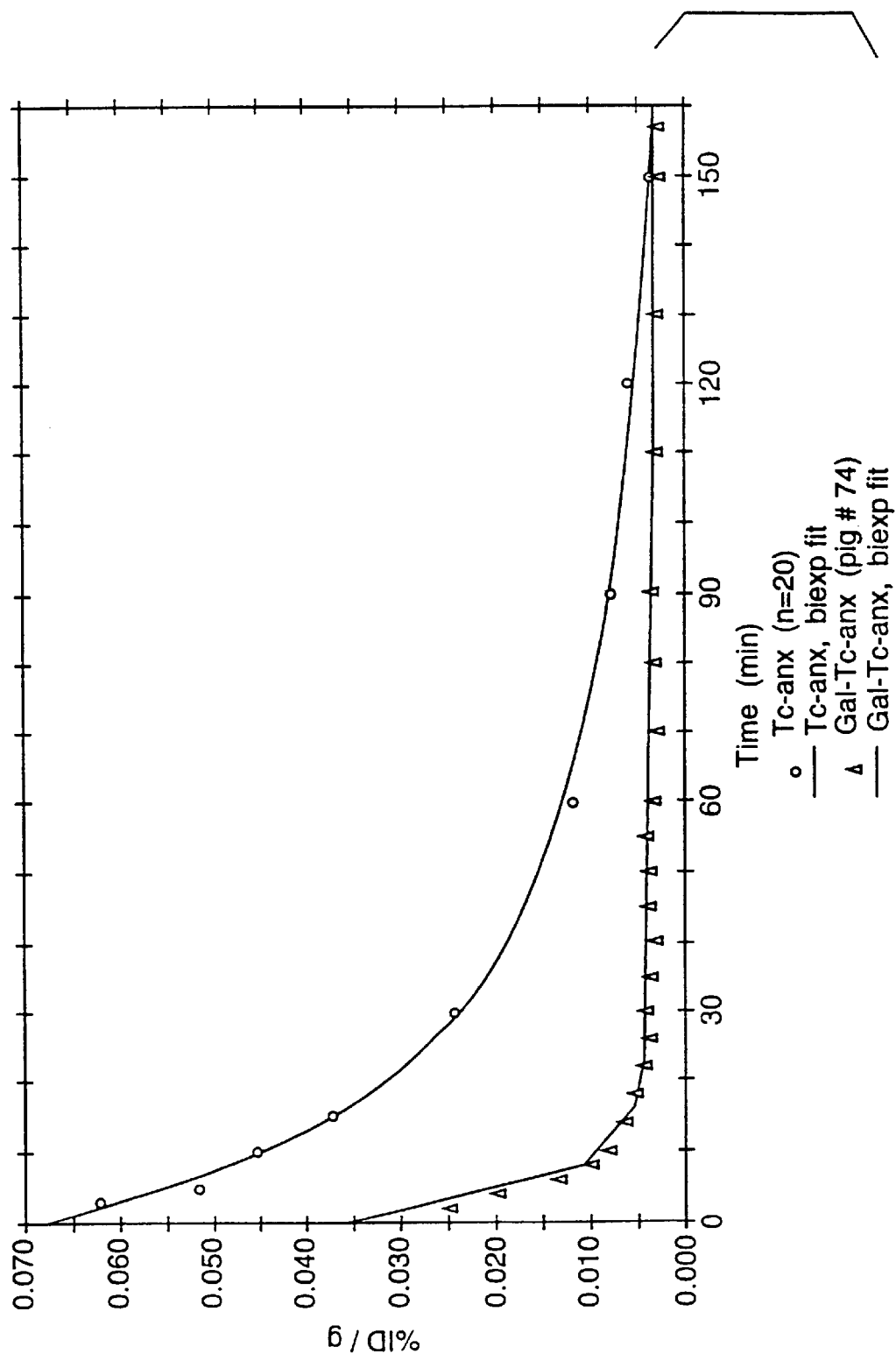
FIG. 2 shows the blood clearance of Tc-99m-annexin V (○) and of Tc-99m-annexin V-galactose (Δ)

E. Blood Clearance of Tc-99m-Annexin V and of Tc-99m-Annexin V-Galactose. An animal model, as previously described in Example III, was employed to evaluate blood clearance of the molecules. For N=20 swine, the blood clearance (FIG. 2) is biphasic (biexponential):

% ID/g a=0.0389 t1/2 a=9.6 min

% ID/g b=0.0300 t1/2 b=46 min a+b=0.0689, therefore 57% (0.0389/0.0689) of the injected dose/gram of blood is cleared in the faster a phase and 43% of the ID/g is cleared in the slower b phase.

Blood clearance of Tc-99m-annexin V-galactose in the swine (FIG. 2) is also biphasic (biexponential):

% ID/g a=0.0313 t1/2 a=3.5 min

% ID/g b=0.0045 t1/2 b=160 min a+b=0.0358, therefore 87% (0.0313/0.0358) of the injected dose/gram of blood is cleared very quickly in the early a phase. This more rapid clearance reduces the background radioactivity in the blood compartment, i.e., the noise, and therefore improves the signal to noise ratio. Consequently, thrombus imaging can be achieved at shorter time points.

EXAMPLE V

Chelating Compound Preparation 4,4-Diethoxycarbonylpropyl-1,3-dianiline: A stirred solution of 2.065 g (1.25 mole) ethyl-4-amino benzoate, 14.35 mL (0.125 mole) 1,3-di-iodopropane and 10.5 g (0.125 mole) sodium bicarbonate in 500 mL dry DMSO is heated at 100° C. for 3 hours under nitrogen. Upon cooling, the mixture is poured into 2 L of ice water with stirring, and the resulting precipitate is collected by filtration. The precipitate is then washed with glacial acetic acid (14×75 mL) until all of the starting ethyl-4-aminobenzoate has been removed. After drying in vacuo, the product, thus obtained, is used in the next step without further purification.

1,3-Di(2-imino-6-ethoxycarbonylbenzthiazolyl-3-) propane: Ammonium thiocyanate (16.5 g, 0.217 mole) is added to a magnetically stirred suspension of 4,4-diethoxycarbonylpropyl-1,3-dianaline (10.0 g, 0.27 mole) in 1500 mL glacial acetic acid. A solution of bromine (34.6 g, 0.216 mole) in 100 mL glacial acetic acid is then added dropwise to the suspension with stirring at room temperature. After stirring the reaction mixture overnight at room temperature, the dihydrobromide salt of the crude product is collected by filtration and dried. The product is isolated by dissolving the crude product in hot water, adjusting to basic pH with the addition of saturated sodium bicarbonate solution, collecting the precipitate by filtration, and drying in vacuo.

N,N'-Bis(2-disulfidyl-4-hydroxycarbonylphenyl)-1,3-propyldiamine: Solid potassium hydroxide (20.0 g, 0.357 mole) is added to a suspension of 1,3-di(2-imino-6-ethoxycarbonylbenzthiazolyl-3-)propane (1.0 g, 0.002 mole) in 40 mL distilled water, and the resulting mixture is heated at 120° C. for 12 hours. Complete dissolution occurs after 1 hour. The reaction mixture is then cooled in an ice bath, and the pH is adjusted to 5.0 with 5.0N acetic acid. The aqueous solution is then extracted with three 100 mL portions of ethyl acetate. The combined ethyl acetate extracts are dried over anhydrous sodium sulfate, and the drying agent is filtered. Removal of solvent yields the product.

Figure 3:
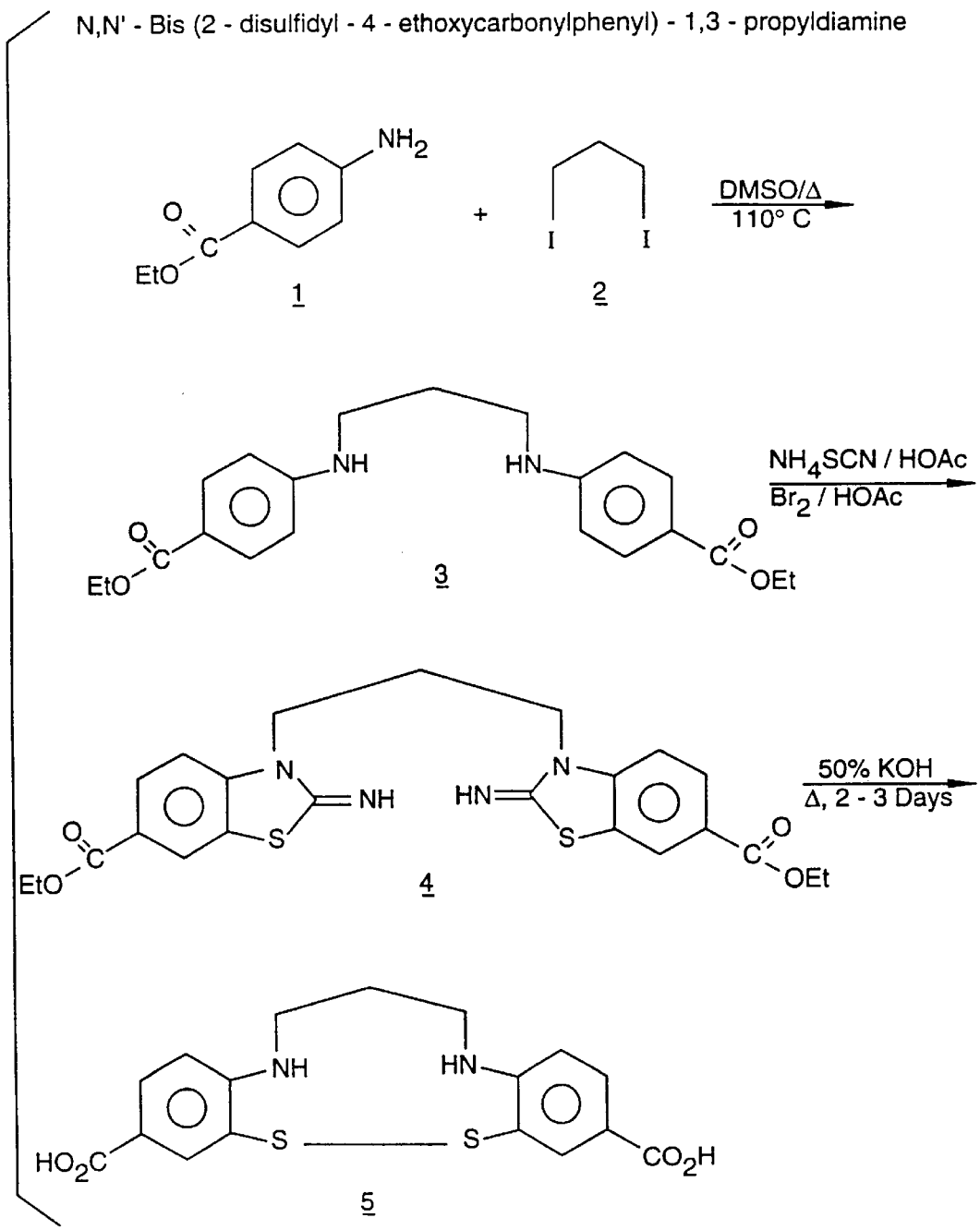
FIG. 3 schematically shows the synthesis of N,N'-bis(2-disulfidyl-4-carbonylphenyl)-1,3-propyldiamine.

To this point, this synthesis is shown schematically in FIG. 3.

N,N'-bis(2-disulfidyl-4-hydroxycarbonylphenyl)-1,3-propyldiamine mono-(methyl-aminocaproate)adduct. To a mixture of N,N'-bis(2-disulfidyl-4-hydroxycarbonylphenyl)-1,3-propyldiamine and 2–3 equivalents of methyl 6-aminohexanoate hydrochloride (prepared as described below in Example VI) in dimethylformamide is added 10 equivalents of triethylamine followed by 0.9–1.0 equivalent of BOP (benzotriazol-1-yloxy-tris-(dimethyl-amino)-phosphonium hexafluorophosphate). The mixture is stirred at 15–30° C. for 2–24 hours and then concentrated. The residue is diluted with deionized water, and the pH is adjusted to approximately 2 with 1N aqueous hydrochloric acid. The mixture is again concentrated. The residue is chromatographed on silica gel. The chromatographic fractions containing product are combined and concentrated to afford the product.

This chelating compound is amenable to use with a suitable trifunctional linker or a pair of bifunctional linkers to form a radiolabeled annexin-galactose cluster conjugate of the present invention. The use thereof with a pair of bifunctional linkers is addressed in the following example.

EXAMPLE VI

Radiolabeled Annexin-Galactose Cluster Conjugates Bifunctional Linker Approach

A. Preparation of an Eight Galactose Cluster

Figure 5A:
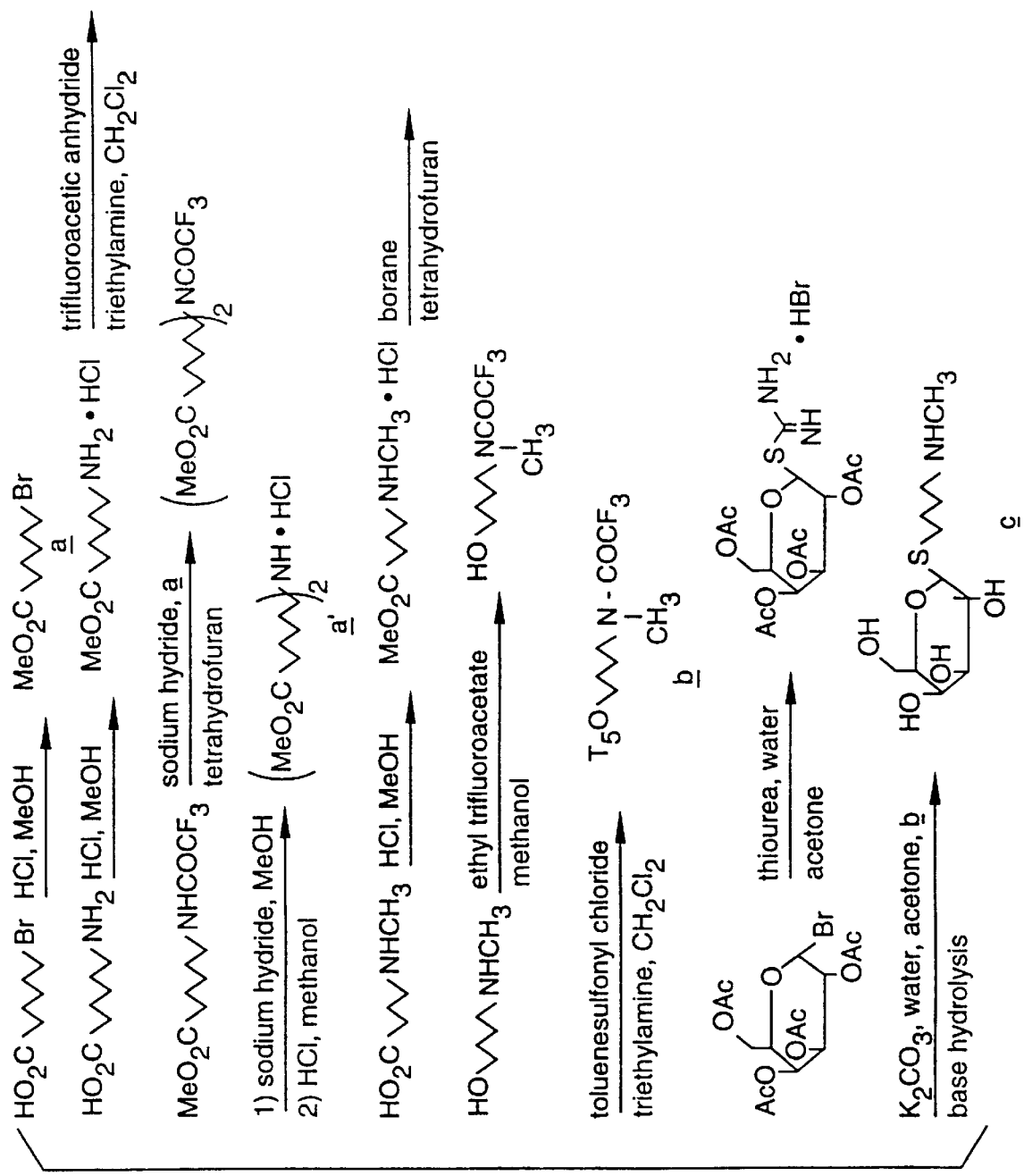
FIGS. 5a and 5b schematically show the synthesis of an eight galactose-containing galactose cluster.
Figure 5B:
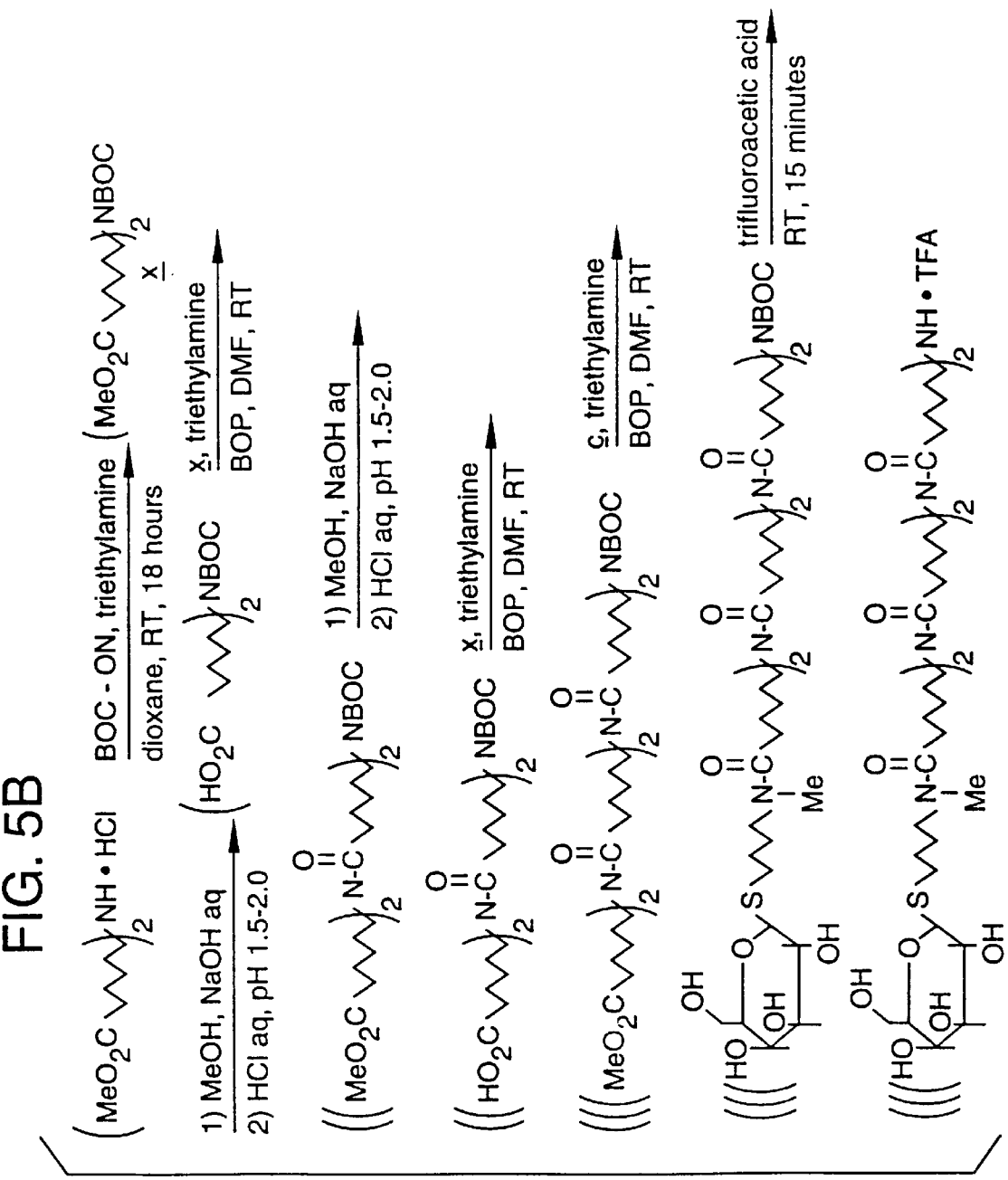

This procedure is schematically shown in FIG. 5.

Methyl 6-bromohexanoate. To a 1 L round bottom flask, charged with 20 g (102.5 mmol) of 6-bromohexanoic acid and 500 mL of methanol, was bubbled hydrogen chloride gas for 2–3 minutes. The mixture was stirred at room temperature for 4 hours and concentrated to afford 21.0 g of the product as a yellow oil (99%): $^1$H-NMR (200 MHz, d$_6$-DMSO); 3.57 (s, 3H), 3.51 (t, 2H), 2.30 (t, 2H), 1.78 (pentet, 2H), and 1.62–1.27 (m, 4H) ppm.

Methyl 6-aminohexanoate hydrochloride. To a 1 L round bottom flask, charged with 40.0 g aminocaproic acid, was added 500 mL of methanol. Hydrogen chloride gas was bubbled through the mixture for 5 minutes, and the mixture was stirred at room temperature for 5 hours. The mixture was then concentrated via rotary evaporation and then under full vacuum pump pressure (<0.1 mm Hg) to afford 55 g of the product as a white solid (99%): $^1$H-NMR (200 MHz, CD$_3$OD); 3.67 (s, 3H), 3.02 (t, 2H), 2.68 (s, 3H), 2.48 (t, 2H), and 2.03–1.87 (pentet, 2H) ppm.

Methyl 6-(trifluoroacetamido)-hexanoate: To a 1 L round bottom flask, charged with 25.0 g (138 mmol) of methyl 6-aminohexanoate hydrochloride and 500 mL of methylene chloride, was added 24 mL (170 mmol) trifluoroacetic anhydride. The mixture was cooled in an ice bath, and 42 mL (301 mmol) of triethylamine was added over a 25–30 minute period. The mixture was stirred at 0° C. to room temperature for 2 hours and then concentrated. The residue was diluted with 150 mL of diethyl ether and 150 mL of petroleum ether, and the resulting solution was washed first with 1N aqueous HCl (3×150 mL) and then with saturated aqueous bicarbonate (3×150 mL). The organic phase was dried over magnesium sulfate, filtered and concentrated to give 32.9 g of the product as a pale yellow oil (99%): $^1$H-NMR (200 MHz, d$_6$-DMSO); 9.39 (m, 1H), 3.57 (s, 3H), 3.14 (q, 2H), 2.29 (t, 2H), 1.60–1.38 (m, 4H), and 1.32–1.19 (m, 2H) ppm.

N N'-Bis(6-methoxycarbonylhexyl)amine hydrochloride. To a 500 mL dry round bottom flask, charged with 12.0 g (50.0 mmol) of the secondary amide, methyl 6-(trifluoroacetamido)-hexanoate, and 250 mL of dry tetrahydrofuran, was added 2.2 g (55 mmol, 1.1 equiv) of 60% sodium hydride. The mixture was stirred at room temperature for 30 minutes and then 10.25 g (49.0 mmol, 0.98 equiv) of the alkyl bromide, methyl 6-bromohexanoate, was added. The mixture was stirred at reflux for 3 hours, an additional 5.80 g (27.7 mmol, 0.55 equiv) of methyl 6-bromohexanoate was added, and the mixture was stirred at reflux for 70 hours. The mixture was cooled, diluted with 150 mL of 1N aqueous HCl and then extracted with ethyl acetate (3×100 mL). The organic extracts were combined, dried over magnesium sulfate, filtered and concentrated. The residue was diluted with 200 mL of methanol and then treated with 30 mL of 10N aqueous sodium hydroxide. The mixture was stirred at room temperature for 18 hours and then concentrated. The residue was diluted with 200 mL of deionized water and acidified to pH 1–2 with 37% concentrated HCl. The solution was washed with diethyl ether (3×100 mL). The aqueous phase was concentrated. The residue was diluted with 200 mL of methanol and reconcentrated. The subsequent residue was diluted with 250 mL of methanol, and HCl gas was bubbled through for 2–3 minutes followed by stirring at room temperature for 3 hours. The mixture was concentrated. The residue was diluted with 300 mL of methanol and filtered to remove inorganic salts. The filtrate was treated with 3 g of activated charcoal, filtered through Celite (manufactured by J. T. Baker) and concentrated. The residue, an off-white solid, was recrystallized from 100 mL of 2-propanol to afford 7.0 g of the product as a white solid. Concentration of the filtrate and further recrystallization of the residue yielded an additional 1.65 g of the product for a total of 8.65 g (56%): $^1$H-NMR (200 MHz, d$_6$-DMSO); 3.57 (s, 3H), 2.90–2.73 (m, 4H), 2.30 (t, 4H), 1.67–1.44 (m, 8H), and 1.37–1.20 (m, 4H) ppm.

Methyl 4-methylaminobutyrate hydrochloride. To a 1 L round bottom flask, charged with 30.0 g (195 mmol) of 4-methylaminobutyric acid and 500 mL of methanol, was bubbled HCl gas for 1–2 minutes. The mixture was stirred at room temperature for 3–4 hours and then concentrated to afford 32.5 g of the product as a foamy, off-white solid (99%): $^1$H-NMR (200 MHz, CD$_3$OD); 3.67 (s, 3H), 3.03 (t, 2H), 2.68 (s, 3H), 2.48 (t, 2H), and 2.03–1.87 (pentet, 2H) ppm.

4-Methylaminobutanol. To a 1 L round bottom flask, charged with 32.5 g (194 mmol) of the ester, methyl 4-methylaminobutyrate hydrochloride, was added 500 mL of 1M borane in tetrahydrofuran over a 1 hour period at 0° C. After the addition was complete, the mixture was refluxed for 20 hours, cooled to 0° C., and the excess borane was destroyed by careful addition of 100 mL of methanol. After all the methanol was added, the mixture was stirred at room temperature for 1 hour and then concentrated. The residue was diluted with 400 mL of methanol and then HCl gas was bubbled into the solution for 5 minutes. The mixture was refluxed for 16 hours. The mixture was cooled, concentrated and then diluted with 250 mL of deionized water. The product was initially free based by addition of 10N aqueous sodium hydroxide, to a pH of 9–9.5, and then by addition of 70 g of AG 1 X-8 anion exchange resin (hydroxide form) commercially available from BioRad, Richmond, Calif.), and by stirring the solution for 2 hours. The resin was filtered off and washed with 150 mL of deionized water. The aqueous filtrates were combined and concentrated. The residue was diluted with 200 mL of 2-propanol and filtered. The collected solids were rinsed with 100 mL of 2-propanol. The organic filtrates were combined and concentrated. The residue was distilled under reduced pressure to afford 12.85 g of the product as a colorless oil (bp 68° C. at 0.1–0.2 mm HG; 64%) : $^1$H-NMR (200 MHz, D$_2$O); 3.52 (t, 2H), 2.56 (t, 2H), 2.31 (s, 3H), and 1.65–1.43 (m, 4H) ppm.

4-(N-Methyl-trifluoroacetamido)-1-butanol. To a 250 mL round bottom flask, charged with 10.0 g (96.9 mmol) of the amine, 4-methylaminobutanol, in 100 mL of dry methanol, was added 17.5 mL (147 mmol) of ethyl trifluoroacetate. The mixture was stirred at room temperature for 24 hours and then concentrated to afford 18.55 g of the product as a near colorless oil (96%): $^1$H-NMR (200 MHz, D$_2$O); 3.63 and 3.50 (2t's, 4H), 3.20 and 3.05 (d and s, 3H), and 1.82–1.47 (m, 4H) ppm.

1-(p-Toluenesulfonyloxy)-4-(N-methyl-trifluoroacetamido)butane. To a 1 L dry round bottom flask, charged with 17.0 g (85.4 mmol) of the alcohol, 4-(N-methyl-trifluoroacetamido-l-butanol, in 400 mL of methylene chloride, was added 17.1 g (89.7 mmol, 1.05 equiv) of toluenesulfonyl chloride followed by 30 mL (213 mmol, 2.5 equiv) of triethylamine at 0° C. over a 10 minute period. The mixture was stirred at 0° C. to room temperature for 15 hours and then washed with 5% v/v aqueous HCl (3×200 mL). The organic phase was dried over magnesium sulfate, filtered and concentrated. The residue was chromatographed on silica gel, eluting with 50:50 hexane/methylene chloride and then with methylene chloride, to give 25.1 g of the product as a pale yellow oil (83%): $^1$H-NMR (200 MHz, CDCL$_3$); 7.80 (d, 2H), 7.37 (d, 2H), 4.07 (m, 2H), 3.41 (m, 3H), 3.09 and 2.98 (q and s, 3H), 2.45 (s, 3H), and 1.68 (m, 4H) ppm: TLC (methylene chloride) R$_f$=0.31.

1-S-(2,3,4,6-tetra-O-acetyl-beta-D-galacto-pyranosyl)-2-thiopseudourea hydrobromide. To a 250 mL round bottom flask, charged with 5.08 g (60.8 mmol, 1.09 equiv) of thiourea and 36 mL of acetone, was added 25.0 g (66.7 mmo9l) of tetra-acetyl-alpha-D-galactopyranosyl bromide. The mixture was stirred at reflux for 15–20 minutes and then cooled on ice. The mixture was filtered into a Buchner funnel and rinsed with 25 mL of ice cold acetone. The solids were treated with 50 mL of acetone, refluxed for 15 minutes, cooled on ice, and filtered. The solids were rinsed with 25 mL of cold acetone, air dried and then dried under vacuum to give 22.6 g of the product as a white solid (76%): $^1$H-NMR (200 MHz, d$_6$-DMSO); 9.4–9.0 (broad d, 4H), 5.63 (d, 1H), 5.38 (d, 1H), 5.23 (dd, 1H), 5.09 (t, 1H), 4.40 (t, 1H), 4.04 (dd, 1H), 2.13 (s, 3H), 2.08 (s, 3H), 2.00 (s, 3H), 1.93 (s, 3H) ppm.

4-(N-Methylaminobutyl)-1-thio-beta-D-galactopyranoside. To a 500 mL round bottom flask, charged with 20.7 g (42.5 mmol, 1.07 equiv) of the thiopseudourea hydrobromide prepared as described above in 70 mL of deionized water, was added 6.4 g (46.3 mmol, 1.16 equiv) of potassium carbonate and 4.7 g (45.2 mmol, 1.13 equiv) of sodium bisulfite followed immediately by 14.1 g (39.9 mmol, 1.0 equiv) of the tosylate, 1-(p-toluenesulfonyloxy)-4-(N-methyl-trifluoroacetamido)butane, in 70 mL of acetone. The mixture was stirred at room temperature for 16 hours. The mixture was diluted with 50 mL of brine and extracted with ethyl acetate (3×200 mL). The organic extracts were combined, dried over magnesium sulfate, filtered and concentrated. The residue was chromatographed on silica gel, eluting first with 75% methylene chloride/hexane, followed by methylene chloride, then with 2% methanol/methylene chloride and finally with 10% methanol/methylene chloride. Fractions containing alkylation product with different degrees of acetylation were combined and concentrated. The residue was diluted with 250 mL of methanol and 150 mL of deionized water and treated with 110 g of AG-1 X-8 resin (hydroxide form; 2.6 m equiv/g dry weight) commercially available from BioRad. The mixture was stirred at room temperature for 18 hours. The mixture was filtered, and the resin was rinsed with methanol (2×150 mL). The filtrates were combined and concentrated to afford 6.1 g of product (54%): $^1$H-NMR (200 MHz, D$_2$O); 4.38 (d, 1H), 3.88 (d, 1H), 3.69–3.41 (m, 5H), 2.82–2.64 (m, 4H), 2.43 (s, 3H), and 1.68–1.57 (,4H) ppm.

N-BOC-Bis-methylester. To 1.00 g (3.23 mmol) of the amine hydrochloride, N,N-bis-(6-methoxycarbonyl-hexyl)amine hydrochloride prepared as described above, was added 1.5 mL (10.6 mmol) of triethylamine followed by 875 mg (3.55 mmol, 1.1 equiv) of BOC-ON, 2-(tert-butoxycarbonyloxyimino)-2-phenylacetonitrile. The mixture was stirred at room temperature for 18 hours and then concentrated. The residue was diluted with 100 mL of ethyl acetate and washed with 1N aqueous hydrochloric acid (3×50 mL), followed by saturated aqueous sodium bicarbonate (2×50 mL). The organic phase was dried over magnesium sulfate, filtered and concentrated. the residue was chromatographed on silica gel, eluting with 15% (percentage by volume) ethyl acetate/hexane. Chromatographic fractions containing product were combined and concentrated to afford 990 mg of product as a near colorless oil (83%).

N-BOC-Bis-acid. To 980 mg (2.62 mmol) of the diester prepared in the previous step in 10 mL of methanol was added 5.8 mL of 1N aqueous sodium hydroxide (5.8 mmol). The mixture was stirred at room temperature for 16 hours and then concentrated. The residue was diluted with 30 mL of deionized water and acidified to pH 1.5–2. The mixture was extracted with ethyl acetate (6×50 mL). The organic extracts were dried over magnesium sulfate, filtered and concentrated. The residue was chromatographed on reverse phase C-18 silica gel commercially available from J. T. Baker, eluting with 65% methanol/water. Chromatographic fractions containing product were combined and concentrated to afford 851 mg of product as a near colorless oil (94%).

N-BOC-Tetra-methyl ester. To 825 mg (2.39 mmol) of the bis-acid prepared as described above in 35 mL of dry dimethylformamide, was added 1.75 g (5.65 mmol, 2.36 equiv) of amine hydrochloride, N,N-bis-(6-methoxycarbonylhexyl)amine hydrochloride, and 3.0 mL of triethylamine followed by 2.4 g (5.4 mmol, 2.3 equiv) of BOP. The mixture was stirred at room temperature for 17 hours and then concentrated. The residue was diluted with 100 mL of ethyl acetate and washed with 1N hydrochloric acid (3×50 mL) followed by washing with aqueous sodium bicarbonate (2×50 mL). The organic phase was dried over magnesium sulfate, filtered and concentrated. The residue was chromatographed on silica gel, eluting with ethyl acetate. Chromatographic fractions containing product were combined and concentrated to afford 1.63 g of the product as a near colorless oil (80%).

N-BOC-Tetra-acid. To a solution of 1.41 g (1.65 mmol) of tetra-methyl ester prepared as described above in 25 mL of methanol was added 7.4 mL (7.4 mmol) of 1N aqueous sodium hydroxide. The mixture was stirred at room temperature for 22 hours and then concentrated. The residue was diluted with 30 mL of deionized water and acidified to pH 2 with 1N aqueous hydrochloric acid. The mixture was extracted with 3:1 (ratio by volume) ethyl acetate/isopropanol (3×100 mL). The organic extracts were concentrated. The residue was chromatographed on reverse phase C-18 silica gel, eluting initially with 50:50 (ratio by volume)

methanol/water and eventually with 75:25 methanol/water. Chromatographic fractions containing product were combined and concentrated to afford 1.19 g of the product as a colorless oil (90%).

N-BOC Octa-methyl ester. To a mixture of 501 mg (0.626 mmol) of tetra-acid prepared as described above and 30 mL of dry dimethylformamide was added 968 mg (3.12 mmol, 5.0 equiv) of amine hydrochloride, N,N'-bis-(6-methoxycarboxyhexyl)amine hydrochloride, and 2.0 mL (14.2 mmol) of triethylamine, followed by 1.22 g (2.76 mmol, 4.6 equiv) BOP. The mixture was stirred at room temperature for 19 hours and then concentrated. The residue was diluted with 75 mL of ethyl acetate and washed with 1N aqueous hydrochloric acid (2'50 mL). The organic phase was dried over magnesium sulfate, filtered and concentrated. The residue was chromatographed on reverse phase C-18 silica gel, eluting initially with 60:40 methanol/water and eventually with 90:10 methanol/water. The chromatographic fractions containing product were combined and concentrated to afford 715 mg of the product as a colorless oil (63%).

N-BOC Octa-acid. To a solution of 715 mg (0.393 mmol) of octa-methyl ester prepared as described above in 20 mL of methanol was added 6 mL of 1N aqueous sodium hydroxide (6 mmol) and 5 mL of deionized water. The mixture was stirred at room temperature for 16 hours and then concentrated. The residue was diluted with 20 mL of deionized water, and the solution was acidified to pH 1.5–2.0. The mixture was concentrated, and the residue was chromatographed on reverse phase C-18 silica gel, eluting initially with 50:50 methanol/water and eventually with 80:20 methanol/water. The chromatographic fractions containing product were combined and concentrated to afford 647 mg of the product as a near colorless oil (96%).

The above procedure is designed for the formation of a galactose cluster of 8 galactose residues. The four galactose version can be made in accordance with this procedure by proceeding from the tetra acid to the galactose derivatization step, which is described below for the 8-galactose cluster. Similarly, 16, 32, etc. galactose cluster constructs can be prepared in accordance with the present invention by introduction of more iterations of the methyl ester and acid formation steps. More specifically, the 16-methyl ester construct, the 16-acid, the 32-methyl ester and so on would be prepared essentially as described above for the tetra and octa forms. When the desired number of acid residues are formed, the galactose derivatization step is employed, with the proportions of the components adjusted to accommodate the number of acid residues.

N-BOC-Octa-galactosyl construct. To a mixture of 161 mg (94 mmol) of octa-acid prepared as described above and 225 mg (906 micromol, 9.64 equiv) of galactose amine, 4-N-methylaminobutyl)-1-thio-beta-D-galactopyranoside, in 8 mL of dry dimethylformamide was added 0.5 mL (3.54 mmol) of triethylamine followed by 371 mg (839 micromol, 8.4 equiv) of BOP. The mixture was stirred at room temperature for 17 hours and then concentrated. The residue was chromatographed on reverse phase C-18 silica gel, eluting initially with 40:60 methanol/water and finally with 70:30 methanol/water. The chromatographic fractions containing product were combined and concentrated to afford 170 mg of the product as a near colorless oil (47%).

Octa-galactosyl amine. To 170 mg of the N-BOC-octa-galactosyl construct prepared as described above was added 5 mL of trifluoroacetic acid. The mixture was stirred at room temperature for 10 minutes and then concentrated. The residue was diluted with 10 mL of methanol and reconcentrated. The residue is used without further purification.

B. Extender-Galactose Cluster Preparation

Figure 6:
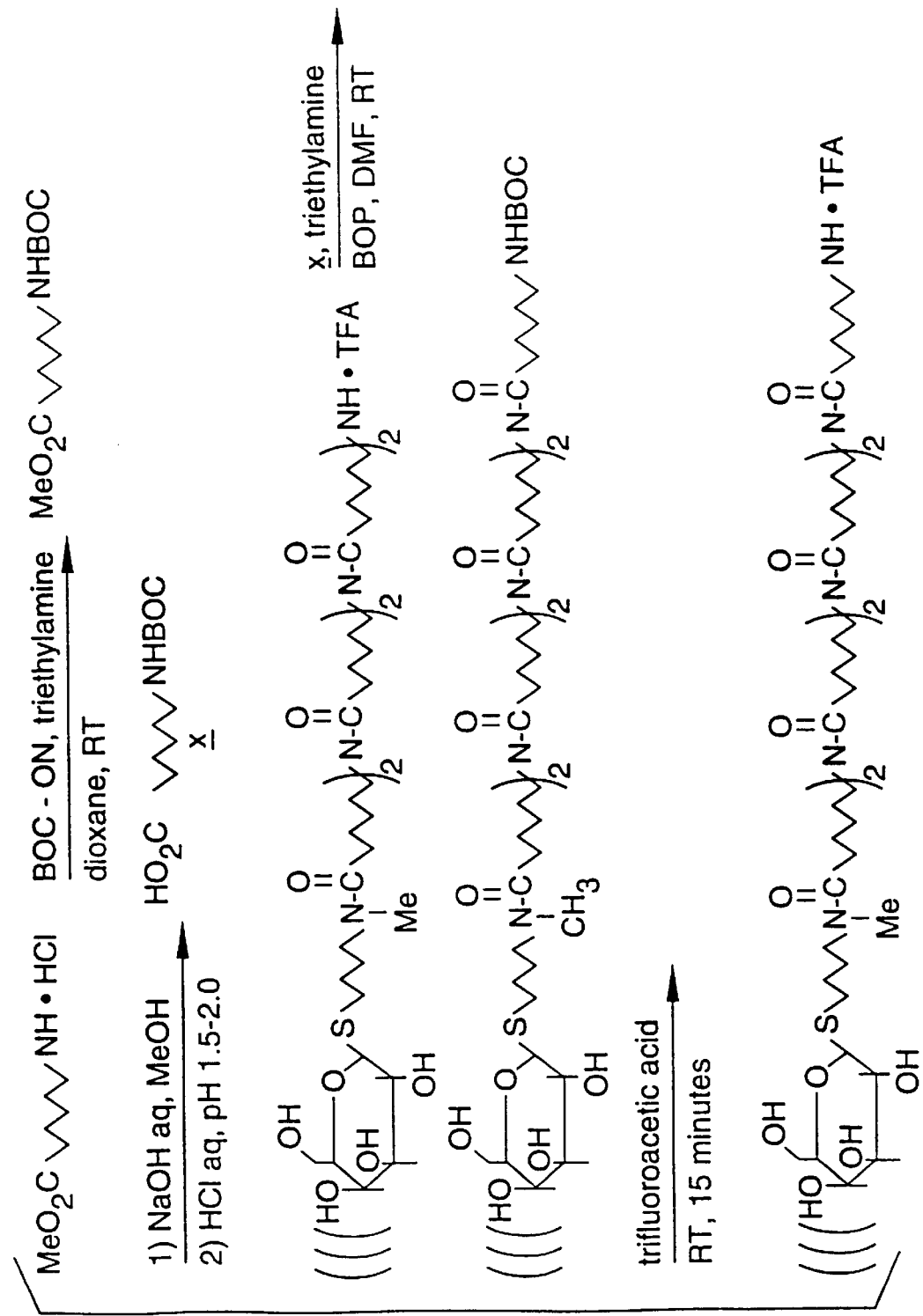
FIG. 6 schematically shows the synthesis of an extended eight galactose-containing galactose cluster.
Figure 7:
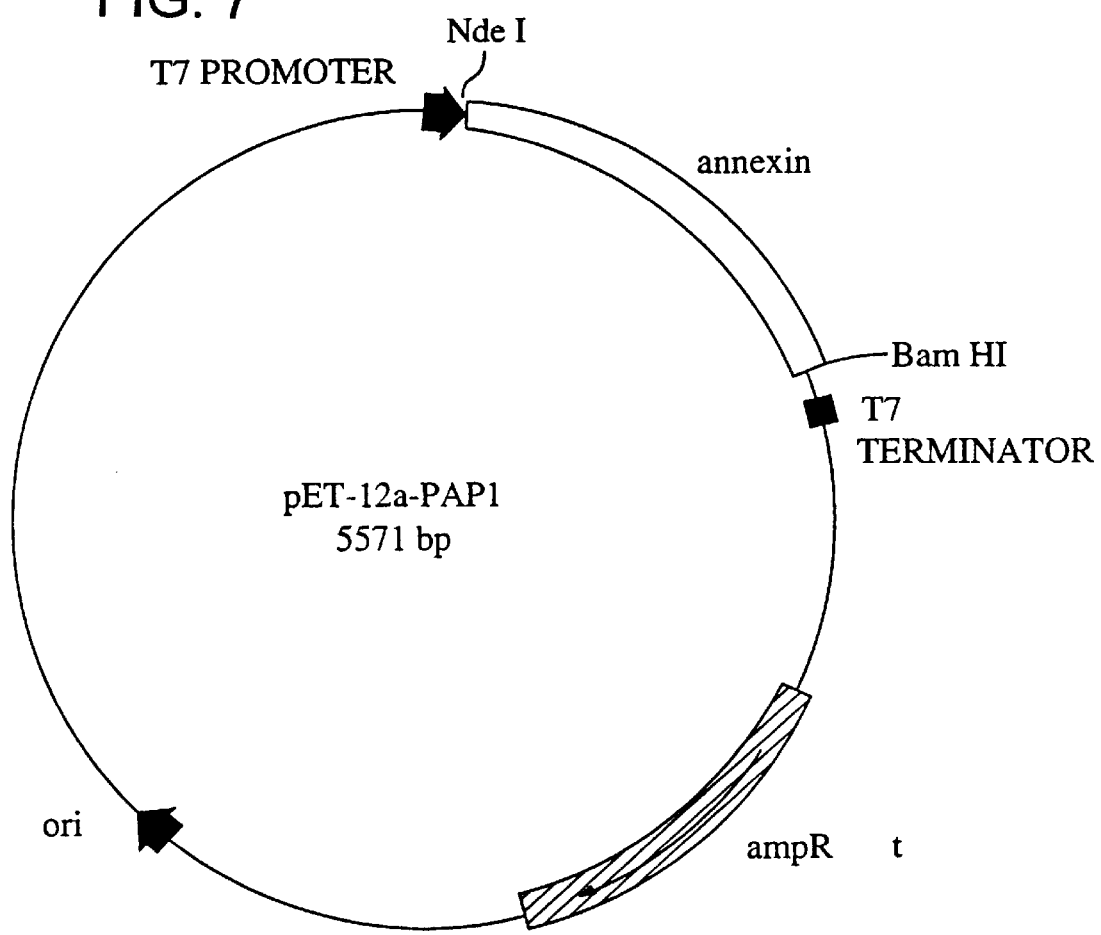
FIG. 7 schematically represents a pET-12a plasmid Map.
Figure 8:
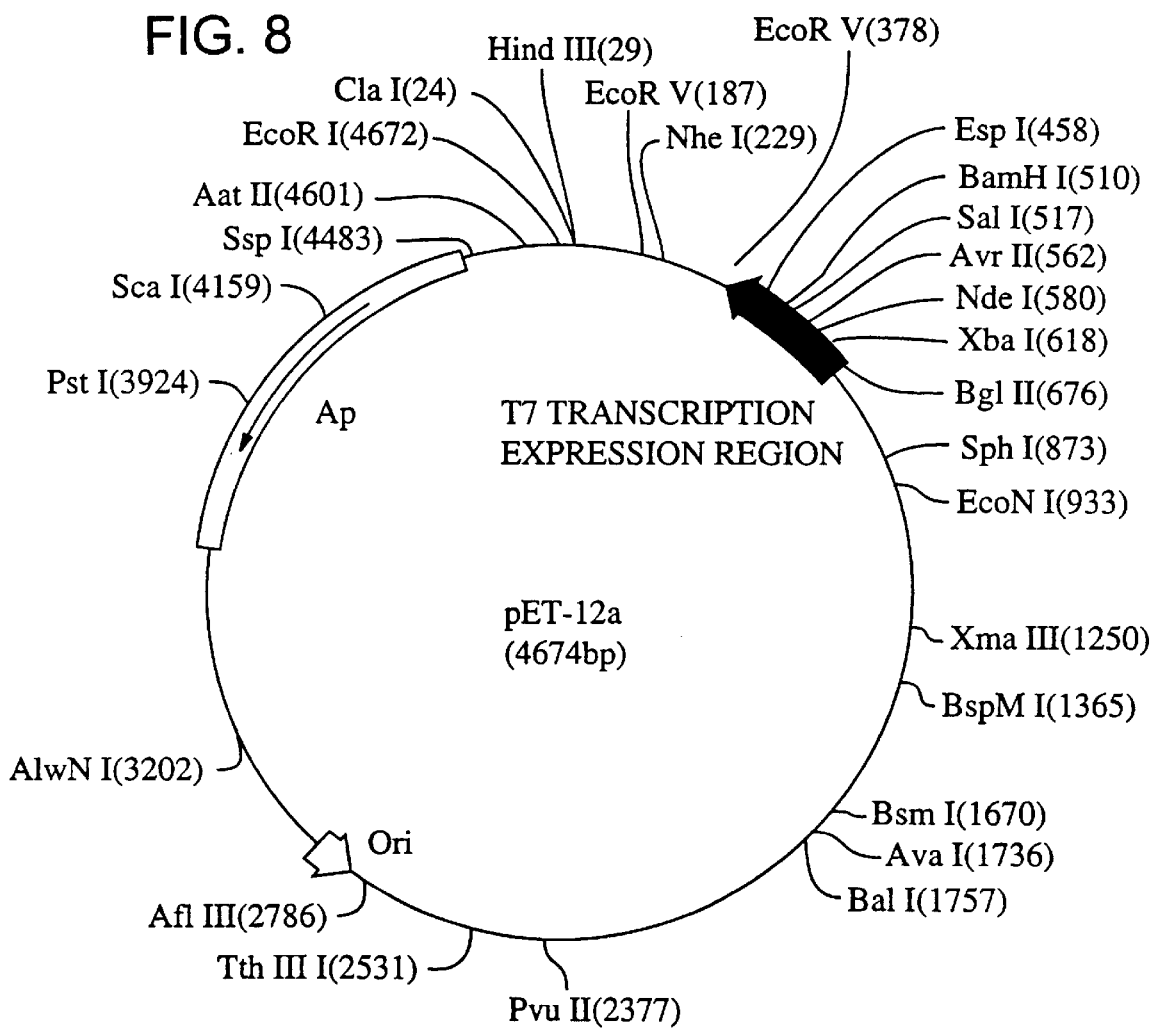
FIG. 8 schematically represents pET-12a-PAP1,3/7/94, clone 1.

This procedure is schematically shown in FIG. 6.

Methyl 6-(N-BOC)-aminocaproate. To a mixture of amine hydrochloride, methyl-6-aminohexanoate hydrochloride, prepared as described above is added 1.1 equivalents of BOC-ON followed by 2–3 equivalents of triethylamine. The mixture is stirred at 15–30° C. for 16–24 hours and the concentrated. The residue is dissolved in ethyl acetate and washed with 1N aqueous hydrochloric acid and then with saturated aqueous sodium bicarbonate. The organic phase is dried over magnesium sulfate, filtered and concentrated via reduced pressure rotary evaporation. The residue is chromatographed on silica gel, eluting with 25% ethyl acetate/hexane. The chromatographic fractions containing the product are combined and concentrated to afford the product.

6-(N-BOC)-aminocaproic acid. To a solution of the methyl ester, methyl 6-(N-BOC)-aminocaproate, in methanol is added 1.5 equivalents of 1N aqueous sodium hydroxide. The mixture is stirred at 15–30° C. for 16–24 hours and then concentrated. The residue is diluted with deionized water and extracted with ethyl acetate. The organic extracts are combined, dried over magnesium sulfate, filtered and concentrated. The residue is chromatographed on silica gel, eluting initially with 25% ethyl acetate/hexane and finally with 100% ethyl acetate. The chromatographic fractions containing the product are combined and concentrated to afford the product.

N-BOC extended octa-galactosyl construct. To a solution of the octa-galactosyl amine prepared as described above in dimethylformamide and 1.5–3 equivalents of 6-(N-BOC)-aminocaproic acid is added 4–6 equivalents of triethylamine followed by 1.1–1.5 equivalents of BOP. The mixture is stirred at 15–30° C. for 4–24 hours and then concentrated. The residue is diluted with deionized water, and the pH is adjusted to 1.5–2.0 by addition of 1N aqueous hydrochloric acid. The mixture is washed with ethyl acetate. The aqueous phase is concentrated, and the residue is chromatographed on reverse phase C-18 silica gel, eluting initially with 50:50 methanol/water and finally with 65:35 methanol/water. The chromatographic fractions containing product are combined and concentrated to afford the product.

Amine extended octa-galactosyl construct,. To the N-BOC protected amine prepared in the previous step is added trifluoroacetic acid. The mixture is stirred at 15–30° C. for 10 minutes and then concentrated. The residue is diluted with methanol and reconcentrated to afford the product which is used without further purification.

C. Conjugation of Galactose Cluster with Chelating Compound and Annexin Components Octa-galactosyl-chelating compound construct. To a mixture of amine extended octa-galactosyl amine, 1.2 equivalents of N,N'-bis(2-disulfidyl-4-hydroxycarbonylphenyl)-1, 3-propyldiamine mono-(methyl-aminocaproate)adduct, and 5 equivalents of triethylamine in dimethylformamide is added 1.1 equivalents of BOP.

The mixture is stirred at 15–30° C. for 2 to 24 hours and then concentrated. The residue is diluted with deionized water, and the pH is adjusted to 2.5 by the addition of 1N aqueous hydrochloric acid. The mixture is washed with ethyl acetate. The aqueous phase is concentrated. The residue is chromatographed on reverse phase C-18 silica gel. The fractions containing the product are combined and concentrated to give the product.

Octa-galactosyl-chelating compound carboxylic acid construct. To a methanolic solution of the ester bearing octa-galatosyl-chelating compound construct prepared previously is added 4–5 equivalents of 1N aqueous sodium hydroxide. The mixture is stirred at 15–30° C. for 16–24 hours. The mixture is concentrated, and the residue is diluted with deionized water. The pH of the resulting solution is adjusted to approximately 2.5, and the solution is reconcentrated. The residue is chromatographed on reverse phase C-18 silica gel. The fractions containing the product are combined and concentrated to afford the product.

Annexin V-chelating compound-octa-galactosyl construct. The octa-galactosyl-chelating compound carboxylic acid construct is offered to annexin V in molar ratios of 30:1, 15:1, 5:1 and 2:1. The conjugation of annexin V is carried out via activation of the carboxylic acid functional group of the galactose cluster-chelating compound construct with benzotriazol-1-yl-oxy-tris-(dimethylamino)phosphonium hexafluorophosphate (BOP). To the galactose cluster-chelating compound construct in DMF, an equimolar concentration of BOP in DMF is added. Annexin V in 0.05M HEPES buffer (commercially available from Sigma Chemical Co., St. Louis, Mo.), pH 7.4 is added to the reaction mixture followed by addition of 0.5M borate buffer, pH 8.5. The DMF concentration in the reaction mixture is maintained between 5–20%. The solution is mixed for 1 hour at room temperature by tumbling the reaction vessel, and is then allowed to stand at room temperature overnight (approximately 18–24 hours). The reaction mixture is then diluted with PBS, transferred to dialysis tubing (6000–8000 molecular weight cut off), and dialyzed for 24 hours against PBS. After removing the material from the dialysis bag, the solution is filtered through a 0.2 micrometer syringe filter. All of the offering levels are conducted analogously.

D. Characterization of Galactose Cluster-Chelating Compound-Annexin V Conjugate

Protein concentration is determined using $A_{280}$ of 0.6 for a 1 mg/mL solution of annexin V. The number of galactose residues per molecule of annexin V is determined by measuring the total number of reactive amines on Annexin V before and after reaction with galactosyl cluster-chelating compound conjugate using trinitro-benzenesulfonic acid, as described by Habeeb, *Analytical Biochemistry*, 14: 328–36, 1966. The ability of galactose-chelating compound-annexin V to bind to activated platelets is assessed by determining its ability to inhibit the binding of unmodified, I-125-radiolabeled annexin V to freshly isolated human platelets, following the method of Thiagarajan and Tait, *J. Biol. Chem.*, 265: 17,240–43, 1990.

E. Radiolabeling Procedure for use in Post-Formed Chelate Conjugation Method

Method A: Stannous gluconate kits are prepared containing 5 mg sodium gluconate, 100 micrograms stannous chloride, 1.0 mg (1 mg/mL) of galactose cluster-chelating compound-annexin V, and 0.1 to 1.0 mg of lactose. The pH is maintained between 5 and 7 using HCl, acetic acid or NaOH. To the stannous gluconate kit is added 1.0 mL sodium pertechnetate (Tc-99m) with a specific activity of about 50 mCi. The vial is incubated at 25–37° C. for 5–30 minutes. The percent formation of labeled conjugate, remaining $TcO_4$, and hydrolyzed reduced technetium is determined by ITLC in 12% TCA as developing solvent.

Method B: Stannous tartrate kits are prepared in an evacuator vial under nitrogen to contain 0.5 mL of disodium tartrate (10 mg/mL) and 0.1 mL stannous chloride (1.0 mg/mL in ethanol). The pH of the solution is kept between 5 and 7, preferably 6.0. To this stannous tartrate solution is added 1.0 mL of sodium pertechnetate (50 mCi), and the solution is allowed to stand at room temperature. In and evacuated vial, 200 microliters of sodium phosphate (0.5M, pH 8 or 10) and 1.0 mL of galactose cluster-chelating compound-annexin V conjugate (1.0 mg/mL) are added successively. Then Tc-99m-tartrate (50 mCi) is added, and the vial is incubated at 25–37° C. for 5–30 minutes. The percent formation of labeled conjugate, remaining $TcO_4$, and hydrolyzed reduced technetium is determined by ITLC in 12% (w/v) trichloroacetic acid as developing solvent.

Constructs prepared in accordance with this Example are tested in accordance with the procedures set forth above (Example III and Example IV(E)) to verify usefulness in clot imaging applications, for example.

EXAMPLE VII

Annexin-Galactose Cluster Conjugates Trifunctional Linker Approach

A. Chelating Compound Preparation

Figure 4:
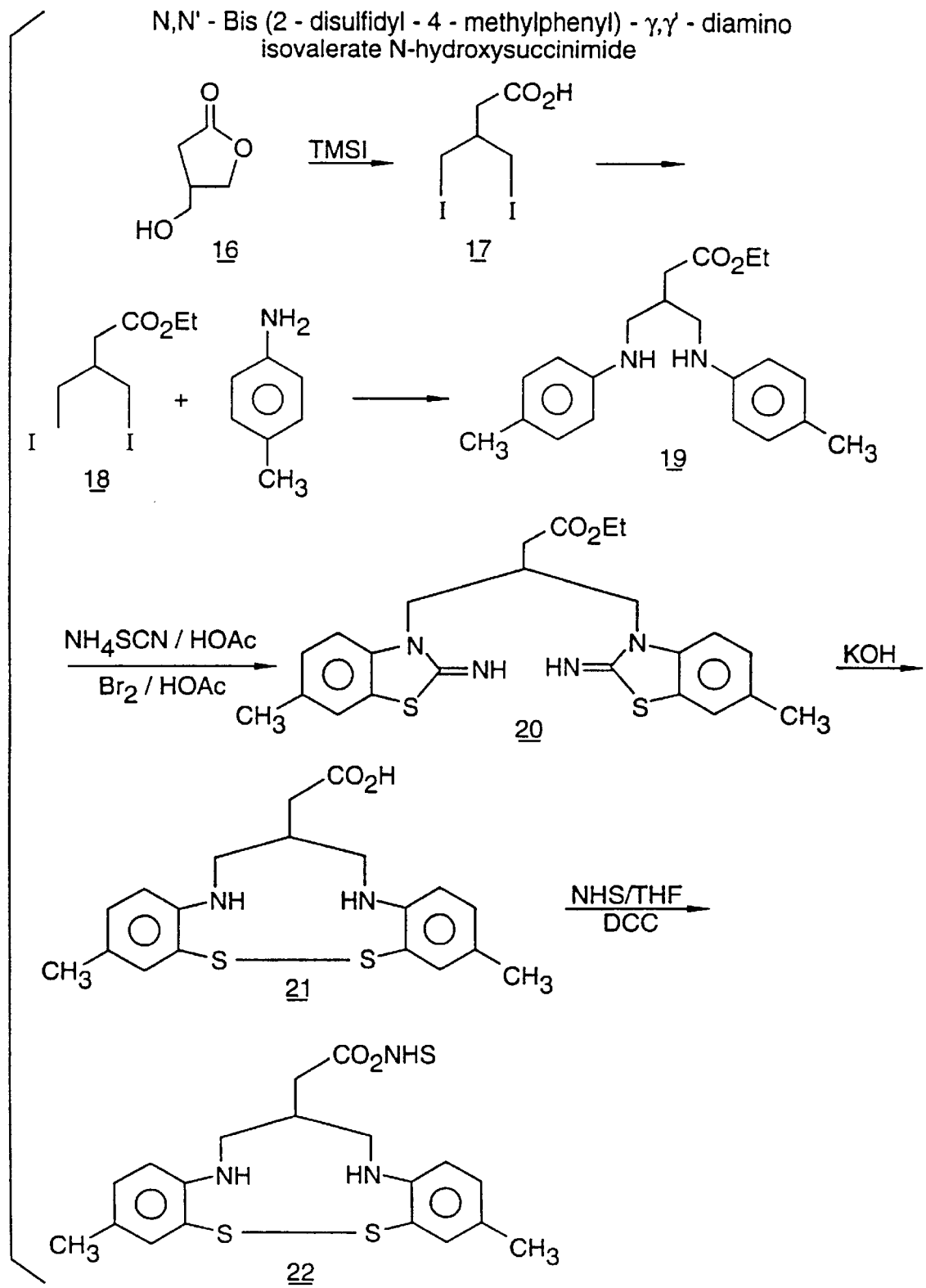
FIG. 4 schematically shows the synthesis of N,N'-bis(disulfidyl-4-methylphenyl)-gamma,gamma'-diamino-isovalerate N-hydroxysuccinimide.

Production of chelating compound N,N'-bis(2-disulfidyl-4-methylphenyl)-gamma,gamma'-diamino-isovalerate N-hydroxysuccinimide, as shown schematically in FIG. 4.

3-Iodomethyl-4-iodobutyric acid: To a solution of 1.61 g (10 mmole) 3-hydroxymethyl-4-butanolide (prepared by the procedure of Kinoshita and Hirano, *J. Hetrocyclic Chem.*, 29: 1025, 1992) in 100 mL carbon tetrachloride is added 8 g (40 mmole) of iodotrimethylsilane. The reaction mixture is heated at 50° C. for 12 hours under nitrogen. The mixture is diluted with chloroform and washed with water (3×100 mL), 5% aqueous sodium thiosulfate (100 mL), 10% aqueous sodium bicarbonate and brine. The organic layer is dried over magnesium sulfate, filtered and evaporated to give the desired crude product. The crude product is purified by silica gel chromatography (ethyl acetate-hexane=3:7 as the eluting solvent) to give 3-iodomethyl-4-iodobutyric acid.

Ethyl-3-iodomethyl-4-iodobutyrate: A solution of 2.831 g (8 mmole) 3-iodomethyl-4-iodobutyric acid in 80 mL ethanol is saturated with HCl gas at 0° C. After stirring the solution at room temperature for two days, the solvent is removed under vacuum, and the residue is dissolved in dichloromethane. The dichloromethane layer is washed with 10% aqueous sodium bicarbonate (3×100 mL), water (1×100 mL) and brine. The separated dichloromethane layer is dried over with magnesium sulfate, filtered and evaporated to give ethyl-3-iodomethyl-4-iodobutyrate.

Ethyl-gamma,gamma'-di(4-methylanilino)isovalerate: A stirred solution of 7.5 g (70 mmole) 4-toluidine, 2.764 g (7 mmole) ethyl-3-iodomethyl-4-iodobutyrate and 0.588 g (7 mmole) sodium bicarbonate in 30 mL dry dimethyl sulfoxide is heated at 100° C. for 3 hours under nitrogen. The cooled mixture is poured onto 400 mL ice water with stirring. The resulting precipitate is collected by filtration. The remaining 4-toluidine in the precipitate is removed by washing with aqueous acetic acid several times. The product is obtained by recrystallization of the washed precipitate in heptane.

Ethyl-gamma,gamma'-[1,3-di(2-imino-6-methyl benzthiazolyl-3)]isovalerate: To a magnetically stirred suspension of 2.0 g (6.5 mmole) ethyl-gamma,gamma'-di(4-methylanilino)isovalerate in 250 mL glacial acetic acid is added ammonium thiocyanate (3.5 g, 0.046 mole) followed by the dropwise addition of a solution of bromine (7.27 g, 0.046 mole) in 50 mL glacial acetic acid. After addition is complete, stirring is continued overnight. The yellow precipitate of dihydrobromide salt is filtered and dried. The dried solid is then dissolved in hot water and the benzothiazole free base is liberated with saturated sodium bicarbonate solution. The white solid is filtered and dried to give crude product which is used without further purification.

N,N'-Bis(2-disulfidyl-4-methylphenyl)-gamma,gamma'-diaminoisovaleric aid: To a suspension of ethyl-gamma, gamma'-[1,3-di(2-imino-6-methyl benzthiazolyl-3)] isovalerate in 40 mL distilled water, solid potassium hydroxide pellets (20.0 g, 0.037 mole) are added, and the resulting solution is heated at 120° C. for 15–24 hours. After several hours of heating, the suspension becomes a clear solution. The reaction mixture is cooled in an ice bath and acidified with 5.0N acetic acid to pH 5.0, and the aqueous solution is extracted with three 100 mL portions of ethyl acetate. The combined ethyl acetate extracts are dried over anhydrous sodium sulfate and filtered. Solvent from the filtrate is removed under reduced pressure to give crude product. This crude product is chromatographed on silica gel column using a 20:80 mixture of ethyl acetate:hexane with 1% acetic acid as eluting solvent to give the product as a crystalline yellow solid.

N,N'-Bis(2-disulfidyl-4-methylphenyl)-gamma,gamma'-diaminoisovalerate N-hydroxysuccinimide: N,N'-Bis(2-disulfidyl-4-methylphenyl)-gamma,gamma'-diaminoisovaleric acid is reacted with N-hydroxysuccinimide (NHS) and dicyclohexylcarbodiimide (DCC) in either tetrahydrofuran (THF) or dimethylformamide (DMF) at room temperature. After stirring overnight at room temperature, the solvent is removed, and the crude product is purified by column chromatography on silica gel.

B. Conjugate formation

This chelating compound is amenable to use with a suitable trifunctional linker to form a radiolabeled annexin-galactose cluster conjugate of the present invention as described below.

Commercially available N-epsilon-t-BOC-lysine (Sigma Chemical Company) is converted, using trifluoroacetic anhydride, to its N-alpha-trifluoroacetamide adduct. Activation of the carboxylic acid functionality, for example with BOP (benzotriazol-1-yloxy-tris(dimethyl-amino)-phosphonium hexafluorophosphate) commercially available from Aldrich Chemical Co., and reaction of the activated moiety with the single available amine on a galactose cluster, e.g., formed as described above, affords a galactose cluster-trifunctional linker species. The alpha-amine of lysine trifunctional linker component of the galactose cluster-trifunctional linker species is deblocked using methanolic sodium hydroxide. Reaction with the N-hydroxysuccinimide ester of the chelating compound molecule formed as set forth in part A of this example affords a galactose cluster-chelating compound trifunctional linker species. Deprotection of the epsilon amine of the lysine trifunctional linker component using trifluoroacetic acid, followed by reaction with succinic anhydride provides an available carboxylic acid functionality through which the annexin may be conjugated following activation of the carboxylic acid (e.g., with BOP).

EXAMPLE VIII

Method for Producing a Cell Expression Clone of Annexin V

A parent clone, HPAP1.6, is described in Funakoshi et al., "Primary Structure of Human Placental Anticoagulant Protein", *Biochemistry*, Vol. 26, pp. 8087–8092 (1987). Polymerase chain reaction (PCR) was used to amplify the annexin gene from the λHPAP1.6 parent clone. The sense primer (CAT ATG GCA CAG CTT CTC A) (SEQ ID NO:2) contained an NdeI restriction site (underlined) and the first 16 nucleotides of the annexin leader sequence, beginning with the ATG start codon. The antisense primer (GGA TCC TTA GTC ATC TTC TCC ACA) (SEQ ID NO:3) encoded the end of the coding sequence, a stop codon (bold) and BamHI restriction site (underlined). The PCR product and plasmid pET-12a (FIG. 2) obtained from Novagen (Palo Alto, Calif.) were each digested with NdeI and BamHI and ligated together with T4 DNA ligase. A portion of the ligation solution was transformed into an *E. Coli* host strain and selected on nutrient agar plates containing ampicillin. Plasmid from the resultant clone was designated pET-12a-PAP1-E287G, 7/16/93, clone 1. Dideoxy DNA sequence analysis showed that this plasmid contained DNA that matched the wild-type annexin sequence except for two mutations [855 G→A (silent); 860 A→G (converts Glu-287 to Gly-287)].

The sequence changes present in pET-12a-PAP-E287G, 7/16/93, clone 1 were corrected in the following manner. The plasmid was digested with restriction enzymes SfuI and BamHI which excised a fragment of approximately 240 base pairs containing both mutations. The fragment was replaced with a 240 base pair fragment from an independent clone known to contain the wild-type sequence. The DNAs were ligated and transformed into an *E. Coli* host. *E. Coli* colonies containing plasmid DNA were selected on ampicillin containing nutrient agar plates. The resulting clone harbored plasmid pET-12a-PAP1, 3/7/94, clone 1 (FIG. 3). DNA sequencing confirmed that the annexin coding sequence on the plasmid matched the wild-type sequence exactly.

The host strain BL21(DE3), received from Novagen, was transformed with the plasmid pET-12A-PAP1, 3/7/94, clone 1. A glycerol stock was made of the resulting transformant BL21(DE3)(pET-12A-PAP1, 3/7/94, clone 1) and stored at ≤-65° C.

Growth of *E. coli* BL21(DE3)(pET-12A-PAP1, 3/7/94, clone 1) in liquid culture at 37° C. resulted in accumulation of the Annexin V protein in the *E. coli* cytoplasmic space.

EXAMPLE IX

Procedure for Modification (Replacement of an amino acid) of Annexin V

The plasmid pET-12a is described above in Example VIII. Annexin amino acid variant genes were placed between the NdeI and BamHI restriction sites on the pET-12a plasmid.

An independent modification of annexin V was created by site-directed amino acid alteration, utilizing PCR amplification. To accomplish this alteration, oligonucleotides which anneal in the antisense direction of the 3' end of annexin were created. The particular alteration of annexin V, described herein, is a replacement of a cysteine residue (position 316) with alanine, or another non-sulfur containing amino acid, such as serine. In order to achieve this alteration, the nucleotide sequence was changed from TGT to GCA. The oligonucleotide includes a BamHI restriction enzyme site and a stop codon.

The sense oligonucleotide anneals within the T7 promoter region of pET-12a, just upstream from the NdeI restriction site or the 5' end of annexin V. The following are the anti-sense and sense oligonucleotide sequence, respectively:

(N×x168 Cys TO Ala antisense)

5' GTACCTGGATCCTTAGTCATCTTCTC-CGCGAGCAGCAGAAGAGCTTTCTT 3' (SEQ ID NO:5).

and (T7 sense)

5' CGAAATTAATACGACTCACTATAGGG 31' (SEQ ID NO:5).

The N×168 and T7 oligonucleotides were synthesized using DNA synthesizer, model 381A (Applied Biosystem Inc., model 381A, Foster City, Calif.). After synthesis was complete both oligonucleotides were deprotected as per appendix 5 of the above manufacturer's protocol. Purification was done using Sephadex™ G-25 column (Pharmacia, Uppsala, Sweden).

PCR reactions were done using UlTma™ polymerase (Perkin Elmer, Norwalk, Conn.). The reactions were performed using approximately long of pET12a-annexin V template, 30 pMol of T7 and Nx168 oligonucleotides, and 0.4 mM of each nucleotide. Mineral oil overlay was included. The reactions were placed in a Coy temperature cycler model 110P and incubated for five minutes at 94° C. Approximately 2 minutes into the incubation, 0.5 units of polymerase was added. The reactions were then cycled 30 times at 94° C. for 30 seconds, 55° C. for one minute, and 74° C. for one minute. The reactions were then incubated for 5 minutes at 74° C., and then soaked at 15° C.

The resulting annexin-ala substituted gene was then purified using a DNA purification kit (Promega Magic™ PCR Preps DNA Purification System, Madison, Wiss.) according to manufacturer's protocol.

Annexin-ala and pET-12a were then digested with NdeI and BamHI (Gibco/BRL, Gaithersburg, Md.) restriction enzymes. Digested products were then purified by agarose gel electrophoresis. Appropriate bands were excised and purified using GeneClean II® Kit (Bio 101, Inc., La Jolla, Calif.) according to manufacturer's protocol. The annexin-ala and pET-12a were then ligated with T4 DNA ligase (Promega) for 12–18 hours at 4° C.

Annexin-ala-pET-12a were transformed into *E. coli* strain DH5 Max. efficiency competent cells (Gibco/BRL). Any other suitable host strain for the pET-12a plasmid may also be used. The *E. coli* transformed cells are placed on LB agar (Gibco/BRL), supplemented with 100 ug/ml ampicillin (International Biotechnologies Inc., New Haven, Conn.) and incubated for 12–18 hours at 37° C. A suitable colony, was then selected for placement in Terrific Broth (Gibco/BRL), which has been supplemented with 100 ug/ml ampicillin (International Biotechnologies Inc.)

Several colonies from the LB agar plates were selected and expanded. The plasmid DNA is purified using Promega's Wizard miniprep purification kit. Once plasmid DNA is purified, colonies are screened by sequence analysis in order to confirm that a particular clone selected contains the amino acid modification or alteration.

EXAMPLE X

Preparation and Radiolabeling of a Modified Annexin

The modified annexin, wherein accessible sulfhydryl groups are added to the N-terminus of the annexin molecule, can be prepared in accordance with the procedures set forth in Tanaka, et al., *Biochem.*, 35: 922–929, 1996, as follows.

Preparation of N-Terminally Extended Annexin V (Annexin V-N-6, also referred to as modified annexin). First, a mutant annexin VcDNA (pANXVC-S) was designed in which the $Cys_{316}$ codon was replaced by a Ser codon, an NdeI site was introduced prior to the initiator Met codon, and a BamHI site was introduced after the stop codon. This was constructed by PCR using an annexin V cDNA (pPAP-I-1.6; Funakoshi et al., 1987 Biochemistry 26:5572–5578, Cookson et al., 1994 Genomics 20:463–467) as a template and two oligonucleotides, 5'-g.gaa.ttc.cat.atg.gca.cag.gtt.ctc.aga.ggc.act.gtg-3' (SEQ ID NO:6) and 5'-cgc.gga.tcc.tta.gtc.atc.ttc.tcc.gga.gag.cag-3 (SEQ ID NO:7). This DNA was ligated into the NdeI and BamHI cloning sites in the pET12a plasmid (Novagen, Madison, Wis.). An oligonucleotide (5'-t.atg.gca.tgt.gac.cat.tc-3') (SEQ ID NO:8) and its inverse complement (5'-t.aga.atg.gtc.aca.tgc.ca-3') (SEQ ID NO:9) were prepared to encode six amino acid residues (Met-Ala-Cys-Asp-His-Ser) (SEQ ID NO:10) with NdeI-compatible overhangs at both ends. The two complementary oligonucleotides were annealed and the product was ligated into pANXVC-S that was digested with NdeI to produce plasmid pANXVC-S-N6. DNA sequencing of this plasmid confirmed that the intended mutations had been correctly introduced.

This plasmid (pANXVC-S-N6) was then transformed into *Escherichia coli* strain K-38 containing the pGP-1 plasmid for production of recombinant protein by expression from the T7 promotor of the vector. The cells were grown at 30° C. in 3 L of 2% L-broth in 50 mM potassium phosphate, pH 7.4, 25 μM kanamycin. After 4 h ($OD_{600}$=0.4), cells were given a heat shock by placing culture flasks in a 42° C. water bath for 20 min and the cultivation was continued at 37° C. for 2 h. Cells were then harvested and stored frozen overnight at −20° C.

Thawed cells were suspended in 100 mL of 50 mM Tris-HCl, pH 8.0, 10 mM $CaCl_2$, 0.1 mM DFP containing 1 mg of leupeptin and 1 mg of pepstatin and sonicated for 5 min. The cell lysate was treated with 5 μL of DNase (10 units/mL) for 10 min at room temperature. Then, pellets were collected by centrifugation, and annexin V-N6 was extracted from the pellets by stirring for 1 h at 4° C. in 70 mL of 50 mM Tris-HCl, pH 8.0, 8M urea, 0.1M $NH_4Cl$, 10 mM EDTA, 0.1 mM DFP containing 1 mg of leupeptin and 1 mg of pepstatin. The supernatant obtained by centrifugation was diluted 2-fold with 50 mM Tris HCl, pH 8.0 and 0.1 mM DTT and left for 48 h at 4° C. The sample was then dialyzed successively against 150 mL, 500 mL, and 2 L of 0.1M sodium-phosphate, pH 6.0. The dialyzed sample was applied to a DEAE-Sepharose column (1.4×18 cm) that was equilibrated with 0.1M phosphate, pH 6.0. After the column was washed, proteins were eluted by a linear gradient formed by 100 mL each of 0M and 0.5M NaCl in the phosphate buffer. The major protein peak that contained anticoagulant activity was pooled and ammonium sulfate was added to 80% saturation. The precipitates collected by centrifugation were dissolved in 5 mL of 50 mM sodium-acetate, pH 5.6, 150 mM NaCl, and 10 mM DTT and applied to a Sephadex G-75 column (2.5×90 cm) equilibrated with the same buffer except for DTT. Annexin V-N6 eluted as a single peak and it was homogeneous on SDS-PAGE with a molecular mass of 36 kDa. The yield was 35 mg of protein from 3 L of culture medium. The modified annexin prepared as described above is then used according to the invention.

EXAMPLE XI

Preparation of a Modified Annexin V and its Dimer

Modified annexin V, by addition of accessible sulfhydryl groups, and its dimer, is produced as follows:

Transfect the existing plasmid pJ110 (also known as pANXVC-S-N6) into *E. coli* strain BL21(DE3). Express cytoplasmically by overnight growth to saturation in 4×1 L of T broth. Harvest the cells by centrifugation. Sonicate in a buffer consisting of 50 mM TrisHCl pH 7.2, 10 mM $CaCl_2$. Centrifuge (20 min at 23,000×g), discard supernatant. Release modified annexin from the pellet by suspending in 50 mM TrisHCl pH 7.2, 20 mM EDTA. Centrifuge (20 min, 23,000×g), discard the pellet. Treat the supernatant with RNase A (3 μg/ml) for 2 h at room temperature. Dialyze in 25,000 molecular weight cutoff tubing against 3×2 L of 20 mM TrisHCl pH 8.0 (well aerated); a portion of the modified annexin present is converted to A5 dimer by spontaneous disulfide bond formation due to air oxidation. Purify by ion-exchange FPLC on Pharmacia MonoQ HR10/10 column with a linear gradient from 0–0.5M NaCl in 20 mM TrisHCl pH 8.0. Add ⅟30 volume of 1M (2-[N-morpholino] ethanesulfonic acid; Sigma Chemical) to fractions to maintain pH at 5.8 and inhibit spontaneous disulfide bond formation. The monomer elutes at 0.22M NaCl and the dimer at 0.28M NaCl. This procedure yields approximately 5 mg each of pure monomer and dimer per L of starting culture material.

Once the disulfide link dimer of modified Annexin V is produced, it can be evaluated for membrane and thrombus binding activity as well as pharmacokinetics and organ uptake in mice. Its affinity for cell membranes is determined by direct titration (1, below), its blood disappearance curve and biodistribution are determined in mice (2, below), and its thrombus:blood ratio determined in vivo in the porcine atrial thrombus model 30 min and 120 min after injection and compared with the corresponding ratio for monomeric annexin V (3, below).

1. Binding of modified Annexin V and Annexin V dimer to Phosphatidylserine containing membranes. If derivatives are not already labeled with Tc-99m, each derivative is labeled with I-125 by the Iodo-Gen method and purified by gel filtration, as previously described for annexin V (see Tait et al, *J. Lab. Clin. Med* 123: 741–8, 1994). The affinity of each derivative for cell membranes is measured by direct titration of preserved erythrocytes with exposed phosphatidylserine as previously described in Tait et al, *J. Lab. Clin. Med.* 123: 741–8, 1994. Bound and free ligand are separated by centrifugation of cells through a silicone-oil barrier. The dissociation constant is determined by fitting the data to a simple model of binding to homogeneous sites as described by Tait. Use of artificially treated erythrocytes with high levels of exposed PS is an experimental convenience that gives results equivalent to those obtained with activated platelets with exposed PS. Normal erythrocytes in vivo do not have extracellularly exposed PS (Tait et al, *J. Lab. Clin. Med.*, 123: 741–8, 1994).

2. Blood clearance, biodistribution, and excretion in mice. An intravenous bolus of 10 μg/kg (0.3 μg per 30-gram mouse) of each I-125-labeled or Tc-99m-labeled derivative (dimer; galactose-modified annexin; Tc-99m-modified annexin; Tc-99m-serylsuccinate-labeled annexin V) is injected. Blood specimens are prepared at 1, 2, 3, 5, 7, 10, 15, 20, 30, 45, 60, 90, and 120 min. The following organs are harvested from four mice each at 30, 60, and 120 min after injection: brain, heart, aorta, vena cava, lung, spleen, liver, stomach, intestines, kidney, bladder, skeletal muscle, bone, and blood. Results are expressed as % ID/g tissue and % ID/organ.

3. Thrombus/blood ratio in vivo in pigs. Established procedures are used as described for acute atrial thrombi (Stratton et al, *Circulation*, 92: 3113–21, 1995) for I-125-labeled dimer, galactose-modified annexin, and annexin V as control. Based on previous experience with native annexin V in this model, a twofold difference in thrombus/blood ratios between modified and native annexin V can be demonstrated at a P value of ≦0.05 in a two-tailed t-test with an n of about 5 animals.

Once a molecule with desirable properties is identified, the annexin V dimer can be produced directly as a fusion protein using an existing expression system as described in Tait et al., *J. Biol. Chem.* 270: 21594–21599, with the two annexin V moieties connected by a peptide linker. This dimeric molecule can also contain additional functional sites, such as an endogenous Tc-99m chelation site or a free sulfhydryl to allow attachment of galactose.

EXAMPLE XII

Endogenous Radiolabeling of Modified Annexin

A study of Tc-99m radiolabeling of modified annexin (Annexin V-N-6 of Example X) was carried out following the method of George et al, *Proc. Natl. Acad. Sci. USA*, 92:8358–62, 1995. The modified annexin, 160 μg, was combined with 2.5 mCi of Tc-99m pertechnetate, with methylene diphosphonate as the exchange ligand and stannous ion as reductant. The final concentration of the protein as available was 200 μg/ml. However, incubation at pH 10 for 30 min at 37° C. resulted in 52% radiochemical yield. This apparent yield was consistent with results obtained after purification by gel filtration, which showed recovery of 56% of the applied radioactivity in 89% radiochemical purity. Storage of the purified material indicated no change in radiochemical purity as measured by TLC and Zorbax HPLC chromatography after 18 h in PBS at room temperature. In contrast, native annexin V showed only 2% labeling under the same conditions. Thus, the results have shown that the modified annexin V molecule can be labeled directly with Tc-99m. One of ordinary skill in the art can evaluate the modified annexin V molecule for optimization of Tc-99m radiolabeling yield (protein concentration, exchange chelates, pH dependence, temperature, and time); radiolabel stability (challenge with serum and various concentrations of cysteine); cell and thrombus binding; blood clearance and biodistribution properties; catabolite forms of excreted radioactivity (HPLC of biological samples and comparison with synthetic peptide Tc-99m chelate standards for identification). Suitable methods include those used for characterization of various N,S amide thiolate chelating agent for Tc-99m bifunctional protein radiolabeling agents (Kasina et al, *J. Nucl. Med.*, 32: 1445–51, 1991; Fritzberg et al, *Proc. Natl. Acad. Sci. USA*, 95: 4025–9, 1988).

EXAMPLE XIII

Production of a Radiolabeled Annexin-Esterase Sensitive Chelate Conjugate $$TcO_4^- + SnCl_2 + \text{Gluconic Acid} \xrightarrow{pH\ 5.5-7.0} {}^VTc\text{-gluconate}$$

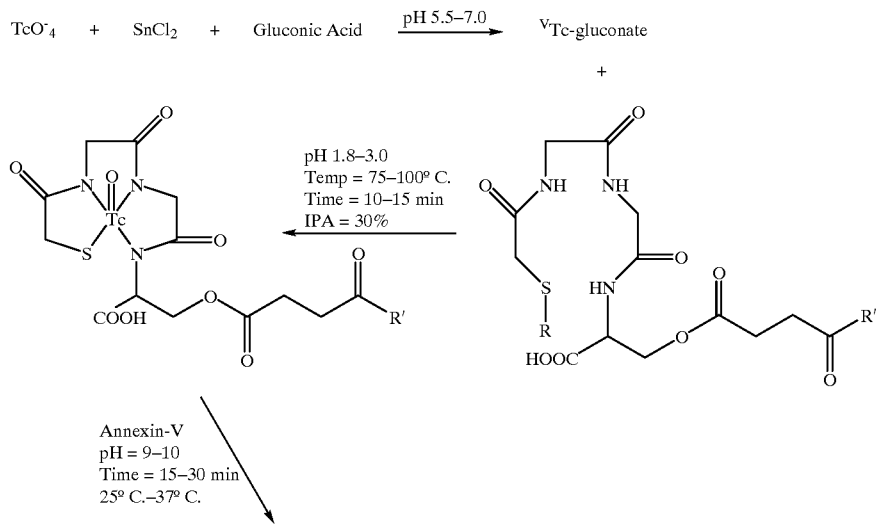

-continued

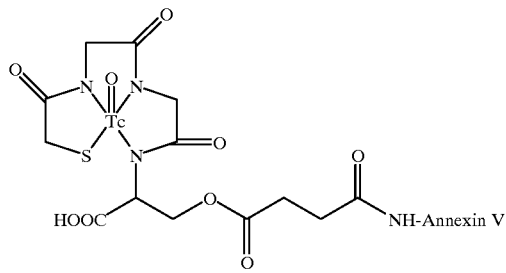

Experimental procedure—Annexin V is radiolabeled with Tc-99m N$_3$S-serylsuccinate via the preformed chelate approach as described for antibody Fab fragments (Srinivasan et al, *J. Nucl. Med.*, 32: 1017 (abstract), 1991). Application of this approach with the C$_5$N$_2$S$_2$ active ester has been similar for both antibody proteins (Kasina et al, *J. Nucl. Med.*, 32: 1445–51, 1991) and annexin V (Stratton et al, *Circulation*, 92: 3113–21, 1995). In the present procedure, serylsuccinate ester is substituted in the radiolabeling procedure. This derivative is evaluated in vitro for label stability, membrane binding, and clot binding. It can be injected into mice and its uptake measured in organs including liver and kidney over the period from 10 min to 2 h. This indicates the rate of organ uptake as well as retention, and allows comparison of the time course with previous data for the amide-linked Tc-99m chelate.

Success is indicated by significant reduction in liver retention of radioactivity. Increased rate of organ disappearance following uptake of Tc-99m annexin V indicates the potential of improved thrombus to organ ratios within time of imaging follow up. Imaging experiments can be performed with the porcine model in order to predict comparable improvements under clinical conditions.

Labeling of annexin V with Tc-99m-serylsuccinate ester. Annexin V conjugated to the serylsuccinate ester is labeled with Tc-99m according to the OncoTrac kit procedure (Kasina et al, *J. Nucl. Med.*, 32: 1445–51, 1991), and then conjugated to annexin V using the previously described method for conjugation of Tc-99m-N$_2$S$_2$-TFP to annexin V (Stratton et al, *Circulation*, 92: 3113–21, 1995).

EXAMPLE XIV

Production of a Radiolabeled Modified Annexin V-Galactose Cluster-Chelate Conjugates A maleimide-linked galactose cluster of the present invention can be conjugated specifically to the sulfhydryl of the modified annexin V. After verification of stoichiometry of galactose labeling, the galactose-modified annexin is radioiodinated and evaluated for membrane and thrombus binding in vitro, and pharmacokinetics and organ uptake in mice. Maintenance of binding and faster blood disappearance are followed up by determining in vivo thrombus to blood ratios in the porcine model at 30 and 120 min after injection and compared to corresponding ratios for unmodified annexin V.

The rate of blood disappearance of the modified Annexin V without compromising the ability of the modified annexin V to bind to cell membranes or thrombi in vitro is compared to unmodified annexin V. The in vivo thrombus/blood ratio 30 min after injection should be higher compared to native annexin V, and the same or higher at 120 min after injection. However, if use of this mechanism also increases the background signal from the liver at the particular times chosen for imaging, use of the esterase-sensitive linker mechanism to accelerate excretion of radiolabel from the liver can be used to decrease the background signal. The following examples represent further embodiments of the present invention.

EXAMPLE XV

Procedure for N-acetylgalactosamine-S-Annexin-N-Chelating Compound

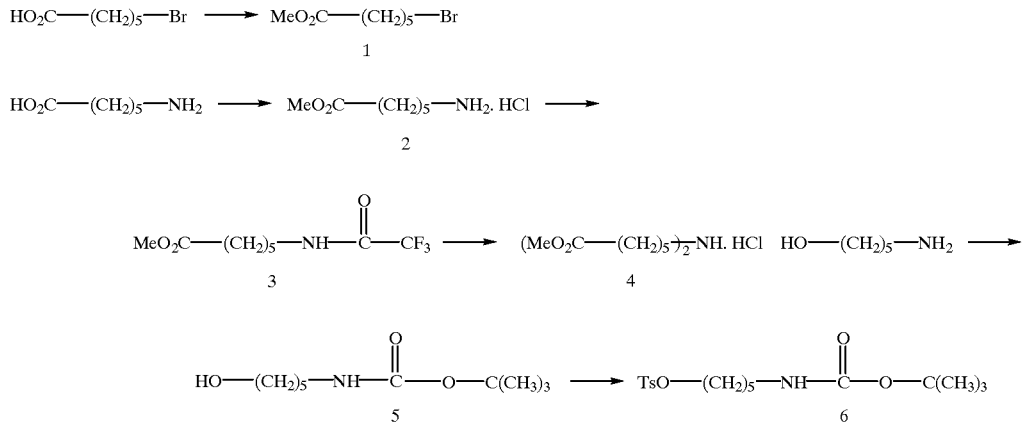

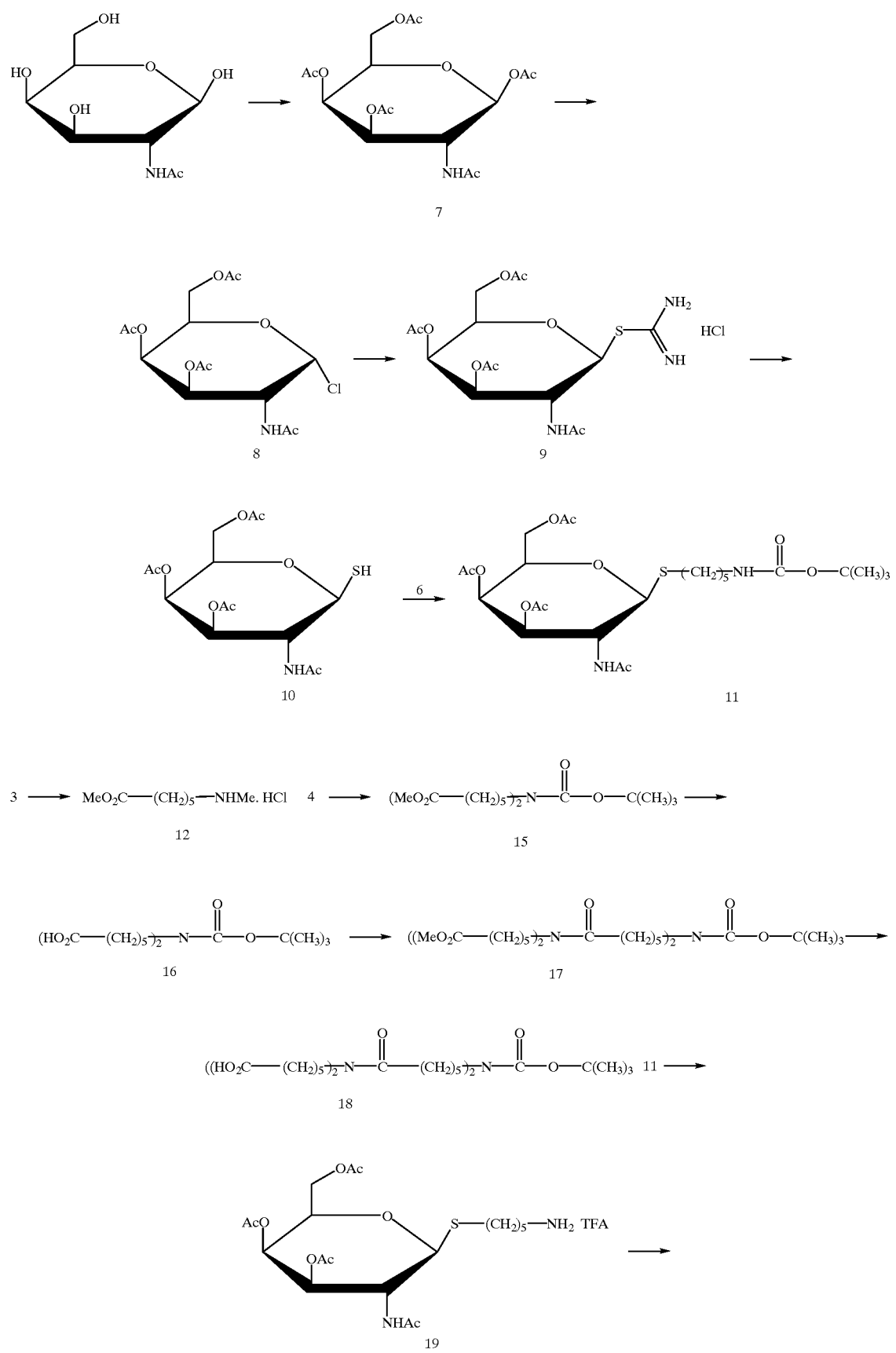

-continued
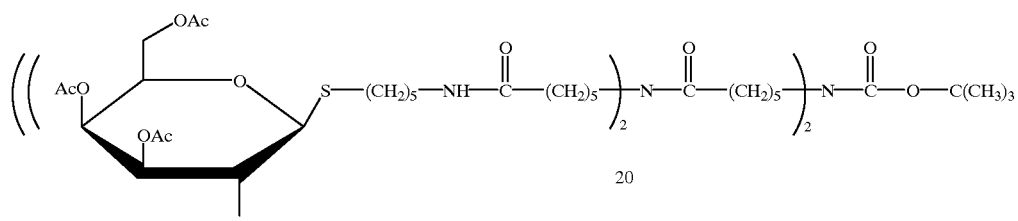
20
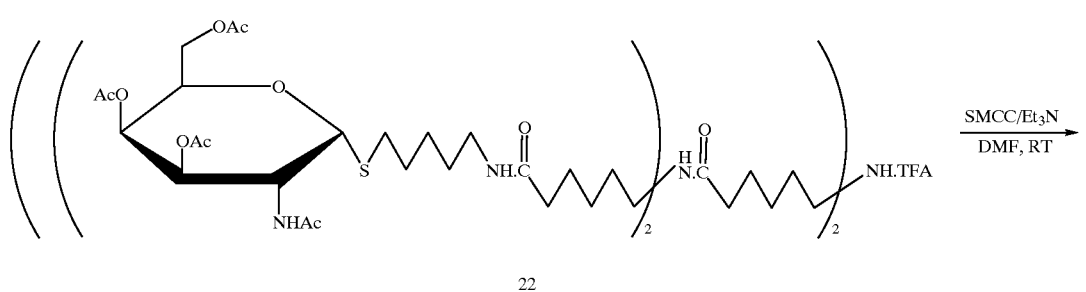
22
SMCC/Et₃N
―――――→
DMF, RT
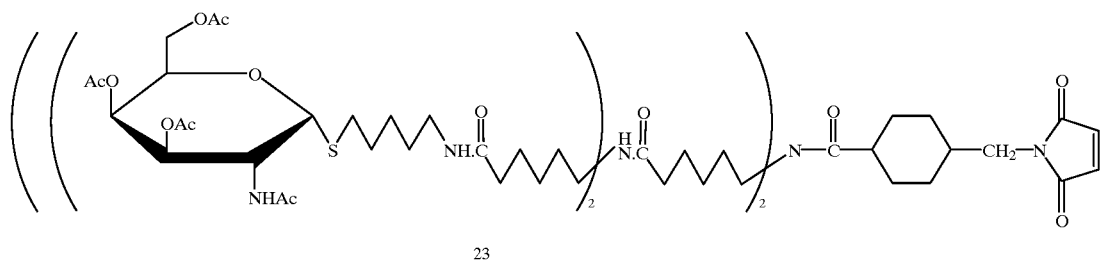
23
1) AG-1 x 8 Anion
exchange resin
MeOH/H₂O, Rt
17 hrs, filter,
concentrate
↓
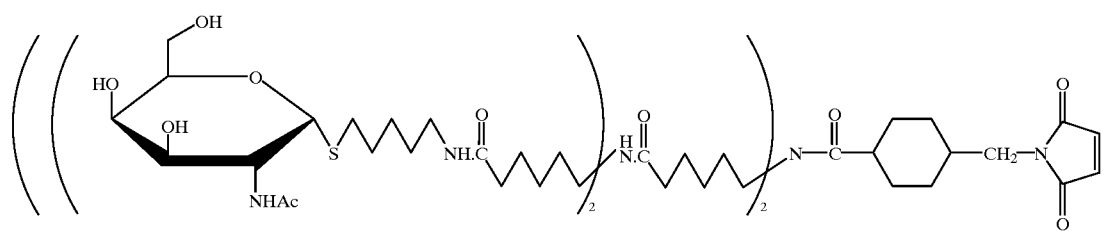
24
Modified Annexin V cys SH
pH 5-9, 25°C.-37°C.
↓

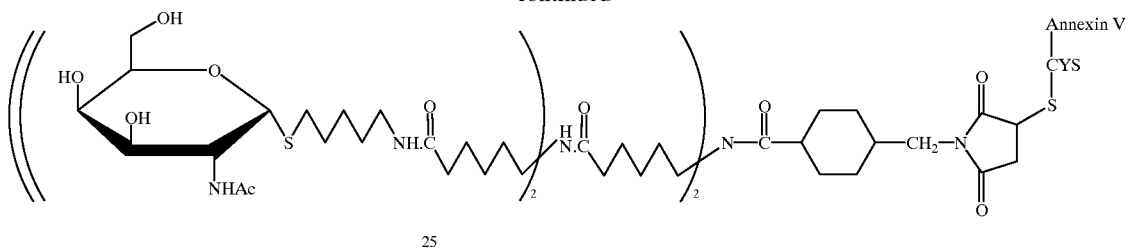

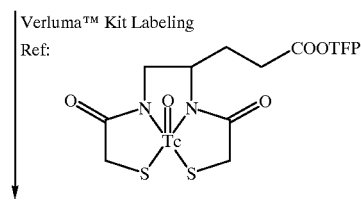

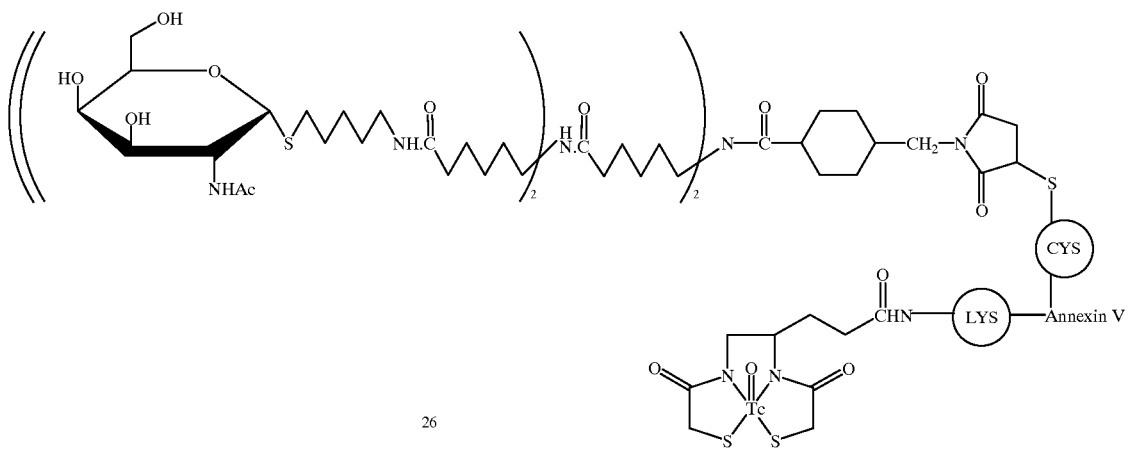

Preparation of Methyl 6-bromohexanoate (1)

To a 2 liter round bottom flask, charge with 99.7 g (0.511 mol) of 6-bromohexanoate (Aldrich Chemical Co., Milwaukee, Wis.) and 1 liter of methanol, was bubbled hydrogen chloride gas for 1–2 minutes. The mixture was stirred at 20–30° C. for 18 h and then concentrated via rotary evaporation. The residue was diluted with 500 mL of diethyl ether and washed with 150 mL of de-ionized water, 200 mL of saturated sodium bicarbonate, and then once again with 200 mL of de-ionized water. The organic phase was dried over anhydrous magnesium sulfate, filtered and concentrated via rotary evaporation. The residue was distilled under vacuum to afford 99.6 g of the product (1) as a colorless oil (93%): b.p.=93–96° C. at 3 mm Hg: $^1$H NMR ($d_6$-DMSO) d 3.57 (3H, s), 3.51 (2H, t), 2.30 (2H, t), 1.78 (2H, pentet) and 1.62–1.28 (4H, m) ppm.

Preparation of Methyl 6-Aminohexanoate Hydrochloride (2)

To a 2 liter round bottom flask, charged with 101.3 g (0.722 mol) of 6-aminohexanoate (Aldrich Chemical Co.) in 1 liter of methanol was bubbled hydrogen chloride gas for 3–4 minutes. The mixture was stirred at 20–30° C. for 16 h and then concentrated via rotary evaporation. The residue was twice diluted with 500 mL of methanol and re-concentrated (<0.5 mm Hg) to afford 140.1 g of the product (2) as a white solid (100w): $^1$H NMR ($d_6$-DMSO) d 9.40 (1H, broad triplet), 3.57 (3H, s), 3.15 (2H, quartet), 2.29 (2H, t), 1.60–1.38 (4H, m) and 1.32–1.19 (2H, m) ppm.

Preparation of Methyl 6-(Trifluoroacetamido)hexanoate (3)

To a 2 liter round bottom flask, charged with 100.2 g (0.552 mol) of amine hydrochloride 2 and 1 liter of methanol was added 100 g (0.703 mol) of ethyl trifluoroacetate followed by 120 mL (0.861 mol) of triethylamine. The mixture was stirred at 20–30° C. for 19 h and then concentrated via rotary evaporation. The residue was diluted with 500 mL of diethyl ether and then filtered. The filtrate was washed with 3×300 mL aliquots of iN aqueous HCl, 200 mL of de-ionized water, 2×200 mL aliquots of saturated aqueous sodium bicarbonate and finally with 200 mL of de-ionized water. The organic phase was dried over anhydrous magnesium sulfate, filtered and concentrated. The residue was distilled under vacuum to afford 115.8 g of the product (3) as a colorless oil: b.p.=113–116° C. at 120 mm Hg: $^1$H NMR ($d_6$-DMSO) d 3.57 (3H, s), 2.75 (2H, m), 2.29 (2H, t), 1.60–1.40 (4H, m) and 1.37–1.19 (2H, m) ppm.

Preparation of N,N-Bis-(5-Methoxycarbonylpentyl)amine Hydrochloride (4)

To a 5 liter three neck flask equipped with a reflux condenser connected to a gas bubbler, charged with 20.9 g of 60% sodium hydride (0.523 mol) in 1 liter of anhydrous dioxane, was added 100 g (0.416 mol) of secondary amide 3 in 200 mL of dry dioxane over a 20 minute period. The mixture was stirred at 20–30° C. for 1 h, and then 130 g (0.622 mol) of bromide 1 in 100 mL of dioxane was added. The mixture was heated to reflux and stirred for 7 h. An additional 10 g of 1 was added and the resulting mixture stirred for 15 h more. The mixture was cooled and concentrated via rotary evaporation. The residue was diluted with 600 mL of 1N aqueous HCl and extracted with 1 liter of ethyl acetate. The organic phase was then washed with 250 mL of de-ionized water, 250 mL of 5% aqueous sodium metabisulfite, and finally with 250 mL of de-ionized water. The organic phase was dried over anhydrous magnesium sulfate, filtered and concentrated.

The residue was diluted with 300 mL of de-ionized water and 500 mL of methanol and treated with 200 mL of 10N aqueous sodium hydroxide. The mixture was stirred at 20–30° C. for 16 h and concentrated to a thick syrup via rotary evaporation. The residue was diluted with 800 mL of deionized water and acidified to pH 1–2 with 200 mL of concentrated HCl. The mixture was washed with 3×300 mL aliquots of diethyl ether and the aqueous phase then concentrated to a thick syrup via rotary evaporation. The residue was diluted with 1 liter of dry methanol and re-concentrated via rotary evaporation. The residue was diluted with 1 liter of dry methanol and then hydrogen chloride gas was bubbled into the mixture for 2–3 minutes. The mixture was stirred at 20–30° C. for 18 h, and then vacuum filtered through Celite (manufactured by J. T. Baker). The solids were rinsed with 200 mL of methanol. The combined filtrates were concentrated. The residue was diluted with 1 liter of methanol and hydrogen chloride gas again bubbled into the mixture for 2–3 minutes. The mixture was stirred for 3 h and then concentrated. The residue was diluted with 1 liter of methanol and 10 g of activated charcoal was added. The mixture was stirred for 30 minutes and then vacuum filtered through Celite. The solids were washed with 100 mL of methanol and the combined filtrates concentrated. The residue was dissolved in hot 2-propanol and then allowed to recrystallize, first at room temperature and then with the use of an ice bath. The solids were filtered and rinsed with 3×75 mL aliquots of cold 2-propanol. The solids were air dried to afford 70.5 g of the product (4) as a white solid. The filtrates were combined and concentrated. The residue was recrystallized from 200 mL of 2-propanol to afford an additional 15.3 g of product for a total of 85.8 g (67%): $^1$H NMR ($d_6$-DMSO) d 8.69 (2H, broad), 3.57 (6H, s), 2.82 (4H, m), 2.30 (4H, t), 1.67–1.43 (8H, m) and 1.28–1.19 (4H, m) ppm; $^1$H NMR ($CD_3OD$) d 3.66 (6H, s), 3.42 (4H, t), 2.34 (4H, t), 1.75–1.55 (8H, m) and 1.45–1.25 (4H, m) ppm.

Preparation of N-BOC-5-Aminopentanol (5)

To a 2 liter three neck round bottom flask, fitted in the center neck with a 500 mL addition funnel and in a side neck with an adaptor venting to a gas bubbler, was added 40 g (0.388 mol) of 5 aminopentanol in 500 mL of dry acetonitrile. Then 84.5 g (0.387 mol) of di-t-butyl-dicarbonate in 400 mL of dry acetonitrile was added over a 50 minute period. The mixture was stirred at 20–30° C. for 15 h and then concentrated. The residue was diluted with 600 mL of ethyl acetate and washed with 2×200 mL aliquots of 0.5N aqueous HCL and 2×200 mL aliquots of de-ionized water. The organic phase was dried over anhydrous magnesium sulfate, vacuum filtered, and concentrated, first via rotary evaporation and then using full vacuum pump pressure (<0.5 mm Hg), to afford 74.5 g of the product (5) as a near colorless oil (88%): $^1$H NMR ($d_6$-DMSO) d 6.72 (1H, broad triplet), 4.31 (1H, t), 3.43–3.27 (2H, m), 2.87 (2H, quartet), and 1.45–1.10 (15H, s and multiplet) ppm; 1H NMR ($CDCl_3$) d 4.58 (1H, broad s), 3.65 (2H, t), 3.13 (2H, quartet), and 1.70–1.30 (15H, singlet and multiplet) ppm: Thin Layer Chromatography (Visualization with ninhydrin spray and heat); Silica Gel, $R_f$=0.28 (95/5 methylene chloride/methanol).

Preparation of N-BOC-5-Aminopentyltoluenesulfonate (6)

To a 1 liter round bottom flask, charged with 74.5 g (0.366 mol) of N-BOC-aminopentanol (6) in 400 mL of methylene chloride, was added 45 mL of anhydrous pyridine followed by 74.1 g (0.389 mol) of p-toluenesulfonyl chloride. The mixture was stirred at room temperature for 17 h, diluted with 200 mL of methylene chloride and washed with 400 mL of 0.5N HCl, 2×200 mL aliquots of 0.5N HCl, and 2×100 mL aliquots of de-ionized water. The organic phase was dried over anhydrous magnesium sulfate, vacuum filtered, and concentrated. The residue was chromatographed on 11×23 cm of silica gel, eluting first with methylene chloride and then with 3:97 ethyl acetate/methylene chloride. The fractions containing product were combined and concentrated, first via rotary evaporation and then under full vacuum pump pressure (<0.5 mm Hg), to afford 82.13 g of the product (6) as a white solid: $^1$H NMR ($CDCl_3$) d 7.77 (2H, d), 7.31 (2H, d), 4.45 (1H, broad s), 3.98 (2H, t), 3.03 (2H, t), 2.41 (3H, s), and 1.80–1.20 (15H, singlet and multiplet) ppm: Thin Layer Chromatography (Visualization with ninhydrin spray and heat); Silica Gel, $R_f$=0.50 (3:97 ethyl acetate/methylene chloride).

Preparation of 1-b, 3,4,6-Tetra-O-Acetyl-N-Acetyl-Galactosamine (7)

To a 500 mL round bottom flask charged with 25.0 g (116 mmol) of galactosamine hydrochloride (Sigma Chemical Co., St. Louis, Mo.) was added 180 mL of anhydrous pyridine and then 115 mL of acetic anhydride (1.22 mol). The mixture was stirred at 20–30° C. for 44 h and then poured into a 2 liter beaker containing 600 g of ice and 600 mL of de-ionized water. The mixture was stirred at room temperature for 10–15 minutes and then vacuum filtered. The collected solids were rinsed with 4×100 mL aliquots of de-ionized water, air dried for 2 h and then dried under full vacuum pump pressure (<0.5 mm Hg) for 14 h to give 39.8 g of the product as a white solid (88%) : $^1$H NMR ($d_6$-DMSO) d 7.89 (1H, d), 5.63 (1H, d), 5.16 (1H, d), 5.07 (1H, dd), 4.28–3.92 (4H, m), 2.11 (3H, s), 2.02 (3H, s), 1.99 (3H, s), 1.90 (3H, s) and 1.88 (3H, s) ppm.

Preparation of 3,4,6-Tri-O-Acetyl-N-Acetyl-Galactosamine-1-b-Pseudothiourea Hydrochloride (9)

To a 1 liter round bottom flask, charged with 39.8 g (102 mmol) of 7, was added 400 mL of acetyl chloride. The mixture was stirred at 47–48° C. for 64 h. The mixture was concentrated and then twice diluted with 200 mL of methylene chloride and re-concentrated, first via rotary evaporation and then under full vacuum pump pressure (<0.5 mm Hg), to afford 40.2 g of the crude product (8) as a dark amber foamy solid: $^1$H NMR ($CDCl_3$) d 6.24 (1H, d), 5.61 (1H, d), 5.43 (1H, dd), 5.27 (1H, dd), 4.83–4.71 (1H, m), 4.48 (1H, t), 4.22–4.01 (2H, 2 dd's), 2.15 (3H, s), 2.02 (3H, s), 2.00 (3H, s) and 1.98 (3H, s) ppm. To the crude chloride (8), in a 1 liter round bottom flask, was added 9.3 g (122 mmol) of thiourea and 150 mL of acetone. The mixture was stirred at reflux for 40 minutes and then cooled in an ice bath for 30 minutes and then vacuum filtered. The collected solids were rinsed with 2×75 mL aliquots of acetone. The solids were then air dried for 45 minutes and then dried further under full vacuum pump pressure (<0.5 mm Hg) for 2 h to afford 33.0 g of the product (9) as a light beige solid (74% overall yield from 7): $^1$H NMR ($d_6$-DMSO) d 9.38 and 9.12 (2 broad s's, 3H), 8.36 (1H, d), 5.56 (1H, d), 5.34 (1H, d), 5.01 (1H, dd), 4.38 (1H, t), 4.22–4.00 (3H, m), 2.11 (3H, s), 2.01 (3H, s), 1.92 (3H, s) and 1.81 (3H, s) ppm.

Preparation of 1-b-Mercapto 3,4,6-Tri-O-Acetyl-N-Acetyl-Galactosamine (10)

To a 1 liter round bottom flask, charged with 30.0 g (67.9 mmol) of the pseudothiourea (9) in 175 mL of methylene chloride and 175 mL of de-ionized water was added 7.08 g (37.24 mmol) of sodium metabisulfite followed by careful addition of 10.2 g (74.5 mmol) of potassium carbonate. The mixture was stirred at room temperature for 40 minutes and the mixture then transferred to a 500 mL separatory funnel. The layers were separated and the aqueous phase was then extracted with 2×125 mL aliquots of methylene chloride. The organic extracts were combined, dried over anhydrous sodium sulfate, filtered and concentrated to give 24.2 g (10) of the product as a very pale yellow (off-white) solid (98%): $^1$H NMR (CDCl$_3$) d 6.24 (1H, d), 5.61 (1H, d), 5.43 (1H, dd), 5.27 (1H, dd), 4.83–4.71 (1H, m), 4.48 (1H, t), 4.22–4.01 (2H, 2 dd's), 2.15 (3H, s), 2.02 (3H, s), 2.00 (3H, s) and 1.98 (3H, s) ppm.

Preparation of 3,4,6-Tri-O-Acetyl-N-Acetyl-Galactosamine-1-a-S-[5'-Thiopentyl-N-BOC-Amine] (11)

To a 1 liter round bottom flask, charged with 24.2 g (66.6 mmol) of the thiol (10) under nitrogen atmosphere, was added 350 mL of dry acetonitrile. The mixture was heated to 40–42° C., the solids eventually dissolving over a 20 minute period. 1,8-Diazabicyclo[5,4,0]undec-7-ene (DBU commercially available from Aldrich Chemical Company, 10.5 mL, 70.2 mmol) was then added and the mixture stirred for 20 minutes. Then, 24.0 g (67.1 mmol) of the tosylate 6 in 75 mL of acetonitrile was added over a 3–4 minute period. The resultant mixture was stirred at 40–25° C. for 1.5 h and then concentrated. The residue was diluted with 400 mL of methylene chloride and washed first with 250 mL of 0.5N aqueous HCl and then with 250 mL of 5% aqueous sodium bicarbonate. The organic phase was dried over anhydrous magnesium, vacuum filtered, and concentrated via rotary evaporation. The residue was chromatographed on 21×7 cm of silica gel (manufactured by E. M. Merck), eluting with 55/42.5/2.5 ethyl acetate/hexane/ethanol. The fractions containing product were combined, concentrated and re-chromatographed on 21×7 cm of RP-18 silica gel (manufactured by J. T. Baker), eluting with 500 mL each of 50/50, 55/45, 60/40, 65/35, and 70/30 methanol/water and then with 75/25 methanol/water until all of the desired product had eluted from the column. The fractions containing product were combined and concentrated. The residue was diluted with 500 mL of methylene chloride and treated with anhydrous magnesium sulfate. The mixture was vacuum filtered and the filtrate was concentrated, first via rotary evaporation and then under full vacuum pump pressure (<0.5 mm Hg) to afford 17.9 g of the product (11) as a foamy white solid: $^1$H NMR (d6-DMSO) d 9.38 and 9.12 (2 broad s's, 3H), 8.36 (1H, d), 5.56 (1H, d), 5.34 (1H, d), 5.01 (1H, dd), 4.38 (1H, t), 4.22–4.00 (3H, m), 2.11 (3H, s), 2.01 (3H, s), 1.92 (3H, s) and 1.81 (3H, s) ppm: Thin Layer Chromatography (Visualization with p-anisaldehyde spray and heat); Silica Gel, R$_f$=0.50 (57/40.5/2.5 ethyl acetate/hexane/ethanol); RP-18 Silica Gel, R$_f$=0.21 (65/35 methanol/water).

Preparation of Methyl 6-Methylaminohexanoate Hydrochloride (12)

To a 2 liter three neck round bottom flask, charged with 8.77 g of 60% NaH in mineral oil (219 mmol, 1.1 equiv.) in 500 mL of anhydrous tetrahydrofuran, was fitted a 500 mL addition funnel in the center neck. Then, 34.5 g (144 mmol) of secondary amide 3 in 300 mL of anhydrous tetrahydrofuran was added over a 30 minute period. The mixture was stirred for 50 additional minutes and then 22.6 mL (363 mmol) of iodomethane was added. The mixture was stirred at room temperature for 23 h and then transferred to a 2 liter round bottom flask and concentrated via rotary evaporation. The residue was treated with 400 mL of 1N aqueous HCl and then extracted with 300 mL of ethyl acetate and then with 2×200 mL aliquots of ethyl acetate. The organic extracts were combined and first washed with 3×125 mL aliquots of 5% aqueous sodium thiosulfate and then with 100 mL of de-ionized water. The organic phase was dried over anhydrous magnesium sulfate, vacuum filtered, and concentrated. The residue was dissolved in 250 mL of methanol and re-concentrated. The residue was diluted with 250 mL of methanol and treated with 50 mL of 10N aqueous sodium hydroxide followed by 100 mL of de-ionized water. The mixture was stirred at room temperature for 17 h, diluted with an additional 50 mL of de-ionized water and then washed with 3×200 mL aliquots of hexane. The aqueous phase was concentrated via rotary evaporation. The residue was diluted with 500 mL of methanol and hydrogen chloride gas was bubbled into the mixture for 2–3 minutes (10 g). The mixture was stirred at room temperature for 3 h and then vacuum filtered and concentrated via rotary evaporation. To the residue was added 500 mL of methanol and then hydrogen chloride gas was again bubbled into the mixture for 2–3 minutes (9.2 g). The mixture was stirred at room temperature for 18 h. The mixture was cooled in an ice bath and then vacuum filtered. The filtrate was concentrated by rotary evaporation. The residue was twice diluted with 250 mL of methanol and re-concentrated. The residue was diluted with 300 mL of 2-propanol and treated with 4 g of activated charcoal for 30 minutes. The mixture was vacuum filtered through Celite and the solids rinsed with 2×75 mL aliquots of 2-propanol. The filtrates were combined and concentrated, first via rotary evaporation and then under full vacuum pump pressure. The residue was diluted with 250 mL of methanol and re-concentrated, first via rotary evaporation and then under full vacuum pump pressure. The residue was diluted with 250 mL of methanol and hydrogen chloride gas was bubbled into the mixture for 1–2 minutes (5.0 g). The mixture was stirred at room temperature for 2 h and then concentrated via rotary evaporation. The residue was twice diluted with 250 mL of methanol and concentrated, first via rotary evaporation and finally under full vacuum pump pressure (<0.5 mm Hg) to afford 23.91 g of the product (12) as a very light yellow foamy solid (85%): $^1$H NMR (d$_6$-DMSO) d 8.72 (2H, broad s), 3.58 (3H, s), 2.82 (2H, m), 2.49 (3H, s), 2.32 (2H, t), 1.68–1.45 (4H, m) and 1.39–1.21 (2H, m) ppm; $^1$H NMR (CD$_3$OD) d 3.63 (3H, s), 2.97 (2H, t), 2.34 (2H, t), 1.75–1.56 (4H, m) and 1.49–1.31 (2H, m) ppm.

Preparation of N-BOC-N,N-Bis-(5-Methoxycarbonylpentyl)amine (15)

To a 500 mL round bottom flask, charged with 6.34 g (29.1 mmol) of di-t-butyl-dicarbonate and 9.00 g (29.1 mmol) of N,N-bis-(5-methoxycarbonylpentyl)-amine hydrochloride (4), was added 125 mL of anhydrous acetonitrile followed by 7.5 mL of triethylamine. The mixture was stirred at room temperature for 22 h and then concentrated via rotary evaporation. The residue was diluted with 300 mL of ethyl acetate and washed with 2×100 mL aliquots of 0.1N aqueous HCl, 100 mL of de-ionized water and 100 mL of 5% aqueous sodium bicarbonate. The organic phase was dried over magnesium sulfate, vacuum filtered and concentrated, first via rotary evaporation and then under full vacuum pump pressure (<0.5 mm Hg) to afford 10.5 g of product (15) as a near colorless oil (97%): $^1$H-NMR (d6-DMSO) d 3.57 (6H, s), 3.07 (4H, t), 2.28 (4H, t), 1.60–1.10 and 1.37 (21H, m and s) ppm; Thin Layer Chromatography (Visualization with ninhydrin spray and heat); Silica Gel, R$_f$=0.33 (20/80 ethyl acetate/hexane); RP-18 Silica Gel, R$_f$=0.17 (70/30 methanol/water).

Preparation of N-BOC-N,N-Bis-(5-Hydroxycarbonylpentyl)amine (16)

To a 500 mL round bottom flask, charged with 10.5 g of bis-methyl ester 15, was added 75 mL of methanol followed by 75 mL of 1N aqueous sodium hydroxide. The mixture was stirred at room temperature for 16 h and then concentrated via rotary evaporation. The residue was diluted with 75 mL of de-ionized water and the pH of the resultant solution adjusted to 2.0–2.5 by slow addition of approximately 75 mL of 1N aqueous HCl. Then, 200 mL of ethyl acetate was added and the mixture stirred vigorously for 3 minutes. The mixture was transferred to a separatory funnel and the layers separated. The aqueous phase was extracted with 2×150 mL aliquots of ethyl acetate. The organic extracts were combined, dried over anhydrous magnesium sulfate, and vacuum filtered. The filtrates were concentrated, first via rotary evaporation and then under full vacuum pump pressure (<0.5 mm Hg), to afford 9.52 g of the product as a viscous, nearly colorless oil (98%): $^1$H NMR (d$_6$-DMSO) d 3.07 (4H, t), 2.28 (4H, t), 1.58–1.10 and 1.37 (21H, m and s) ppm; Thin Layer Chromatography (Visualization with ninhydrin spray and heat); RP-18 Silica Gel, R$_f$=0.44 (70/30 methanol/water).

Preparation of N-BOC-N,N-Bis-(N',N'-Bis(5-Methoxycarbonylpentyl)-5-Carbamyl pentyl)Amine (17)

To a 1 liter round bottom flask, charged with 9.52 g (27.6 mmol) of bis-acid 16 in 250 mL of anhydrous dimethylformamide, was added 19.0 g (61.3 mmol) of N,N-bis-(5-methoxycarbonylpentyl)amine hydrochloride (4) followed by 30 mL of triethylamine. While the mixture was stirred, 25.7 g (58.1 mmol) of BOP was added. The resulting mixture was stirred at room temperature for 14 h and then concentrated via rotary evaporation. The residue was diluted with 750 mL of ethyl acetate and washed with 250 mL of 0.2N aqueous HCl, 100 mL of 0.1N aqueous HCl, 100 mL of de-ionized water, and 2×100 mL aliquots of 5 aqueous sodium bicarbonate. The organic phase was dried over anhydrous magnesium sulfate, vacuum filtered, and concentrated via rotary evaporation. The residue was chromatographed on 9×21 cm of silica gel, eluting first with 70% ethyl acetate/hexane and then with 100% ethyl acetate. The fractions containing product (17) were combined and concentrated via rotary evaporation. The residue was chromatographed on 7×23 cm of RP-18 silica gel, eluting first with 75:25 methanol/water, then with 80:20 methanol/water, and finally with 85:15 methanol/water. The fractions containing product were combined and concentrated, first via rotary evaporation and then under full vacuum pump pressure. The residue was diluted with 500 mL of diethyl ether and the resulting solution was dried with anhydrous magnesium sulfate. The mixture was vacuum filtered and the filtrate was concentrated, first via rotary evaporation and then under full vacuum pump pressure (<0.5 mm Hg), to afford 17.80 g of product (17) as a near colorless, viscous, oil (75%): $^1$H NMR (d$_6$-DMSO) d 3.57 (12H, s), 3.18 and 3.07 (12H, 2 t's), 2.32–2.16 (12H, m), 1.61–1.09 and 1.37 (45H, m and s) ppm; Thin Layer Chromatography (Visualization with ninhydrin spray and heat); Silica Gel, R$_f$=0.50 (ethyl acetate); RP-18 Silica Gel, R$_f$=0.30 (85/15 methanol/water).

Preparation of N-BOC-N,N-Bis-(N',N'-Bis(5-Hydroxycarbonylpentyl)-5-Carbamyl pentyl)Amine (18)

To a 500 mL round bottom flask, charged with 7.88 g (9.20 mmol) of the tetramethyl ester (18) in 75 mL of methanol, was added 70 mL of 1N aqueous sodium hydroxide. The mixture was stirred at room temperature for 16 h and then concentrated via rotary evaporation to a thick syrup. The residue was diluted with 50 mL of de-ionized water and, with vigorous stirring, the pH of the solution was adjusted to 2–2.5 by slow addition of approximately 70 mL of 1N aqueous HCl, the product (18) oiling out (one liquid phase separates from another liquid phase) in the process. The mixture was extracted with 200 mL of 3:1 2-propanol/methylene chloride, and then 3×100 mL aliquots of 3:1 2-propanol/methylene chloride. The organic extracts were combined, dried over anhydrous magnesium sulfate, filtered and concentrated, first via rotary evaporation and then under full vacuum pump pressure (<0.5 mm Hg) to afford 7.70 g of a near colorless, thick syrup, consisting (by NMR integration) of 6.93 g of the desired product (18; 94%) and 0.77 g of 2-propanol: $^1$H NMR (d$_6$-DMSO) d 3.18 and 3.07 (12H, 2 t's), 2.37–2.12 (12H, m), 1.60–1.10 and 1.37 (45H, m and s) ppm; Thin Layer Chromatography (Visualization with ninhydrin spray and heat); RP-18 Silica Gel, R$_f$=0.50 (70/30 methanol/water).

Preparation of N-BOC-Tet-Gal-NAc-1-a-S-C5 Branch (20)

To a 250 mL round bottom flask, charged with 4.05 g (7.38 mmol) of 3,4,6-tri-O-acetyl-N-acetyl-galactosamine-1-a-S-[5'-thiopentyl-N-BOC-amine] (11), was added 20 mL of methylene chloride followed by 20 mL of trifluoroacetic acid. The mixture was stirred at room temperature for 15 minutes. The mixture was concentrated via rotary evaporation and the residue was thrice diluted with 75 mL of methylene chloride and re-concentrated to afford 6.27 g of residue, a mixture of desired product (19) and residual trifluoroacetic acid: $^1$H NMR (CD$_3$OD) d 5.61 (1H, d), 5.41 (1H, dd), 5.01 (1H, dd), 4.62–4.47 (2H, m), 4.11 (2H, d), 2.91 (2H, t), 2.74–2.48 (2H, m), 2.11 (3H, 2s), 2.00 (3H, s), 1.93 and 1.91 (6H, 2s), and 1.37–1.10 (6H, m) ppm. To a separate 250 mL round bottom flask, charged with 1.33 g of the syrup containing 90%. 18 by weight (net 1.20 g, 1.50 mmol), was added 50 mL of anhydrous dimethylformamide. In order to remove residual 2-propanol, the mixture was concentrated, first via rotary evaporation and then under full vacuum pump pressure (<0.5 mm Hg). To the residue was added 20 mL of anhydrous dimethylformamide and 10 mL of dry triethylamine. To the resultant, stirred, solution was added a dimethylformamide solution of the crude 19 (in a total of 30 mL of anhydrous dimethylformamide) and the resultant mixture stirred at room temperature for 2 h. The mixture was then concentrated via rotary evaporation. The residue was then diluted with 250 mL of methylene chloride and washed with 2×100 mL aliquots of 1N aqueous HCl, 100 mL of de-ionized water, and then with 100 mL of saturated aqueous sodium bicarbonate. The organic phase was dried over anhydrous magnesium sulfate, vacuum filtered, and concentrated via rotary evaporation. The residue was chromatographed on 5.5×19 cm of RP-18 silica gel, eluting with 250 mL each of 65:35 methanol/water, 70:30 methanol/water, 75:25 methanol/water, and then with 800 mL of 80:20 methanol/water. The fractions containing product were combined, and concentrated, first via rotary evaporation and then under full vacuum pump pressure to afford 3.55 g of a foamy white solid (94%). This material was then chromatographed on 5.5×20 cm of silica gel, eluting with 80:20 ethyl acetate/methanol. The fractions containing only the desired product (20) were combined and concentrated, first via rotary evaporation and then under full vacuum pump pressure (<0.5 mm Hg), to afford 2.83 g of the desired product as a pure white foamy solid (75%): 1H NMR (CD$_3$OD) d 5.58 (4H, d), 5.42 (4H, dd), 5.01 (4H, dd), 4.63–4.51 (8H, m), 4.20–4.00 (8H, m), 3.35–3.10 (20H, m), 2.73–2.47 (8H, m), 2.32 (4H, t), 2.25–2.08 (20H, m and s), 2.00 (12H, s), 1.93 and 1.91 (24H, 2s), 1.71–1.20 (69H, m and s) ppm; Thin Layer Chromatography (Visualization with ninhydrin spray and heat); Silica Gel, R$_f$=0.47 (75:25 ethyl acetate/methanol); RP-18 Silica Gel, R$_f$=0.33 (80/20 methanol/water).

Preparation of N,N-Bis-(N',N'-Bis(5-Methoxycarbonylpentyl)-5-carbamyl pentyl)-Amine TFA (21)

To a 250 mL round bottom flask, charged with 1.50 g (1.75 mmol) of N-BOC-N,N-bis-(N',N'-bis(5-methoxycarbonylpentyl)-S-carbamyl pentyl)-amine (17) in 15 mL of methylene chloride, was added 15 mL of trifluoroacetic acid. The mixture was stirred at room temperature for 15 minutes and then concentrated. The residue was diluted with 50 mL of methylene chloride and then concentrated via rotary evaporation. The residue was then diluted with 50 mL of methanol and re-concentrated via rotary evaporation. The residue was again re-diluted with 50 mL of methylene chloride and re-concentrated, first via rotary evaporation and then under full vacuum pump pressure (<0.5 mm Hg).

Preparation of TFA Salt of Tet-Gal-NAc-1-a-S-Pentyl-amine Branch (22)

To a 100 mL round bottom flask, charged with 790 mg (0.313 mmol) of the N-BOC-Tet-Gal-NAc-1-a-S-C5 Branch (20), was added 10 mL of methylene chloride followed by 10 mL of trifluoroacetic acid. The mixture was stirred at room temperature for 15 minutes and then concentrated via rotary evaporation. The residue was diluted with 150 mL of methylene chloride and washed with 2×100 mL aliquots of saturated aqueous sodium bicarbonate. The organic phase was dried over magnesium sulfate, vacuum filtered and then concentrated, first via rotary evaporation and then under full pump pressure (<0.5 mm Hg), to afford 690 mg of the product (22) as a foamy off-white solid (91%).

Preparation of Tet-Gal-NAC-1-a-S-Pentyl Amine conjugate of modified Annexin V via SMCC derivatization (25)

The tetragalactosyl N-AC 1-a-S-Pentylamine (22) is reacted with SMCC reagent in triethylamine and DMF at room temperature. The maleimidyl derivative 23 is triturated with anion exchange resin of the type AG-1 X8 (BioRad; Hydroxide from; 2.6 m equiv./g) in aqueous methanol. The mixture is stirred at room temperature for 15 hours and then vacuum filtered. The resin is rinsed with 50 ml of deionized water and then with 50 ml of methanol. The filtrates are combined and concentrated via rotary evaporation and then under full vacuum pump pressure (<0.5 mm Hg) to afford the product 24 as a dry solid. Conjugation of modified Annexin V-SH with maleimidyl derivatized clustered galactose is carried out in 5–15% DMSO solvent at PH range of 5–8 in borate buffer. The maleimidyl galactose cluster is offered to the modified Annexin V at a molar ratios of 1:1, 5:1 and 10:1. The monomeric clustered galactose-Annexin V construct is then purified by gel filtration techniques. The product is then assayed for sulfhydryl content to determine the degree of derivatization to afford the conjugate 25 in good yield.

Preparation of $^{99m}$Tc-galactose cluster-Annexin V conjugate, 26

The $^{99m}$Tc-N$_2$S$_2$-TFP ester is prepared by the Verluma™ kit labeling procedure (Kasina, S., Rao, T. N., Srinivasan, A., et. al. Development and Biologic Evaluation of a Kit for Performed Chelate Technetium-99m Radiolabeling of an Antibody Fab Fragment Using a Diamide Dimercaptide Chelating Agent, *J Nucl Med,* 32: 1445–1451, 1991). The $^{99m}$Tc was incorporated into the N$_2$S$_2$-ligand via transchelation from $^{99m}$Tc-gluconate by heating. The $^{99m}$Tc-N$_2$S$_2$-TFP ester is then conjugated with galactose cluster-Annexin V construct in 0.2M bicarbonate buffer, PH 10.0 for 20–30 minutes at room temperature. The $^{99m}$Tc-N$_2$S$_2$-galactose cluster-Annexin V conjugate is purified by gel filtration chromatography to afford 30–40% radiochemical yield with a radiochemical purity of ≧85% product 26.

EXAMPLE XVI

Procedure for Annexin-S-Galactose-Chelating Compound

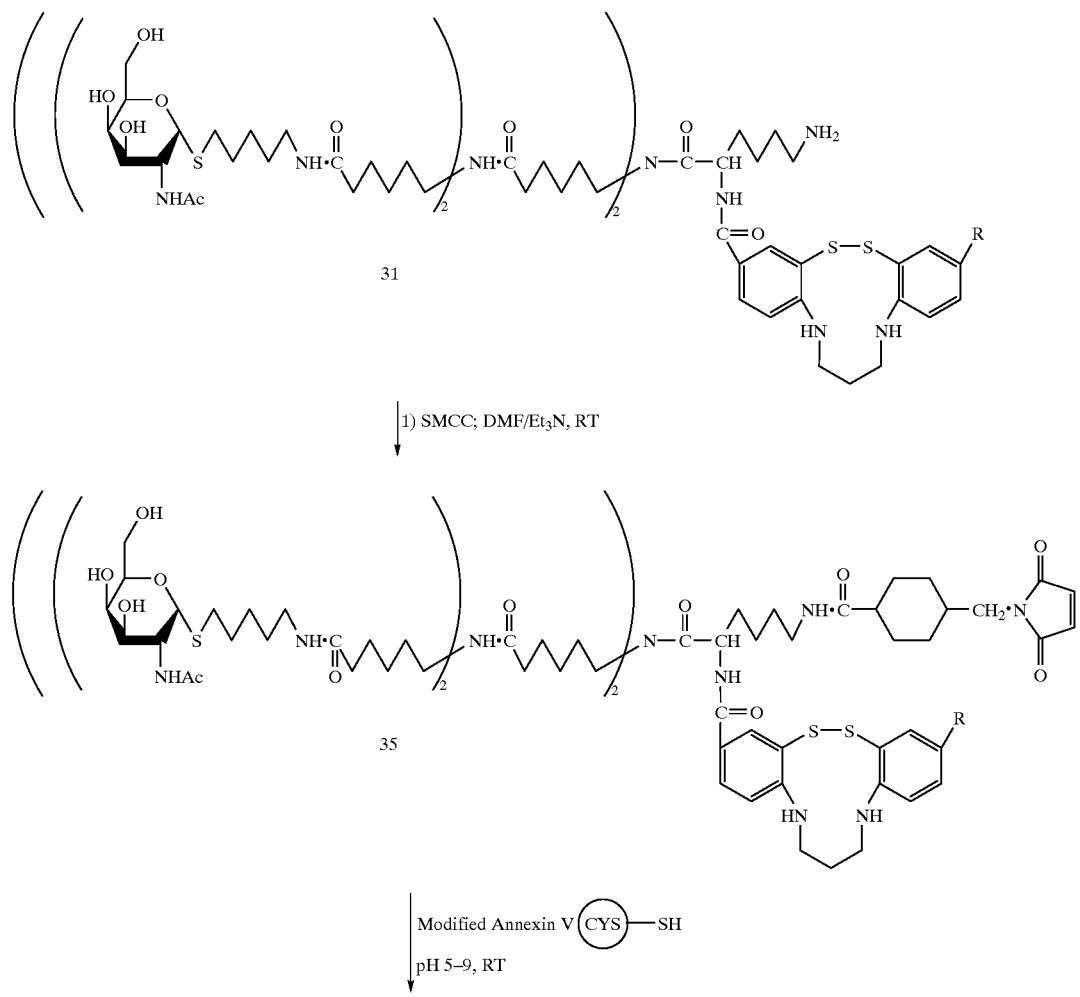

-continued

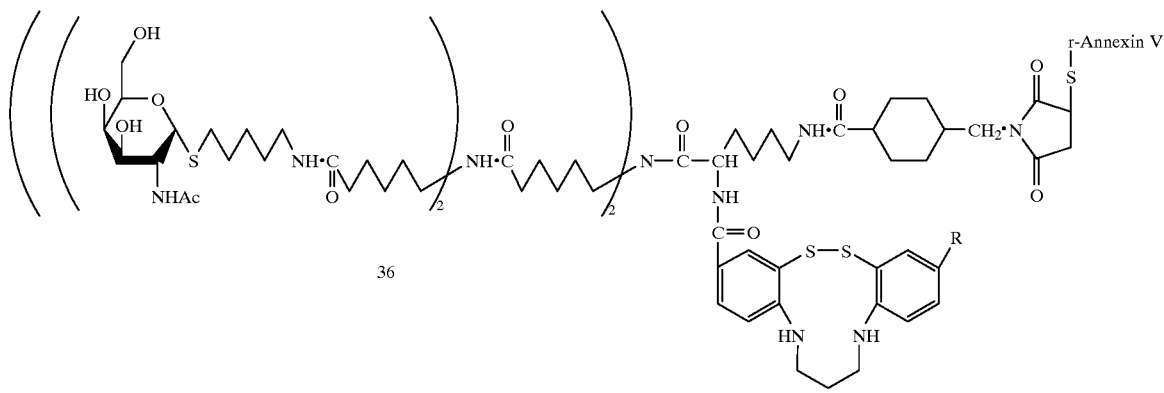

36

Preparation of modified Annexin V monomer conjugate of trifunctional lysine adduct containing galactose cluster-chelating compound moiety, 36

The epsilon amino BOC protection of the trifunctional lysine adduct of galactose cluster with the chelating compound 31 is reacted with trifluoroacetic acid in methylene choride. The reaction mixture is stirred at room temperature. The solvent removed under reduced pressure and dried to yield BOC deprotected epsilon amine in good yield. The crude product without further purification is triturated with AG-1 X8 anion exchange resin in aqueous methanol for 20 hours at room temperature. The mixture is filtered, and the resin is rinsed with methanol. The filtrates are combined and is concentrated to afford the o-deacetylated N-acetylgalactose cluster-chelating compound ligand of the trifunctional lysine as an epsilon amine in good yield. The epsilon amine functionality is reacted with 1.2 equivalents of SMCC reagent in DMF solvent in the presence of 10 equivalents of triethylamine at room temperature. The solvent is removed from the reaction mixture and the crude product is purified on a Silica gel column chromatography to afford the maleimidyl derivatized trifunctional galactose cluster chelating compound-ligand. SMCC adduct of the trifunctional lysine product 36 in good yield.

EXAMPLE XVII

Procedure for Annexin-S-Galactose-(Peptide)-Chelating Compound

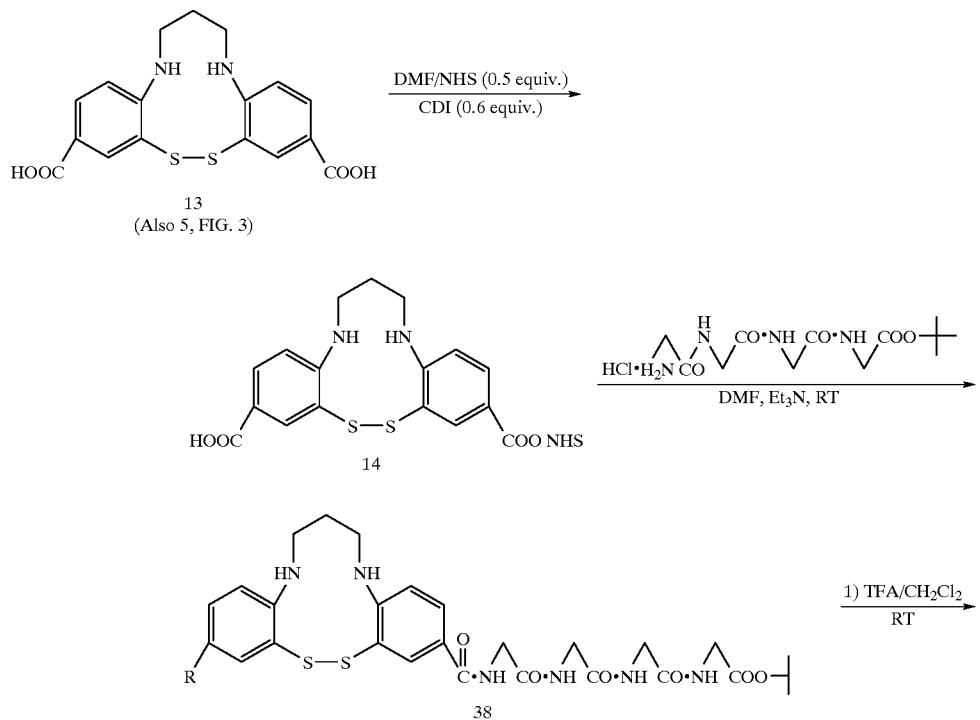

-continued
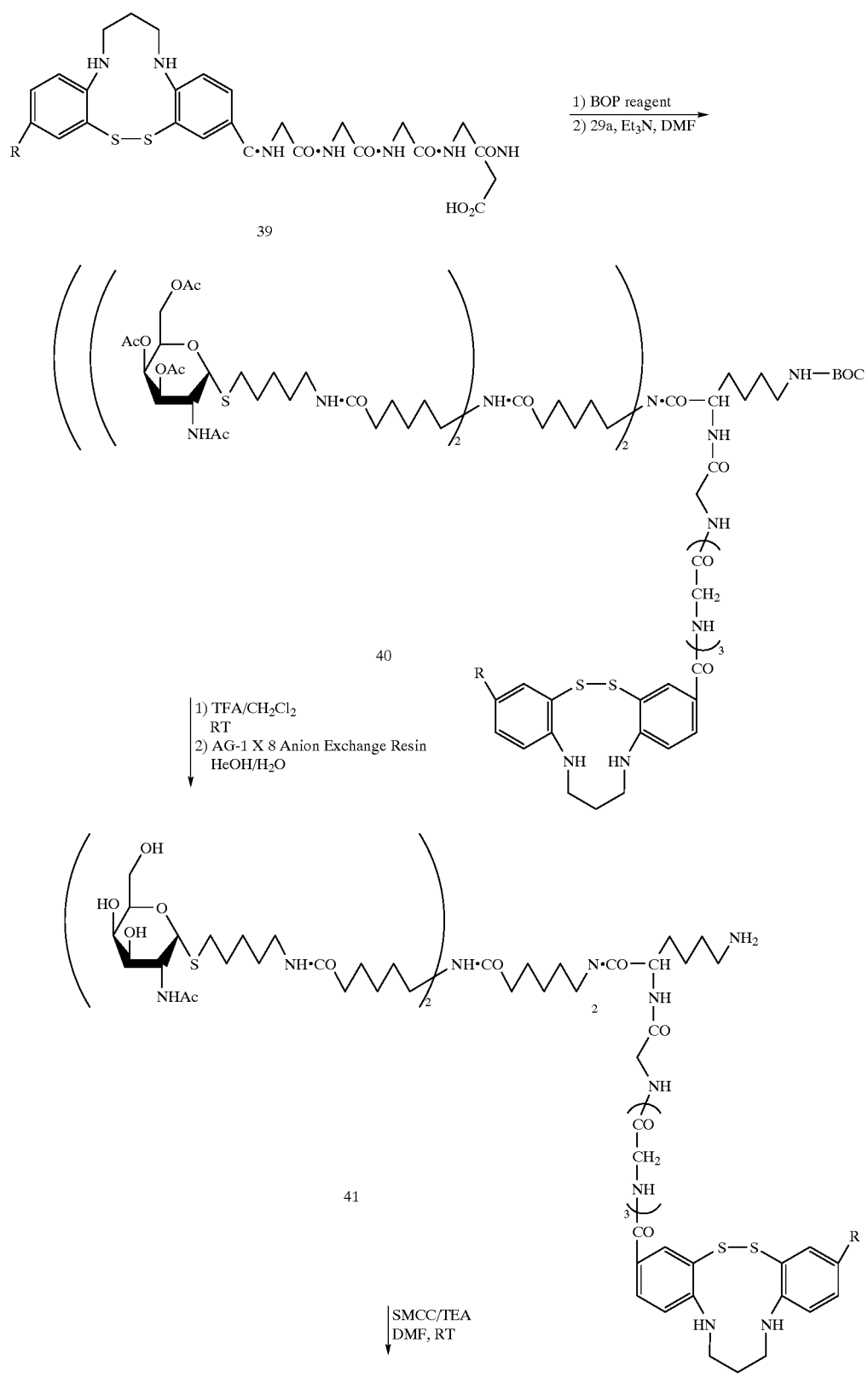

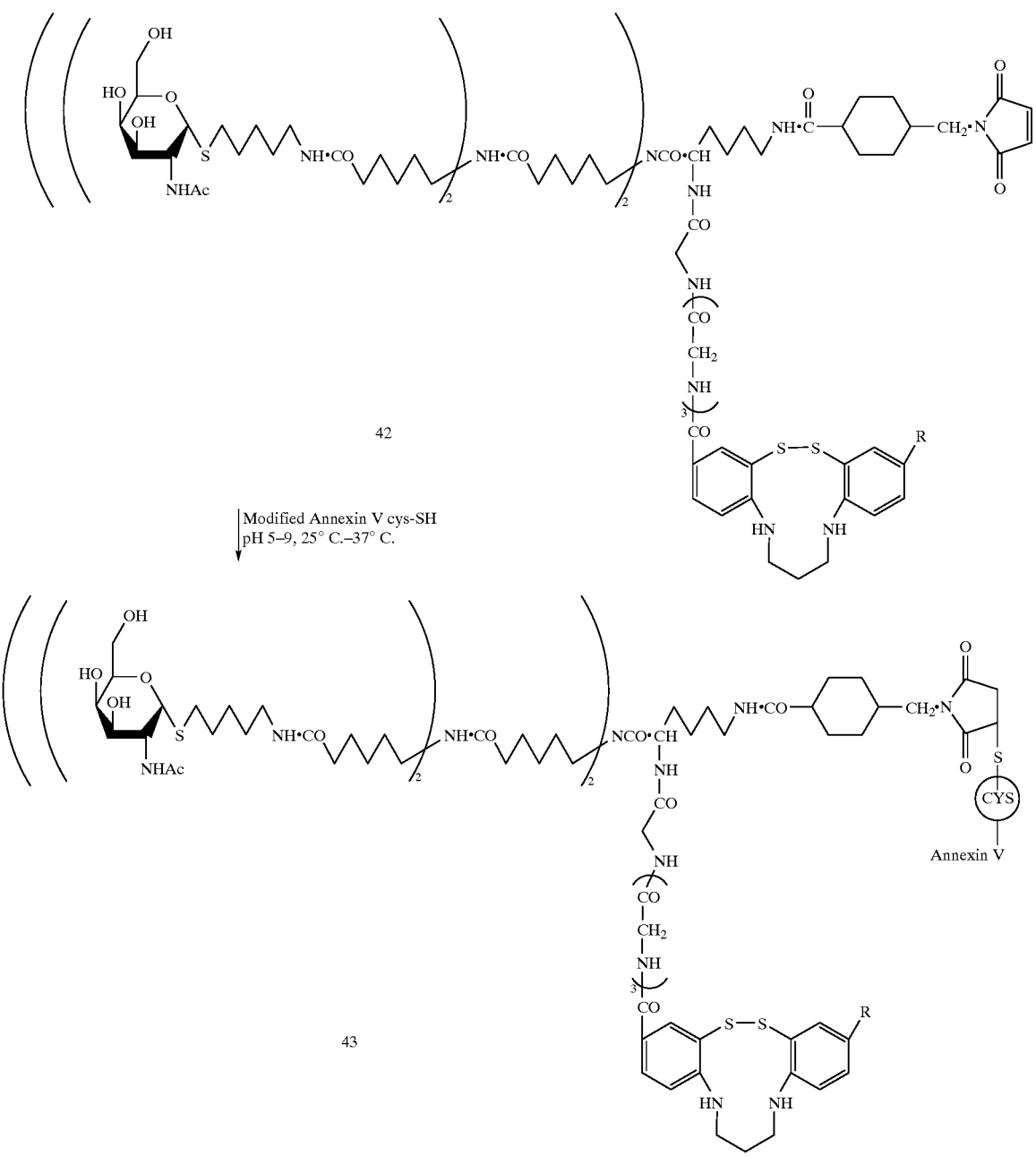

N,N¹-Bis-(2-disulfidyl-4-hydroxycarbonylphenyl 4'-hydroxysuccinimidyl carbonylphenyl)-1,3-propyldiamine, 14

N,N¹-Bis-(2-disulfidyl-4-hydroxycarbonylphenyl)-1,3-propyldiamine 13 (Also 5 FIG. 3) is dissolved in DMF. To the solution, 0.5 equivalents of N-hydroxysuccinimide is added and stirred magnetically. To the reaction mixture, 0.6 equivalents of 10-(3-dimethyl-aminopropyl)-3-ethylcarbodimide (CDI) as a hydrochloride salt is added. The pH of the reaction mixture is adjusted to between 5 and 6 with Phosphate butter, 1.0M, pH 7.0. The progress of the reaction is monitored by thin layer chromatography on silica gel plates. Solvent from the reaction mixture is removed under vacuum and dried. The crude product is purified on silica gel column chromatography. The fractions containing the mono NHS ester and mono acid are pooled and the solvent removed under reduced pressure and dried to yield the desired compund 14 in low yield.

Preparation of Annexin v monomer-S-Conjugate of Galactose Cluster-Ligand-of the trifunctional Lysine, 43

The N,N¹-bis(2-disulfidyl-6-hydroycarbonyl phenyl-1,3-propyldiamine mono NHS ester (14) is reacted with 1.2 equivalents of t-butyl tetra glycine carboxylate as its hydrochloride salt, commercially available from Aldrich Chemical Company, in DMF solvent using 10 equivalents of triethylamine as a base. The solvent from the reaction mixture is removed under vacuum and the crude product purified on silica gel column chromatography to afford the peptide adduct 38 in good yield. The tertiary butyl ester of the compound 38 is removed in TFA-CH₂Cl₂ mixture. The mixture is stirred for 1 hour and the solvent removed and dried to yield the carboxylic acid of the ligand-tetra peptide adduct 39 in good yield. The carboxyl functionality of the tetra glycine ligand adduct 39 is conjugated with 1.2 equivalents of 3,5,6-tri o-acetyl NH acetyl tetra galactosyl εE-HNBOC α-amino lysine 29a in DMF solvent and 5 equivalents of triethylamine in presence of 1.2 equivalents of BOP reagent. The solvent from the reaction mixture is removed under vacuum and dried. The crude product is purified by silica gel chromatography to afford compound 40 of the trifunctional lysine epsilon amine protected as BOC.

The BOC group of compound 40 is removed in TFA-CH$_2$Cl$_2$ mixture. The reaction mixture is stirred at room temperature for 1–2 hours. Solvent from the reaction mixture is removed and dried. The crude product is then triturated with AG-1 X8 anion exchange resin in aqueous methanol at room temperature. The mixture is filtered, and the resin is rinsed with methanol. The filtrates are combined and concentrated to afford o-deacetyl-N-acetyl tetra galactosyl ligand-chelating compound of the trifunctional Lysine as an epsilon amine, 41 in good yield. The amino compound 41 is derviatized with 1.2 equivalents of SMCC reagent in 10 equivalents of triethylamine and DMF solvent. The reaction mixture is stirred at room temperature for 1–2 hours. The solvent is removed under reduced pressure and the crude product is chromatographed on silica gel column to yield maleimidyl tetra galactose tetra glycyl peptidyl ligand-chelating compound of the trifunctional Lysine, 42 in good yield. The maleimidyl derivative 42 is then conjugated with modified Annexin V-SH at pH 5–9 in borate buffer and/or phosphate buffer. The reaction mixture is incubated at 25–37° C. for 2 hours. The sulfur adduct of the modified Annexin conjugate is then purified by gel filtration to give the conjugate 43 in good yield.

EXAMPLE XVIII

Procedure for Dimer-N-Galactose-Chelating Compound or

S-Annexin-N-Galactose (Endogenous Chelation, no dimer) or

S-Annexin-N-Galactose-Chelating Compound

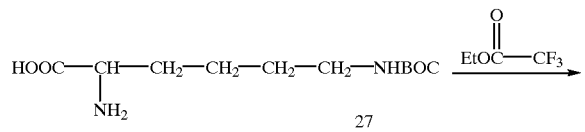

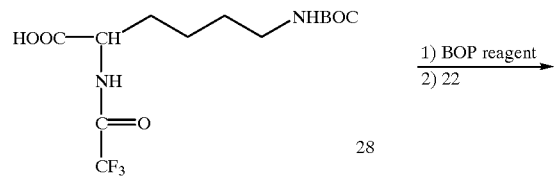

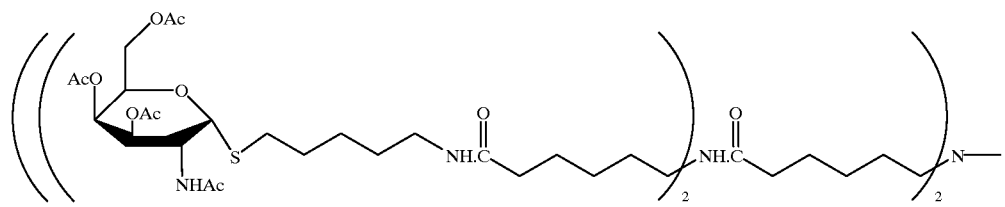

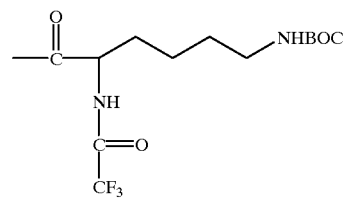

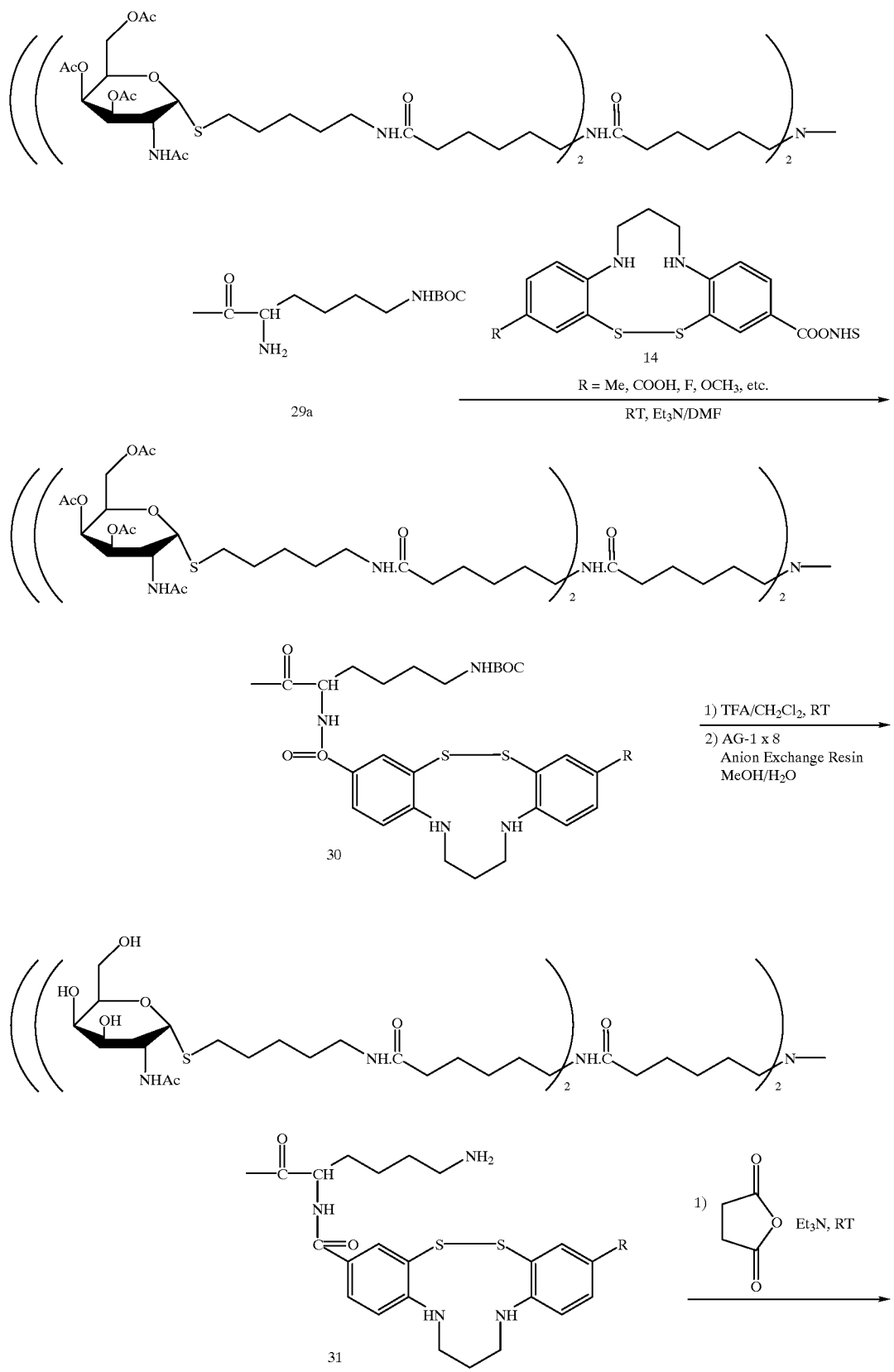

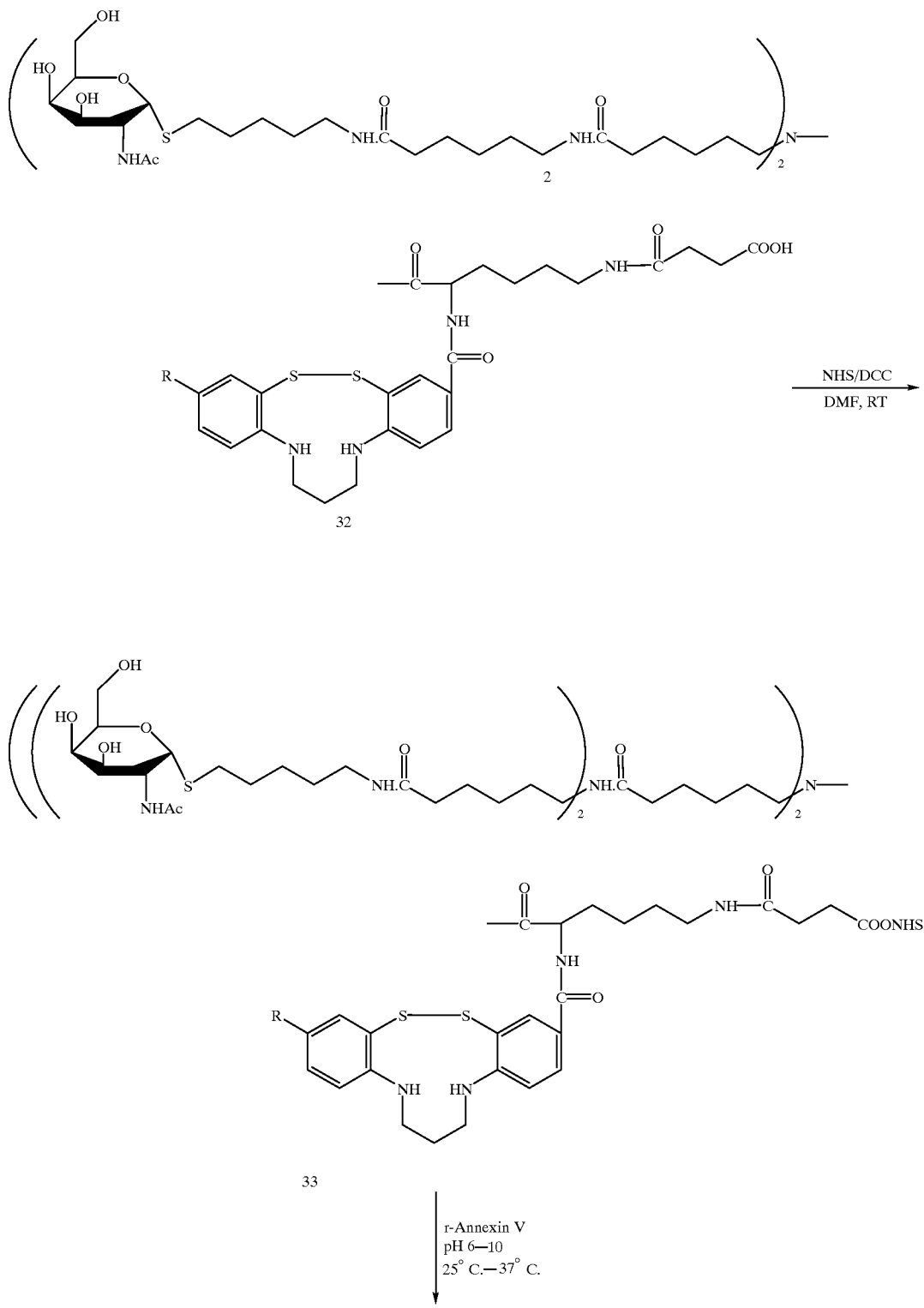

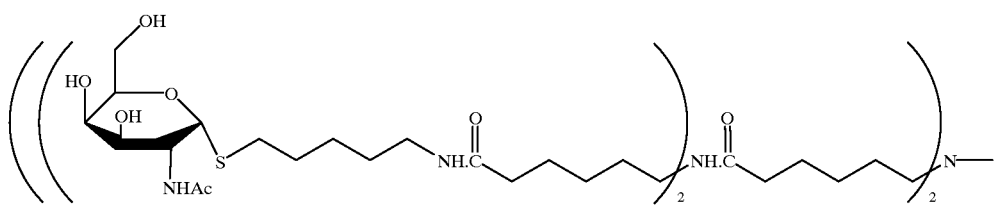

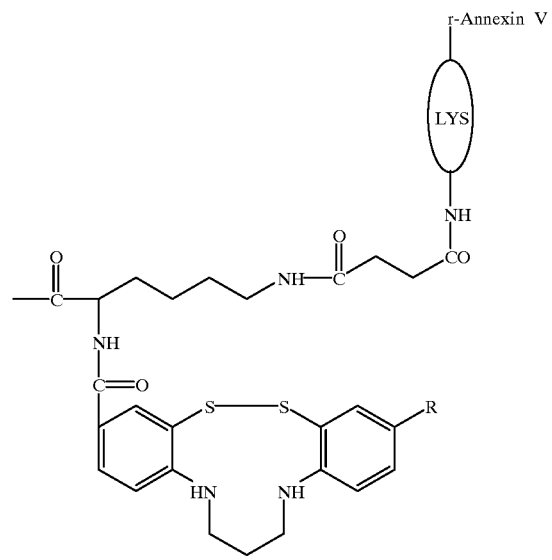

34

Preparation of N ε-(tert-butoxy carbonyl) N¹-α-trifluoroacetyl L-lysine, 28

To a 250 ml round bottom flask, charged with 10.0 g (0.041 mole) of N ε-(tert-butoxy carbonyl) L-lysine 27, commercially available from BACHEM Bioscience Inc. (subsidiary of BACHEM Switzerland, 3700 Horizon Drive, Renaissance at Gulph Mills, King of Prussia, Pa., 19406, U.S.A.), and 100 ml of methanol is added 10.0 g (0.07 mole) of ethyl trifluoroacetate followed by 20.0 ml (0.144 mole) of triethylamine. The mixture is stirred at 20–30°0 C. for 20 hours and then concentrated via rotary evaporation. The residue is diluted with 50 ml of diethyl ether and then filtered. The filtrate is then washed with 3×30 ml aliquots of 1N aqueous HCL, 20 ml of deionized water, and finally with 20 ml of deionized water. The organic phase is dried over anhydrous magnesium sulfate, filtered and concentrated. The residue is distilled under vacuum to yield product 28 in good yield. N ε-(tert-butoxy carbonyl) N¹-α-trifluoroacetyl L-lysine is reacted with tri-o-acetyl tet-Gal-NAC 1-a-S-Pentylamine in the presence of a BOP reagent. The activated carboxylic acid reacts with the clustered galactosamine in DMF and Triethylamine to afford galactose cluster lysine adduct 29 in good yield. The N α-trifluoroacetyl protection of the lysine is removed to afford Primary α-amino lysine-galactose cluster 29a in moderate yield.

Conjugation of galactose cluster with chelating compound and annexin components, 34

Tetragalactosyl-chelating compound construct, 29a–34

To a mixture of amine extended tetra-galactosyl amine, 29a 1.2 equivalents of N,N¹-bis (2 disulfidyl-4-hydroxycarbonylpheny)-1,3-propyldiamine mono NHS ester in dimethylforma-mide, 5 equivalents of triethylamine is added. The mixture is stirred at 15–30° C. for 2–24 hours and then concentrated. The residue is diluted with deionized water, and the pH is adjusted to 2.5 by the addition of 1N aqueous hydrochloric acid. The mixture is washed with ethyl acetate. The aqueous phase is concentrated. The residue is chromatographed on reverse Phase C-18 silica gel. The fractions containing the product are combined and concentrated to give the product 30 in good yield. The BOC protected epsilon amino functionality of compound 30 is removed by stirring at room temperature in trifluoroacetic acid-methylene chloride mixture. The resulting primary epsilon amino compound, 31 is triturated with AG-1 X8 anion exchange resin (hydroxide form) in methanol-H₂O mixture at room temperature for 15 hours. The mixture is filtered, and the resin is rinsed with methanol. The filtrates are combined and concentrated to afford the o-deacetylated N-acetyl galactose cluster which upon reaction with succinic anhydride in triethylamine and DMF at room temperature afforded the hemisuccinic acid adduct 32 in good yield. The hemisuccinic acid functionality of compound 32 is activated via 1.1 equivalents of N-hydroxy-succinimide reaction in presence of 1.2 equivalents of DCC coupling reagent. The reaction product is concentrated in vacuo to yield a crude product which upon purification on silica gel chromatography afford the NHS ester 33 in moderate yield. The NHS ester of the galactose cluster chelating compound adduct of the trifunctional lysine is reacted with Annexin V at PH 6–10 in the presence of DMSO (0–15%). The reaction is carried out at 25° C.–37° C. for 1–2 hours. The crude conjugate is purified by gel filtration chromatography to afford galactose cluster-chelating compound-Annexin V lysine conjugate 34 in good yield.

EXAMPLE XIX

Radiolabeling Procedures for Examples XVI, XVII and XVIII

Characterization of Galactose Cluster-Chelate-Annexin V Conjugates

Protein concentration is determined using $A_{280}$ of 0.6 for 1 mg/mL solution of annexin V. The number of galactose residues per molecule of annexin V is determined by measuring the total number of reactive amines on Annexin V before and after reaction with galactosyl Cluster-Chelate conjugate using trinitrobenzenesulfonic acid, as described by Habeeb, *Analytical Biochemistry*, 14: 328–36,1966.

Also the number of galactose residues per molecule of modified annexin V conjugated via sulfhydryl is determined by measuring the reactive sulfhydryl on Annexin V before and after reaction with galactosyl cluster chelate conjugate using 3-carboxy-4-mitrophenyl disulfide; DTNB; Ellman's reagent, as described by Deakin, et. al.; *Biochem. J.*, 89: 296, 1963. The ability of galactose-chelate-annexin V to bind to activated platelets is assessed by determining its ability to inhibit the binding of unmodified, I-125-radiolabeled annexin V to freshly isolated human platelets, following the method of Thiagarajan and Tait, *J. Biol. Chem.*, 265: 17,240–43, 1990.

RADIOLABELING PROCEDURE FOR USE IN POST-FORMED CHELATE CONJUGATION METHOD

Method A: Stannous gluconate kits are prepared containing 5 mg sodium gluconate, 100 micrograms stannous chloride, 1.0 mg (1 mg/mL) of galactose cluster-chelate-annexin V, and 0.1 to 1.0 mg of lactose, The pH is maintained between 5 and 7 using HCl, acetic acid or NaOH. To the stannous gluconate kit is added 1.0 mL sodium pertechnetate (Tc-99m) with a specific activity of about 50 mCi. The vial is incubated at 25–30° C. for 5–30 minutes. The percent formation of labeled conjugate, remaining pertecnetate, and hydrolyzed/reduced technetium is determined by ITLC in 12% TCA as developing solvent.

Method B: Stannous tartrate kits are prepared in an evacuator vial under nitrogen to contain 0.5 mL of disodium tartrate (10 mg/mL) and 0.1 mL stannous chloride (1.0 mg/mL in ethanol). The pH of the solution is kept between 5 and 7, preferably 6.0. To this stannous tartrate solution is added 1.0 mL of sodium pertechnetate (50 mCi), and the solution is allowed to stand at room temperature. In an evacuated vial, 200 μl of sodium phosphate (0.5M, pH 8 or 10) and 1.0 mL of galactose cluster-chelating compound-annexin V conjugate (1.0 mg/mL) are added successively. Then Tc-99m-tartrate (50 mCi) is added, and the vial is incubated at 25–37° C. for 5–30 minutes. The percent formation of labeled conjugate, remaining pertecnetate, and hydrolyzed/reduced technetium is determined by ITLC in 12% (w/v) trichloroacetic acid as developing solvent.

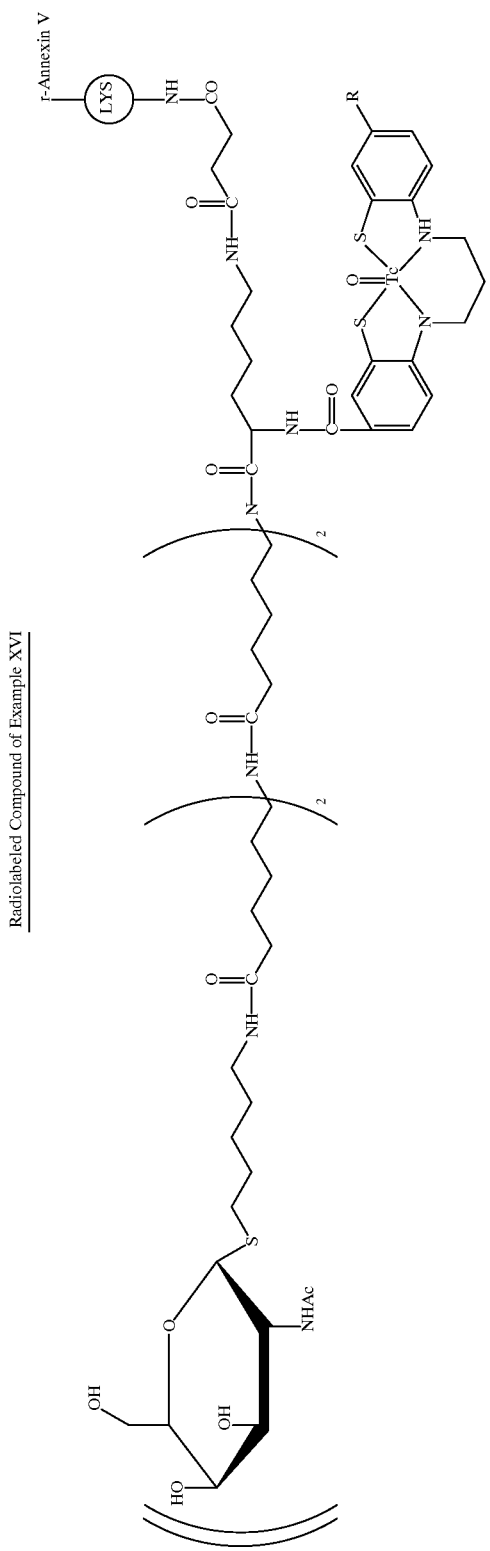
Radiolabeled Compound of Example XVI

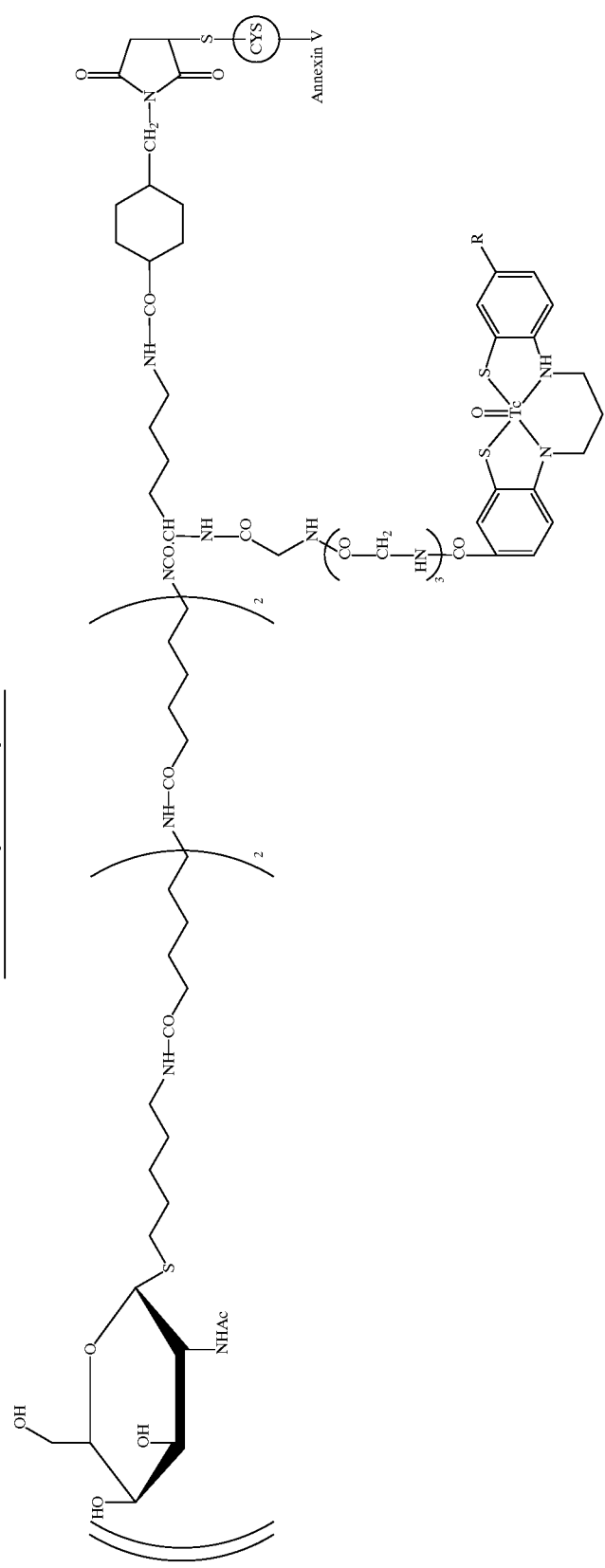
Radiolabeled Compound of Example XVII
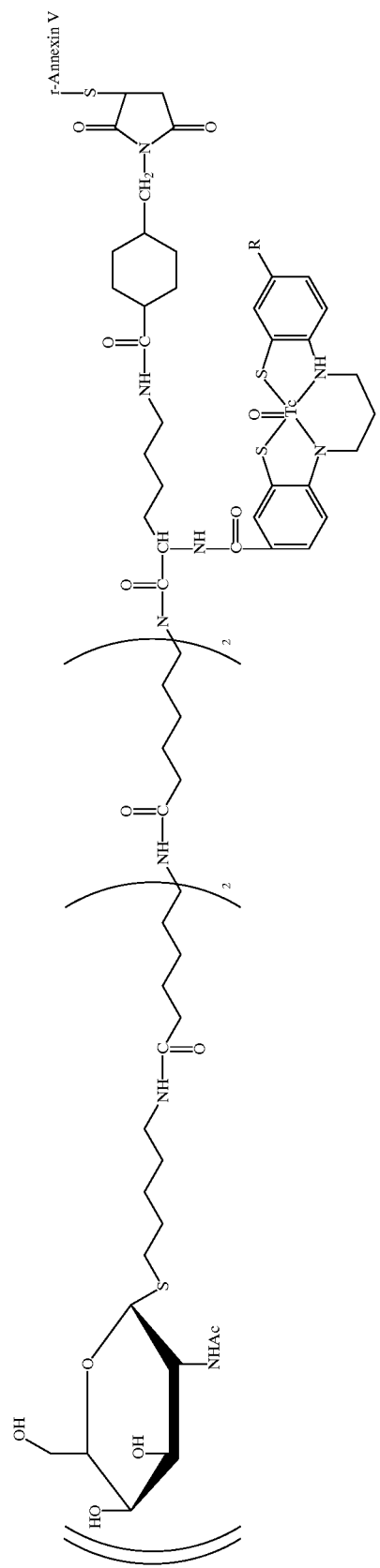
Radiolabeled Compound of One Embodiment of Example XVIII

EXAMPLE XX

Production of Modified Annexin Dimer by Recombinant Methods

A dimer of two modified annexin V molecules can be prepared by recombinant-DNA methods following the methods described by Tait et al., *J. Biol. Chem.,* 270: 21594–21599, 1995, for construction and expression of chimeric molecules containing annexin V. First, PCR is performed on the annexin V cDNA template pPAP-I-1.6 with oligonucleotide primers that introduce an NdeI site at the 5' end and a BamHI site at the 3' end of the annexin V coding sequence (amino acids 1–320+stop codon), and this PCR product is cloned by standard procedures into the NdeI and BamHI sites of plasmid pET-12a (Novagen Corp., Madison, Wis. to create plasmid pET-12a-Ax1. PCR is then performed again on the annexin V cDNA template pPAP-I-1.6 with oligonucleotide primers that introduce an NdeI site at the 5' end and a sequence encoding the amino acids Gly-Gly-Gly-Gly-Gly-Gly (SEQ ID NO:11) followed by an NdeI site at the 3' end of the annexin V coding sequence (amino acids 1–320). This PCR product is then cloned by standard procedures into the NdeI site of plasmid pET-12a-Ax1 to create plasmid pET-12a-Ax2. Production of the dimeric annexin V molecule by cytoplasmic expression in *E. coli* from plasmid pET-12a-Ax2 is then performed by standard procedures, for example as shown by Tait et al., *J. Biol. Chem.,* 270: 21594–21599, 1995.

All publications and patent applications mentioned in this specification are herein incorporated by reference to the same extent as if each individual publication or patent application was specifically and individually incorporated by reference.

From the foregoing it will be appreciated that, although specific embodiments of the invention have been described herein for the purpose of illustration, various modifications may be made without deviating form the spirit and scope of the invention.

What is claimed is:

1. A conjugate of a modified annexin, a hexose moiety and a chelating compound, comprising:
   a modified annexin, wherein the modification provides an accessible sulfhydryl group to which the hexose moiety or the chelating compound is conjugated;
   a hexose moiety recognized by a mammalian liver receptor; and
   a $N_xS_y$ chelating compound, wherein x is an integer from 2–4 and y is an integer from 0–4, and wherein the hexose moiety is conjugated to the modified annexin directly or via the chelating compound and the chelating compound is conjugated to the modified annexin directly or via the hexose moiety.

2. The conjugate of claim 1, wherein the hexose moiety comprises a cluster containing at least three hexose residues, connected in a branched configuration, and wherein the cluster is conjugated via a single point of attachment to the annexin.

3. The conjugate of claim 2, wherein the hexose residues are independently selected from the group consisting of galactose, mannose, mannose 6-phosphate, N-acetylglucosamine, pentamannosyl phosphate, glucose, N-galactosamine, N-acetylgalactosamine, thioglycosides of galactose, D-galactosides and glucosides.

4. The conjugate of claim 3, wherein the hexose residue is N-acetylgalactosamine.

5. The conjugate of claim 1 or 4, wherein the annexin is annexin V.

6. The conjugate of claim 5, wherein the amino acid at position 316 of the annexin is mutated to serine.

7. The conjugate of claim 5, wherein the modification of the annexin comprises an amino acid extension at the N-terminus, the amino acid extension comprising the accessible sulfhydryl group.

8. The conjugate of claim 7, wherein the extension comprises at least about ten amino acids.

9. The conjugate of claim 7, wherein the extension comprises at least about six amino acids.

10. The conjugate of claim 1, wherein the accessible sulfhydryl group is provided by cysteine.

11. The conjugate of claim 7, wherein the accessible sulfhydryl group is provided by cysteine.

12. The conjugate of claim 1 or 11, wherein the $N_xS_y$ chelating compound comprises an $N_2S_2$ chelating compound.

13. The conjugate of claim 12, wherein the chelating compound has the following structure:

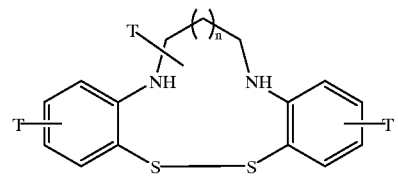

wherein T is H, $CH_3$ or bears a functional group and n is 0 or 1.

14. The conjugate of claim 2 or 13, wherein the cluster comprises:

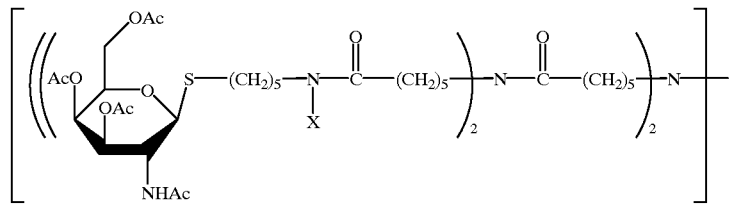

wherein X is H or $CH_3$.

15. The conjugate of claim 14, wherein the conjugate has the following configuration:
   cluster-modified annexin V-chelating compound.

16. The conjugate of claim 14, wherein the conjugate has the following configuration:
   chelating compound-cluster-modified annexin V.

17. The conjugate of claim 14, wherein the conjugate further comprises a cleavable linker between the chelating compound and cluster.

18. The conjugate of claim 17, wherein the cleavable linker is selected from the group consisting of monosaccharides, polysaccharides, polyamino acids, hydroxyakyl acrylamides, polyethylene glycol based hydrophilic polymers, biodegradable polymers containing an ether or ester linkage, dextran or hemisuccinyl esters.

19. The conjugate of claim 18, wherein the conjugate has the following configuration:

chelating comound-cleavable linker-cluster-modified annexin V.

20. The conjugate of any one of claims 1 and 18, further comprising a radionuclide complexed by the chelating compound, wherein the radionuclide is selected from the group consisting essentially of F-18, Cu-64, Ga-67, Ga-68, Re-186, Re-188, I-123, I-125, Cu-67, Tc-99m, Tc-94, Ru-95 and In-111.

21. The conjugate of claim 20, wherein the radionuclide is technetium-99m.

* * * * *

UNITED STATES PATENT AND TRADEMARK OFFICE
CERTIFICATE OF CORRECTION

PATENT NO : 5,968,477
DATED : October 19, 1999
INVENTOR(S) : Kasina et al.

It is certified that errors appear in the above-identified patent and that said Letters Patent are hereby corrected as shown below:

Column 1, line 13, of the specification should read --This invention was made with government support under Grant Number HL-47151 awarded by the National Institute of Health. The Government has certain rights in the invention.--.

Signed and Sealed this

Tenth Day of April, 2001

Attest:

NICHOLAS P. GODICI

Attesting Officer       Acting Director of the United States Patent and Trademark Office